(12) United States Patent
Hyde et al.

(10) Patent No.: US 9,838,645 B2
(45) Date of Patent: Dec. 5, 2017

(54) REMOTE MONITORING OF TELEMEDICINE DEVICE

(71) Applicant: Elwha LLC, Bellevue, WA (US)

(72) Inventors: Roderick A. Hyde, Redmond, WA (US); Jordin T. Kare, Seattle, WA (US); Elizabeth A. Sweeney, Seattle, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 728 days.

(21) Appl. No.: 14/089,478

(22) Filed: Jan. 2, 2014

(65) Prior Publication Data

US 2015/0116126 A1 Apr. 30, 2015

Related U.S. Application Data

(63) Continuation-in-part of application No. 14/068,188, filed on Oct. 31, 2013.

(51) Int. Cl.
*H04N 7/15* (2006.01)
*H04N 7/14* (2006.01)
(Continued)

(52) U.S. Cl.
CPC .............. *H04N 7/141* (2013.01); *G01D 4/02* (2013.01); *A61B 5/0022* (2013.01);
(Continued)

(58) Field of Classification Search
CPC . G06F 19/3418; G06F 19/345; A61B 5/0022; A61B 5/6898; A61B 5/7445;
(Continued)

(56) References Cited

U.S. PATENT DOCUMENTS 3,974,363 A 8/1976 Malinich
4,763,810 A 8/1988 Christiansen
(Continued)

FOREIGN PATENT DOCUMENTS

DE 10240904 A1 3/2004

OTHER PUBLICATIONS

U.S. Appl. No. 14/752,138, Hyde et al.
(Continued)

*Primary Examiner* — Hai Phan
*Assistant Examiner* — Franklin Balseca

(57) ABSTRACT

Methods and systems for monitoring usage of a telemedicine system are described. A monitoring system at a hospital or other central monitoring location provides for communication between personnel at a monitoring location (e.g. a medical care provider) and patient and/or caregiver at a patient location (e.g., the patient's home) via a telemedicine system. The telemedicine system may provide for audiovisual or other communication between the monitoring location and patient location, which may be in combination with medical monitoring or treatment provided with one or more associated article of medical equipment. The medical support monitoring system tracks the amount and type of usage of telepresence system and/or associated medical equipment. Tracked information regarding system usage may be used for various purposes, including billing, quality assurance, data analytics, including population studies of usage patterns, for example. Usage information may be linked to identity of patient, caregiver, or equipment used, or anonymized, depending upon the intended use.

36 Claims, 38 Drawing Sheets

(51) Int. Cl.
*G01D 4/02* (2006.01)
*A61B 5/00* (2006.01)

(52) U.S. Cl.
CPC .... *A61B 5/7445* (2013.01); *A61M 2205/3553* (2013.01); *H04N 7/147* (2013.01); *H04N 7/15* (2013.01); *Y02B 90/245* (2013.01); *Y04S 20/40* (2013.01)

(58) Field of Classification Search
CPC .......... H04N 7/141; H04N 7/147; H04N 7/15; A61M 2205/3553
See application file for complete search history.

(56) References Cited

U.S. PATENT DOCUMENTS

| | | | |
|---|---|---|---|
| 4,843,373 A | 6/1989 | Trickle et al. | |
| 5,014,875 A | 5/1991 | McLaughlin et al. | |
| 5,164,707 A | 11/1992 | Rasmussen et al. | |
| 5,475,376 A | 12/1995 | Chikamitue et al. | |
| 5,694,919 A | 12/1997 | Rubsamen et al. | |
| 6,007,459 A | 12/1999 | Burgess | |
| 6,056,716 A | 5/2000 | D'Antonio et al. | |
| 6,169,707 B1 | 1/2001 | Newland | |
| 6,398,727 B1 | 6/2002 | Bui et al. | |
| 6,450,955 B1 | 9/2002 | Brown et al. | |
| 6,579,242 B2 | 6/2003 | Bui et al. | |
| 6,830,549 B2 | 12/2004 | Bui et al. | |
| 6,925,357 B2 | 8/2005 | Wang et al. | |
| 7,044,744 B2 | 5/2006 | Sellien | |
| 7,142,945 B2 | 11/2006 | Wang et al. | |
| 7,142,947 B2 | 11/2006 | Wang et al. | |
| 7,158,860 B2 | 1/2007 | Wang et al. | |
| 7,161,322 B2 | 1/2007 | Wang et al. | |
| 7,164,969 B2 | 1/2007 | Wang et al. | |
| 7,164,970 B2 | 1/2007 | Wang et al. | |
| 7,171,286 B2 | 1/2007 | Wang et al. | |
| 7,218,992 B2 | 5/2007 | Wang et al. | |
| 7,249,036 B2 | 7/2007 | Bayne | |
| 7,289,211 B1 | 10/2007 | Walsh, Jr. et al. | |
| 7,894,651 B2 | 2/2011 | Gutkowicz-Krusin et al. | |
| 8,074,273 B2 | 12/2011 | Oowaki et al. | |
| 8,117,046 B2 | 2/2012 | Bayne | |
| 8,121,673 B2 | 2/2012 | Tran | |
| 8,123,119 B1 | 2/2012 | Gromley et al. | |
| 8,125,549 B2 | 2/2012 | Dekel | |
| 8,199,244 B2 | 6/2012 | Baraniuk et al. | |
| 8,208,698 B2 | 6/2012 | Bogdan | |
| 8,240,565 B2 | 8/2012 | Iizuka | |
| D669,587 S | 10/2012 | Mayer | |
| 8,348,885 B2 | 1/2013 | Moberg et al. | |
| 8,452,446 B1 | 5/2013 | Madris et al. | |
| 8,544,645 B2 | 10/2013 | Edwards et al. | |
| 8,544,646 B2 | 10/2013 | Bouhraoua et al. | |
| 8,573,140 B2 | 11/2013 | Miyashita | |
| 8,648,269 B2 | 2/2014 | Steele et al. | |
| 8,878,654 B2 | 11/2014 | Cohen-Alloro et al. | |
| 8,926,594 B2 | 1/2015 | Edwards et al. | |
| 9,198,608 B2 | 12/2015 | Hafezi et al. | |
| 2002/0138017 A1 | 9/2002 | Bui et al. | |
| 2003/0088456 A1 | 5/2003 | Ernest et al. | |
| 2003/0093301 A1 | 5/2003 | Chesney et al. | |
| 2003/0095406 A1 | 5/2003 | Lebens et al. | |
| 2003/0130590 A1 | 7/2003 | Bui et al. | |
| 2004/0119814 A1 | 6/2004 | Clisham et al. | |
| 2005/0060198 A1 | 3/2005 | Bayne | |
| 2005/0129108 A1 | 6/2005 | Bendall et al. | |
| 2005/0256392 A1 | 11/2005 | Matory et al. | |
| 2005/0285145 A1 | 12/2005 | Narendran | |
| 2006/0136253 A1* | 6/2006 | Yokota | G06F 21/6254 705/51 |
| 2006/0173355 A1 | 8/2006 | Alfano et al. | |
| 2006/0277254 A1 | 12/2006 | Kenoyer et al. | |
| 2007/0055166 A1 | 3/2007 | Patil | |
| 2007/0112464 A1 | 5/2007 | Wang et al. | |
| 2007/0146545 A1 | 6/2007 | Iwahashi | |
| 2007/0188596 A1 | 8/2007 | Kenoyer | |
| 2008/0004907 A1 | 1/2008 | Bayne | |
| 2008/0140451 A1 | 6/2008 | Hedrick et al. | |
| 2008/0219004 A1 | 9/2008 | Ronda et al. | |
| 2008/0275315 A1 | 11/2008 | Oka et al. | |
| 2008/0309487 A1 | 12/2008 | Chao | |
| 2009/0043253 A1 | 2/2009 | Podaima | |
| 2009/0093688 A1 | 4/2009 | Mathur | |
| 2009/0099866 A1 | 4/2009 | Newman | |
| 2009/0154781 A1 | 6/2009 | Bogdan | |
| 2009/0182582 A1 | 7/2009 | Hammon | |
| 2009/0227877 A1 | 9/2009 | Tran | |
| 2009/0236954 A1 | 9/2009 | Kobayashi et al. | |
| 2009/0259336 A1 | 10/2009 | Ratnakar | |
| 2009/0276090 A1 | 11/2009 | Rajiv | |
| 2009/0292552 A1 | 11/2009 | Chen et al. | |
| 2009/0301925 A1 | 12/2009 | Alloro et al. | |
| 2009/0306487 A1 | 12/2009 | Crowe et al. | |
| 2009/0318815 A1 | 12/2009 | Barnes et al. | |
| 2010/0095799 A1 | 4/2010 | Albin et al. | |
| 2010/0217618 A1* | 8/2010 | Piccirillo | G06F 19/327 705/2 |
| 2011/0064287 A1 | 3/2011 | Bogdan | |
| 2011/0105853 A1 | 5/2011 | Rakowski et al. | |
| 2011/0144455 A1 | 6/2011 | Young et al. | |
| 2011/0148572 A1 | 6/2011 | Ku | |
| 2011/0184249 A1 | 7/2011 | Davis, Jr. | |
| 2012/0041275 A1 | 2/2012 | Sota et al. | |
| 2012/0050606 A1 | 3/2012 | Debevec et al. | |
| 2012/0056060 A1 | 3/2012 | Parton | |
| 2012/0056746 A1* | 3/2012 | Kaigler | A61B 5/0022 340/573.1 |
| 2012/0095352 A1 | 4/2012 | Tran | |
| 2012/0095357 A1 | 4/2012 | Tran | |
| 2012/0101371 A1 | 4/2012 | Verdooner | |
| 2012/0150044 A1 | 6/2012 | Kim | |
| 2012/0157800 A1 | 6/2012 | Tschen | |
| 2012/0197439 A1 | 8/2012 | Wang et al. | |
| 2012/0197464 A1 | 8/2012 | Wang et al. | |
| 2012/0224753 A1 | 9/2012 | Bogdan | |
| 2012/0268462 A1 | 10/2012 | Sota et al. | |
| 2012/0307056 A1 | 12/2012 | Zuzak et al. | |
| 2013/0083185 A1 | 4/2013 | Coleman, III | |
| 2013/0128223 A1 | 5/2013 | Wood et al. | |
| 2013/0173287 A1 | 7/2013 | Cashman et al. | |
| 2013/0278067 A1 | 10/2013 | Poss et al. | |
| 2014/0129248 A1* | 5/2014 | Zuehlsdorff | G06F 19/327 705/2 |
| 2015/0002606 A1 | 1/2015 | Hyde et al. | |
| 2015/0078527 A1 | 3/2015 | Iwamoto et al. | |
| 2015/0081338 A1* | 3/2015 | Lai | G06Q 50/22 705/3 |

OTHER PUBLICATIONS

U.S. Appl. No. 14/089,446, Hyde et al.
U.S. Appl. No. 14/068,188, Hyde et al.
"Cisco TelePresence VX Clinical Assistant™"Installation and User Guide, Jun. 2012, pp. 1-33, Cisco Systems, Inc.
"FacileCare for Home", SoftPro Telemedicine and Healthcare, printed on May 23, 2013, pp. 1-2, http://www.softpro.it/telemedicine/home-care.aspx, SoftPro.
Feng et al., "Computer-assisted technique for the design and manufacture of realistic facial prostheses", British Journal of Oral and Maxillofacial Surgery, Accepted May 2010, pp. 105-109, vol. 48, Elsevier Ltd.
Lamonica, Martin, "iRobot Puts Telemedicine on Auto Pilot", MIT Technology Review, Jul. 26, 2012, pp. 1-4, http://www.technologyreview.com/view/428623/irobot-puts-telemedicine-on-auto-pilot/, MIT Technology Review.
Majid et al., "Integration of stereophotogrammetry and triangulation-based laser scanning system for precise mapping of craniofacial morphology", The International Archives of the Photogrammetry, Remote Sensing and Spatial Information Sciences, 2008, pp. 805-811, vol. XXXVII, Part B5.

(56) References Cited

OTHER PUBLICATIONS

"Making Remote Presence Routine", InTouch Health, printed on May 23, 2013, pp. 1-2, http://www.intouchhealth.com/products-and-services/products/, InTouch Technologies, Inc.

Markiewicz et al., "The Use of 3D Imaging Tools in Facial Plastic Surgery"; Facial Plast Surg Clin N Am, 2011, pp. 655-682, vol. 19, Elsevier Inc.

Meier, Scott, "White Paper Connecting Patients and Physicians Reducing Health Care Costs", HealthNetConnect, Apr. 2012, pp. 1-17, Health Net Connect, Inc.

Shi et al., "Non-contact Reflection Photoplethysmography Towards Effective Human Physiological Monitoring", Journal of Medical and Biological Engineering, 2010, pp. 161-167, vol. 30, No. 3.

"RP-XPRESS", InTouch Health, printed on May 23, 2013, pp. 1-1, http://www.intouchhealth.com/products-and-services/products/rp-xpress/, InTouch Technologies, Inc.

"Transitional Care", InTouch Health, printed on May 23, 2013, pp. 1-1, http://www.intouchhealth.com/clinical-uses/transitional-care/, InTouch Technologies, Inc.

Van Heerbeek et al., "Three dimensional measurement of rhinoplasty results", Rhinology, 2009, pp. 121-125, vol. 47.

\* cited by examiner

```
accepting a first communication from a first user of a first telepresence system at a
patient location via a user input device, the patient medical support system including
the first telepresence system and an article of medical equipment and the first user
being a user of the patient medical support system 702
```
↓
```
transmitting the first communication to a second telepresence system at a first
monitoring location via a two-way communication link for delivery to a second user
at the first monitoring location 704
```
↓
```
receiving a second communication from the second user of the second
telepresence system at the first telepresence system via the two-way
communication link 706
```
↓
```
delivering the second communication to the first user at the patient location 708
```
↓
```
transmitting an operational mode data signal indicative of an operational mode of
the patient medical support system to the first monitoring location 710
```
```
wherein the operational mode data signal is indicative of an operational mode of
the at least one article of medical equipment, and wherein the usage data signal
is indicative of an amount of usage of the at least one article of medical
equipment in the operational mode 1002
```
```
wherein the operational mode data signal is indicative of a turned on
operational mode of the at least one article of medical equipment 1004
```
```
wherein the operational mode data signal is indicative of a turned off
operational mode of the at least one article of medical equipment 1006
```
```
wherein the operational mode data signal is indicative of a standby
operational mode of the at least one article of medical equipment 1008
```
```
wherein the operational mode data signal is indicative of a patient data
gathering operational mode of the at least one article of medical equipment
1010
```
```
wherein the operational mode data signal is indicative of a treatment delivery
operational mode of the at least one article of medical equipment 1012
```
```
wherein the operational mode data signal is indicative of a error operational
mode of the at least one article of medical equipment 1014
```
↓
```
transmitting a usage data signal indicative of usage of the patient medical support
system in the at least one operational mode to the first monitoring location 712
```

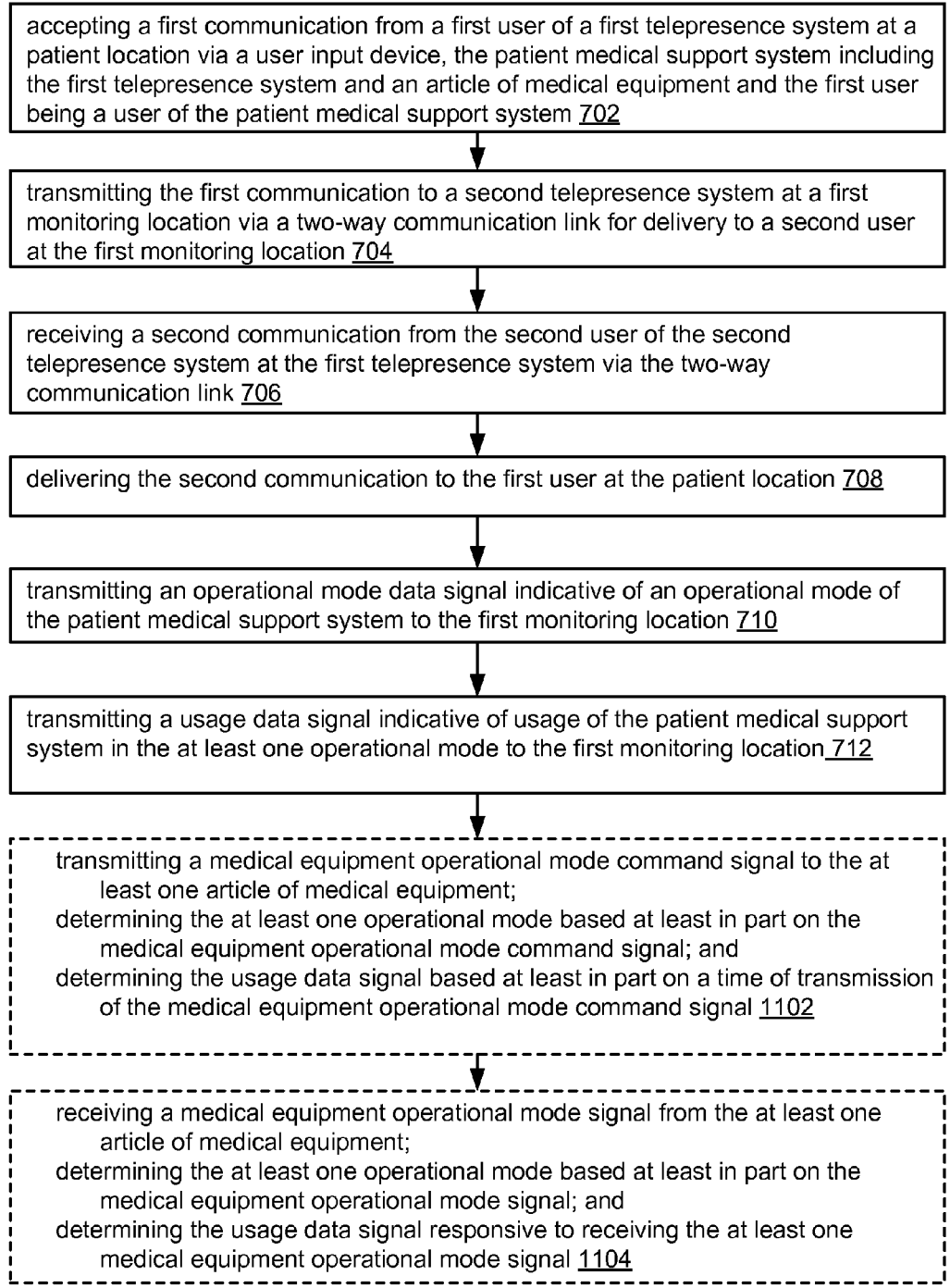

FIG. 12

1200 accepting a first communication from a first user of a first telepresence system at a patient location via a user input device, the patient medical support system including the first telepresence system and an article of medical equipment and the first user being a user of the patient medical support system 702

↓ transmitting the first communication to a second telepresence system at a first monitoring location via a two-way communication link for delivery to a second user at the first monitoring location 704

↓ receiving a second communication from the second user of the second telepresence system at the first telepresence system via the two-way communication link 706

↓ delivering the second communication to the first user at the patient location 708

↓ transmitting an operational mode data signal indicative of an operational mode of the patient medical support system to the first monitoring location 710 wherein the operational mode data signal is indicative of an operational mode of the first telepresence system, and wherein the usage data signal is indicative of an amount of usage of the first telepresence system in the operational mode 1202

| operational mode data signal is indicative of a turned on operational mode of the first telepresence system 1204 | operational mode data signal is indicative of a turned off operational mode of the first telepresence system 1206 | operational mode data signal is indicative of a standby operational mode of the first telepresence system 1208 |
|---|---|---|
| operational mode data signal is indicative of a send communication operational mode of the first telepresence system 1210 | operational mode data signal is indicative of a receive communication operational mode of the first telepresence system 1212 | operational mode data signal is indicative of an audio communication operational mode of the first telepresence system 1214 |
| operational mode data signal is indicative of a video communication operational mode of the first telepresence system 1216 | operational mode data signal is indicative of a user-initiated operational mode of the first telepresence system 1218 | operational mode data signal is indicative of a medical care provider-initiated operational mode of the first telepresence system 1220 |

↓ transmitting a usage data signal indicative of usage of the patient medical support system in the at least one operational mode to the first monitoring location 712

```
┌─────────────────────────────────────────────────────────────────────────┐
│ accepting a first communication from a first user of a first telepresence│
│ system at a patient location via a user input device, the patient medical│
│ support system including the first telepresence system and an article of │
│ medical equipment and the first user being a user of the patient medical │
│ support system 702                                                       │
└─────────────────────────────────────────────────────────────────────────┘
                                    ▼
┌─────────────────────────────────────────────────────────────────────────┐
│ transmitting the first communication to a second telepresence system at  │
│ a first monitoring location via a two-way communication link for delivery│
│ to a second user at the first monitoring location 704                    │
└─────────────────────────────────────────────────────────────────────────┘
                                    ▼
┌─────────────────────────────────────────────────────────────────────────┐
│ receiving a second communication from the second user of the second     │
│ telepresence system at the first telepresence system via the two-way    │
│ communication link 706                                                  │
└─────────────────────────────────────────────────────────────────────────┘
                                    ▼
┌─────────────────────────────────────────────────────────────────────────┐
│ delivering the second communication to the first user at the patient    │
│ location 708                                                             │
└─────────────────────────────────────────────────────────────────────────┘
                                    ▼
┌─────────────────────────────────────────────────────────────────────────┐
│ transmitting an operational mode data signal indicative of an operational│
│ mode of the patient medical support system to the first monitoring      │
│ location 710                                                             │
└─────────────────────────────────────────────────────────────────────────┘
                                    ▼
┌─────────────────────────────────────────────────────────────────────────┐
│ transmitting a usage data signal indicative of usage of the patient      │
│ medical support system in the at least one operational mode to the first │
│ monitoring location 712                                                  │
└─────────────────────────────────────────────────────────────────────────┘
                                    ▼
┌─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─┐
│ receiving a telepresence system operational mode signal from the first  │
│     telepresence system;                                                │
│ determining the at least one operational mode based at least in part on │
│     the telepresence system operational mode signal; and                │
│ determining the usage data signal responsive to receiving the           │
│     telepresence system operational mode signal 1302                    │
└─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─┘
                                    ▼
┌─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─┐
│ transmitting a telepresence system operational mode command signal to   │
│     the first telepresence system;                                      │
│ determining the at least one operational mode based at least in part on │
│     the telepresence system operational mode command signal; and        │
│ determining the usage data signal based at least in part on the time of │
│     transmission of the telepresence system operational mode command    │
│     signal 1304                                                         │
└─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─┘
```

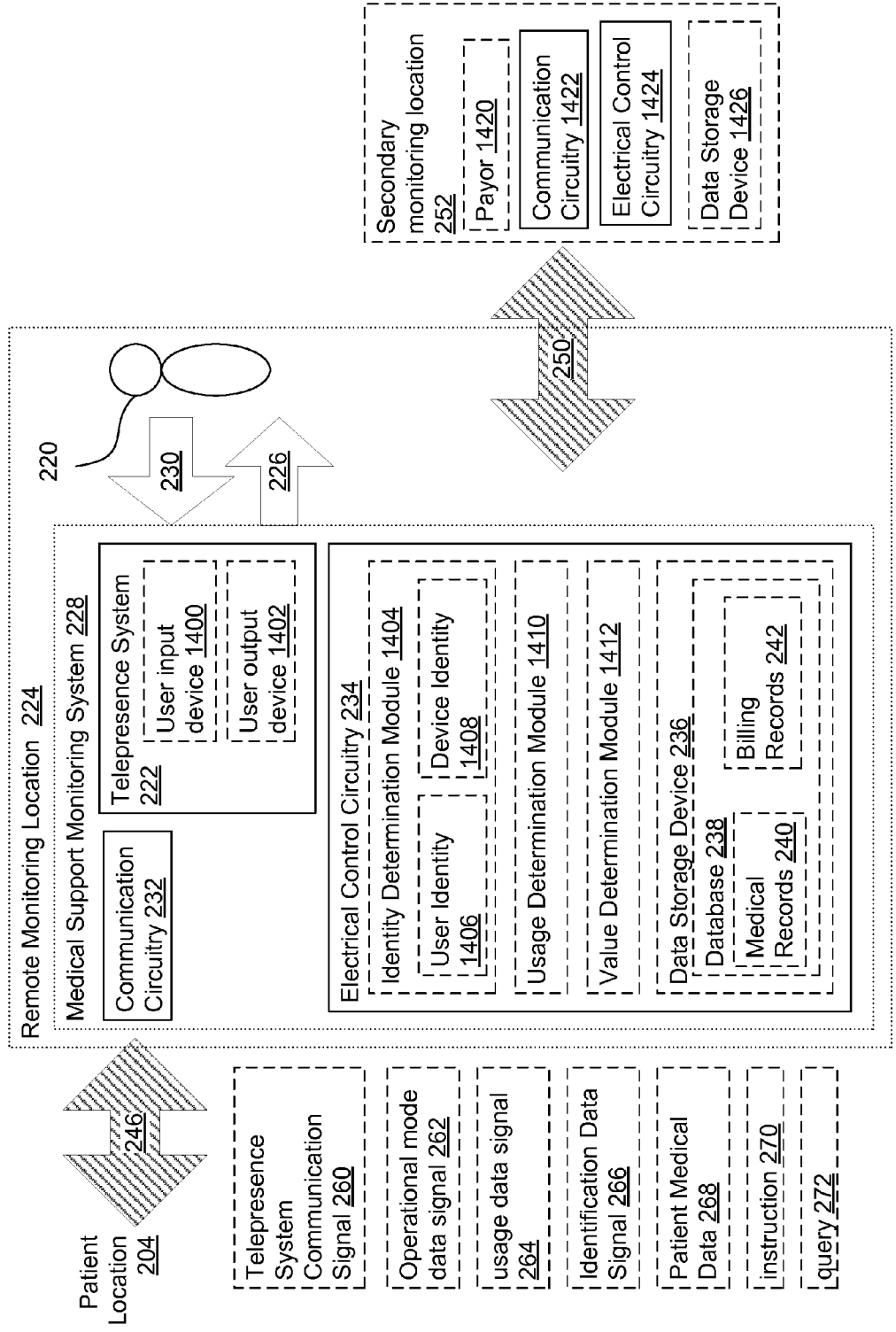

FIG. 15 ← 1500

```
accepting a first communication from a first user of a first telepresence system at a
first monitoring location via a user input device 1502
```
↓
```
transmitting the first communication to a second telepresence system at a patient
location remote from the first monitoring location via a two-way communication link
for delivery to a second user at the patient location, the second user being a user of
the patient medical support system, the patient medical support system including
the second telepresence system and at least one article of medical equipment 1504
```
↓
```
receiving a second communication from the second user at the first monitoring
location via the two-way communication link 1506
```
↓
```
delivering the second communication to the first user via a user output device, the
first telepresence system including the user output device 1508
```
↓
```
receiving a telepresence system operational mode data signal at the first monitoring
location, the telepresence system operational mode data signal indicative of an
operational mode of the second telepresence system 1510
```
↓
```
receiving a telepresence system usage data signal at the first monitoring location,
the telepresence system usage data signal indicative of usage of the second
telepresence system in the operational mode 1512
```
↓
```
receiving a medical equipment operational mode data signal at the first monitoring
location, the medical equipment operational mode data signal indicative of an
operational mode of the at least one article of medical equipment 1514
```
↓
```
receiving a medical equipment usage data signal at the first monitoring location, the
medical equipment usage data signal indicative of usage of the at least one article
of medical equipment in the operational mode 1516
```

```
accepting a first communication from a first user of a first telepresence system at a
first monitoring location via a user input device 1502
```
↓
```
transmitting the first communication to a second telepresence system at a patient
location remote from the first monitoring location via a two-way communication link
for delivery to a second user at the patient location, the second user being a user of
the patient medical support system, the patient medical support system including
the second telepresence system and at least one article of medical equipment 1504
```
↓
```
receiving a second communication from the second user at the first monitoring
location via the two-way communication link 1506
```
↓
```
delivering the second communication to the first user via a user output device, the
first telepresence system including the user output device 1508
```
↓
```
receiving a telepresence system operational mode data signal at the first monitoring
location, the telepresence system operational mode data signal indicative of an
operational mode of the second telepresence system 1510
```
↓
```
receiving a telepresence system usage data signal at the first monitoring location,
the telepresence system usage data signal indicative of usage of the second
telepresence system in the operational mode 1512
```
↓
```
receiving a medical equipment operational mode data signal at the first monitoring
location, the medical equipment operational mode data signal indicative of an
operational mode of the at least one article of medical equipment 1514
```
↓
```
receiving a medical equipment usage data signal at the first monitoring location, the
medical equipment usage data signal indicative of usage of the at least one article
of medical equipment in the operational mode 1516
```
↓
```
storing information in a data storage device at the first monitoring location, wherein
the stored information includes at least one of the operational mode of the second
telepresence system, the usage of the second telepresence system, the operational
mode of the at least one article of medical equipment, and the usage of the at least
one article of medical equipment 1602
```
↓
```
transmitting a signal to a third location for storage in a data storage device at the
third location, wherein the signal contains information regarding at least one of the
operational mode of the second telepresence system, the usage of the second
telepresence system, the operational mode of the at least one article of medical
equipment, and the usage of the at least one article of medical equipment 1604
```

```
┌─────────────────────────────────────────────────────────────────────────────┐
│ accepting a first communication from a first user of a first telepresence   │
│ system at a first monitoring location via a user input device 1502          │
└─────────────────────────────────────────────────────────────────────────────┘
                                      ▼
┌─────────────────────────────────────────────────────────────────────────────┐
│ transmitting the first communication to a second telepresence system at a   │
│ patient location remote from the first monitoring location via a two-way    │
│ communication link for delivery to a second user at the patient location,   │
│ the second user being a user of the patient medical support system, the     │
│ patient medical support system including the second telepresence system     │
│ and at least one article of medical equipment 1504                          │
└─────────────────────────────────────────────────────────────────────────────┘
                                      ▼
┌─────────────────────────────────────────────────────────────────────────────┐
│ receiving a second communication from the second user at the first          │
│ monitoring location via the two-way communication link 1506                 │
└─────────────────────────────────────────────────────────────────────────────┘
                                      ▼
┌─────────────────────────────────────────────────────────────────────────────┐
│ delivering the second communication to the first user via a user output     │
│ device, the first telepresence system including the user output device 1508 │
└─────────────────────────────────────────────────────────────────────────────┘
                                      ▼
``` receiving a telepresence system operational mode data signal at the first monitoring location, the telepresence system operational mode data signal indicative of an operational mode of the second telepresence system 1510

| turned on operational mode 1702 | turned off operational mode 1704 | standby operational mode 1706 | send communication operational mode 1708 | receive communication operational mode 1710 |

| audio communication operational mode 1712 | video communication operational mode 1714 | user-initiated operational mode 1716 | medical care provider-initiated operational mode 1718 | receiving a telepresence system usage data signal at the first monitoring location, the telepresence system usage data signal indicative of usage of the second telepresence system in the operational mode 1512 receiving a medical equipment operational mode data signal at the first monitoring location, the medical equipment operational mode data signal indicative of an operational mode of the at least one article of medical equipment 1514 receiving a medical equipment usage data signal at the first monitoring location, the medical equipment usage data signal indicative of usage of the at least one article of medical equipment in the operational mode 1516

FIG. 18 ⟵ 1800

```
┌─────────────────────────────────────────────────────────────────────────────┐
│ accepting a first communication from a first user of a first telepresence   │
│ system at a first monitoring location via a user input device 1502          │
└─────────────────────────────────────────────────────────────────────────────┘
                                       ▼
┌─────────────────────────────────────────────────────────────────────────────┐
│ transmitting the first communication to a second telepresence system at a   │
│ patient location remote from the first monitoring location via a two-way    │
│ communication link for delivery to a second user at the patient location,   │
│ the second user being a user of the patient medical support system, the     │
│ patient medical support system including the second telepresence system     │
│ and at least one article of medical equipment 1504                          │
└─────────────────────────────────────────────────────────────────────────────┘
                                       ▼
┌─────────────────────────────────────────────────────────────────────────────┐
│ receiving a second communication from the second user at the first          │
│ monitoring location via the two-way communication link 1506                 │
└─────────────────────────────────────────────────────────────────────────────┘
                                       ▼
┌─────────────────────────────────────────────────────────────────────────────┐
│ delivering the second communication to the first user via a user output     │
│ device, the first telepresence system including the user output device 1508 │
└─────────────────────────────────────────────────────────────────────────────┘
                                       ▼
┌─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐
│ receiving a telepresence system operational mode data signal at the first   │
│ monitoring location, the telepresence system operational mode data signal   │
│ indicative of an operational mode of the second telepresence system 1510    │
└ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─┘
                                       ▼
┌─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐
│ receiving a telepresence system usage data signal at the first monitoring   │
│ location, the telepresence system usage data signal indicative of usage of  │
│ the second telepresence system in the operational mode 1512                 │
│ ┌─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐│
│ │ telepresence system usage data signal is indicative of an amount of     ││
│ │ usage of the second telepresence system in the operational mode 1802    ││
│ │ ┌─────────────┬─────────────┬─────────────┬─────────────┐               ││
│ │ │ telepresence│ telepresence│ telepresence│ telepresence│               ││
│ │ │ system usage│ system usage│ system usage│ system usage│               ││
│ │ │ data signal │ data signal │ data signal │ data signal │               ││
│ │ │ is          │ is          │ is          │ is          │               ││
│ │ │ indicative  │ indicative  │ indicative  │ indicative  │               ││
│ │ │ of a        │ of a start  │ of an end   │ of a number │               ││
│ │ │ duration of │ of usage    │ of usage    │ of usage    │               ││
│ │ │ usage 1804  │ 1806        │ 1808        │ events 1810 │               ││
│ │ └─────────────┴─────────────┴─────────────┴─────────────┘               ││
│ └─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘│
└ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─┘
                                       ▼
┌─────────────────────────────────────────────────────────────────────────────┐
│ receiving a medical equipment operational mode data signal at the first     │
│ monitoring location, the medical equipment operational mode data signal     │
│ indicative of an operational mode of the at least one article of medical    │
│ equipment 1514                                                              │
│ ┌──────────────────┬──────────────────┬──────────────────┐                  │
│ │ turned on        │ turned off       │ standby          │                  │
│ │ operational mode │ operational      │ operational      │                  │
│ │ 1812             │ mode 1814        │ mode 1816        │                  │
│ ├──────────────────┼──────────────────┼──────────────────┤                  │
│ │ patient data     │ treatment        │ error            │                  │
│ │ gathering        │ delivery         │ operational      │                  │
│ │ operational mode │ operational      │ mode 1822        │                  │
│ │ 1818             │ mode 1820        │                  │                  │
│ └──────────────────┴──────────────────┴──────────────────┘                  │
└─────────────────────────────────────────────────────────────────────────────┘
                                       ▼
┌─────────────────────────────────────────────────────────────────────────────┐
│ receiving a medical equipment usage data signal at the first monitoring     │
│ location, the medical equipment usage data signal indicative of usage of    │
│ the at least one article of medical equipment in the operational mode 1516  │
└─────────────────────────────────────────────────────────────────────────────┘
```

Database 2000

| User Identity 2002a | Device Identity 2004a |
| User Identity 2002b | Device Identity 2004b |
| User Identity 2002c | Device Identity 2004c |
| User Identity 2002d | Device Identity 2004d |

FIG. 20A

Database 2010

Value = F (UI$_1$, UI$_2$, UI$_3$, DI$_1$, DI$_2$, OM$_1$, OM$_2$, OM$_3$)    2012

Value = Base Rate + (Unit Rate × Usage Amount)    2014

Unit Rate = (UR$_{UI1}$, UR$_{UI2}$, UR$_{UI3}$, UR$_{DI1}$, UR$_{DI2}$, UR$_{OM1}$, UR$_{OM2}$, UR$_{OM3}$)    2016

Base Rate = (BR$_{UI1}$, BR$_{UI2}$, BR$_{UI3}$, BR$_{DI1}$, BR$_{DI2}$, BR$_{OM1}$, BR$_{OM2}$, BR$_{OM3}$)    2018

| | | | | |
|---|---|---|---|---|
| UI$_1$ 2020 | Patient 2040 | Patient X | Patient X | Patient X |
| UI$_2$ 2022 | Caregiver 2042 | Nurse | Physical Therapist | None |
| UI$_3$ 2024 | Medical Care Provider 2044 | Surgeon | Physician | Physician |
| DI$_1$ 2026 | Telepresence System 2046 | Telepresence System Y | Telepresence System Y | Telepresence System Y |
| DI$_2$ 2028 | Medical Equip. 2048 | Blood Press. Monitor | Blood Press. Monitor | Blood Press. Monitor |
| OM$_1$ 2030 | Telepresence Mode1 2050 | Receive Comm. | Send Comm. | Send Comm. |
| OM$_2$ 2032 | Telepresence Mode2 2052 | User 3 Initiated | User 2 Initiated | User 1 Initiated |
| OM$_3$ 2034 | Med.Equip. Mode1 2054 | Standby | Patient Data Gathering | Turned Off |
| Usage Amt 2036 | No. of Minutes 2056 | 15 Minutes | 30 Minutes | 20 Minutes |

```
accepting a first communication from a first user of a first telepresence system at a
first monitoring location via a user input device 1502
```
↓
```
transmitting the first communication to a second telepresence system at a patient
location remote from the first monitoring location via a two-way communication link
for delivery to a second user at the patient location, the second user being a user of
the patient medical support system, the patient medical support system including
the second telepresence system and at least one article of medical equipment 1504
```
↓
```
receiving a second communication from the second user at the first monitoring
location via the two-way communication link 1506
```
↓
```
delivering the second communication to the first user via a user output device, the
first telepresence system including the user output device 1508
```
↓
```
receiving a telepresence system operational mode data signal at the first monitoring
location, the telepresence system operational mode data signal indicative of an
operational mode of the second telepresence system 1510
```
↓
```
receiving a telepresence system usage data signal at the first monitoring location,
the telepresence system usage data signal indicative of usage of the second
telepresence system in the operational mode 1512
```
↓
```
receiving a medical equipment operational mode data signal at the first monitoring
location, the medical equipment operational mode data signal indicative of an
operational mode of the at least one article of medical equipment 1514
```
↓
```
receiving a medical equipment usage data signal at the first monitoring location, the
medical equipment usage data signal indicative of usage of the at least one article
of medical equipment in the operational mode 1516
```
↓
```
determining an amount of usage of the at least one article of medical equipment
    based at least in part on the medical equipment usage data signal;
dissociating information indicative of patient identity from the determined amount of
    usage of the at least one article of medical equipment; and
combining the determined amount of usage of the at least one article of medical
    equipment with amount of usage values determined from a plurality of other
    patients 2202
```

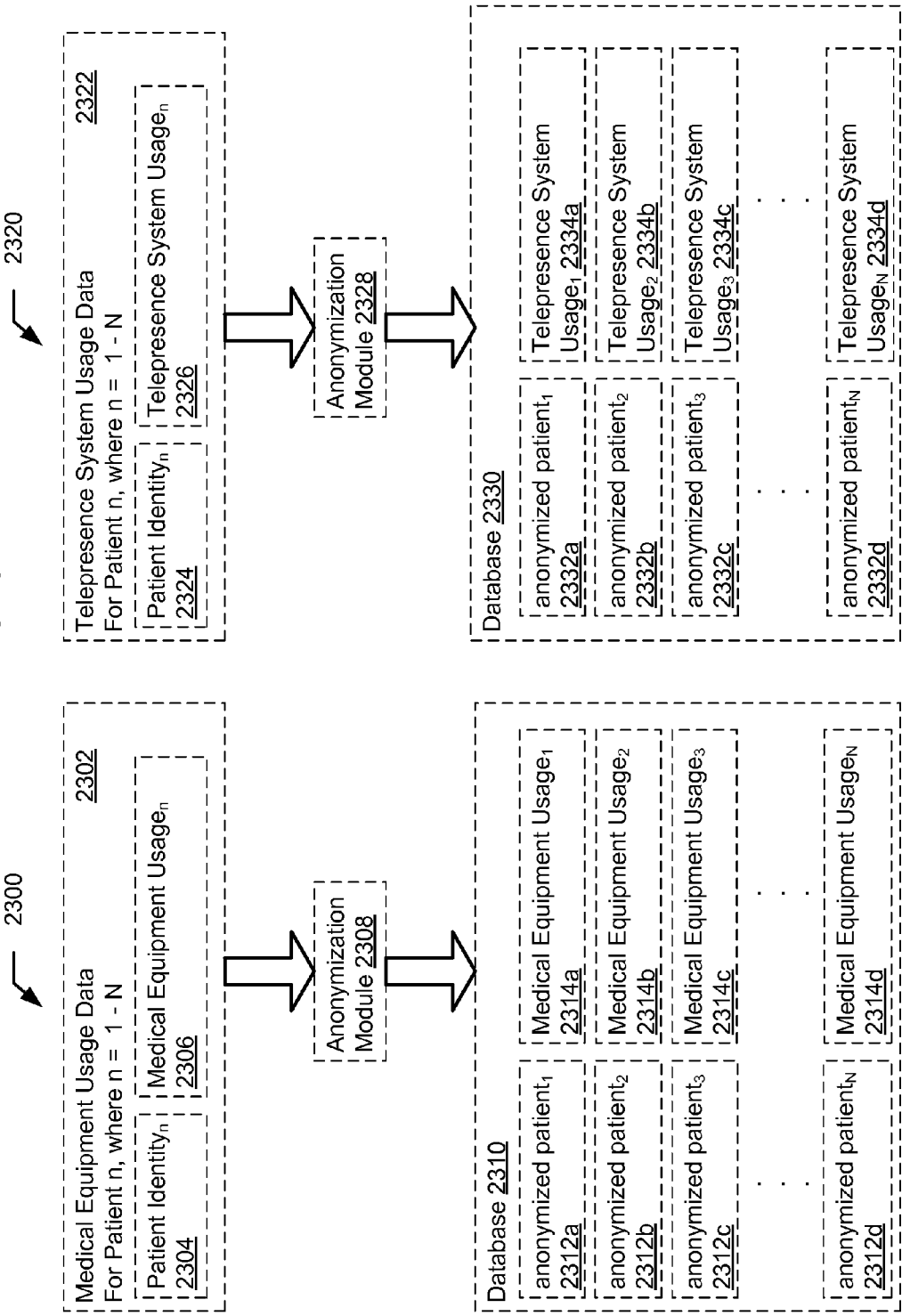

```
accepting a first communication from a first user of a first telepresence system at a
first monitoring location via a user input device 1502
                                    ▼
transmitting the first communication to a second telepresence system at a patient
location remote from the first monitoring location via a two-way communication link
for delivery to a second user at the patient location, the second user being a user of
the patient medical support system, the patient medical support system including
the second telepresence system and at least one article of medical equipment 1504
                                    ▼
receiving a second communication from the second user at the first monitoring
location via the two-way communication link 1506
                                    ▼
delivering the second communication to the first user via a user output device, the
first telepresence system including the user output device 1508
                                    ▼
receiving a telepresence system operational mode data signal at the first monitoring
location, the telepresence system operational mode data signal indicative of an
operational mode of the second telepresence system 1510
                                    ▼
receiving a telepresence system usage data signal at the first monitoring location,
the telepresence system usage data signal indicative of usage of the second
telepresence system in the operational mode 1512
                                    ▼
receiving a medical equipment operational mode data signal at the first monitoring
location, the medical equipment operational mode data signal indicative of an
operational mode of the at least one article of medical equipment 1514
                                    ▼
receiving a medical equipment usage data signal at the first monitoring location, the
medical equipment usage data signal indicative of usage of the at least one article
of medical equipment in the operational mode 1516
                                    ▼
determining an amount of usage of the first telepresence system 2402 determining a value of the usage of the first telepresence system based at least
in part on the amount of usage of the first telepresence system 2404 billing a payor for the        storing the value of the usage of the first
  value of the usage of the      telepresence system in a data storage location
  first telepresence             in association with information identifying the
  system 2406                    patient 2408
```

2502 providing a patient with a patient medical support system, the patient medical support system including:
    at least one article of medical equipment;
    electrical control circuitry configured to:
        determine two or more different operational modes of the at least one article of medical equipment; and
        determine a first usage data signal indicative of an amount of usage of the at least one article of medical equipment in a first operational mode, the first operational mode being one of the two or more different operational modes; and
    communication circuitry for transmitting the first usage data signal and an identification data signal from a patient location remote from a monitoring location to the monitoring location receiving the first usage data signal at the monitoring location 2504 receiving the identification data signal at the monitoring location 2506 determining at least one user identification associated with a user of the patient medical support system based at least in part on the identification data signal 2508 determining an amount of usage of the at least one article of medical equipment based at least in part on the first usage data signal 2510

┌─────────────────────────────────────────────────────────────────────┐
│ providing a patient with a patient medical support system, the patient medical │
│ support system including:                                           │
│     at least one article of medical equipment;                      │
│     electrical control circuitry configured to:                     │
│         determine two or more different operational modes of the at least one │
│             article of medical equipment; and                       │
│         determine a first usage data signal indicative of an amount of usage of │
│             the at least one article of medical equipment in a first │
│             operational mode, the first operational mode being one of the │
│             two or more different operational modes; and            │
│     communication circuitry for transmitting the first usage data signal and an │
│         identification data signal from a patient location remote from the │
│         monitoring location to a monitoring location                │
│ 2502                                                                │
└─────────────────────────────────────────────────────────────────────┘
                                  ▼
┌─────────────────────────────────────────────────────────────────────┐
│ receiving the first usage data signal at the monitoring location 2504 │
└─────────────────────────────────────────────────────────────────────┘
                                  ▼
┌─────────────────────────────────────────────────────────────────────┐
│ receiving the identification data signal at the monitoring location 2506 │
│ ┌─────────────────────────────────────────────────────────────────┐ │
│ │ wherein the identification data signal contains a user identification of a user of │
│ │ the patient medical support system 2602                         │ │
│ └─────────────────────────────────────────────────────────────────┘ │
│ ┌─────────────────────────────────────────────────────────────────┐ │
│ │ wherein the identification data signal contains a device identification of at least a │
│ │ portion of the patient medical support system 2604              │ │
│ │ ┌─────────────────────────────────────────────────────────────┐ │ │
│ │ │ wherein the device identification is associated with a user identification of a │ │ │
│ │ │ user of the patient medical system in a database 2606       │ │ │
│ │ │ ┌─────────────────────────────────────────────────────────┐ │ │ │
│ │ │ │ determining the user identification by retrieving the user identification │ │ │ │
│ │ │ │ associated with the device identification 2608          │ │ │ │
│ │ │ └─────────────────────────────────────────────────────────┘ │ │ │
│ │ └─────────────────────────────────────────────────────────────┘ │ │
│ └─────────────────────────────────────────────────────────────────┘ │
└─────────────────────────────────────────────────────────────────────┘
                                  ▼
┌─────────────────────────────────────────────────────────────────────┐
│ determining at least one user identification associated with a user of the patient │
│ medical support system based at least in part on the identification data signal 2508 │
└─────────────────────────────────────────────────────────────────────┘
                                  ▼
┌─────────────────────────────────────────────────────────────────────┐
│ determining an amount of usage of the at least one article of medical equipment │
│ based at least in part on the first usage data signal 2510          │
│ ┌─────────────────────────────────────────────────────────────────┐ │
│ │ determining the amount of usage of the at least one article of medical equipment │ │
│ │ during a first time period 2610                                 │ │
│ └─────────────────────────────────────────────────────────────────┘ │
└─────────────────────────────────────────────────────────────────────┘
                                  ▼
┌─────────────────────────────────────────────────────────────────────┐
│ associating the amount of usage of the at least one article of medical equipment │
│ with the patient based at least in part on the user identification 2612 │
└─────────────────────────────────────────────────────────────────────┘

2502 providing a patient with a patient medical support system, the patient medical support system including:
- at least one article of medical equipment;
- electrical control circuitry configured to:
  - determine two or more different operational modes of the at least one article of medical equipment; and
  - determine a first usage data signal indicative of an amount of usage of the at least one article of medical equipment in a first operational mode, the first operational mode being one of the two or more different operational modes; and
- communication circuitry for transmitting the first usage data signal and an identification data signal from a patient location remote from the monitoring location to a monitoring location

↓ receiving the first usage data signal at the monitoring location 2504

↓ receiving the identification data signal at the monitoring location 2506

↓ determining at least one user identification associated with a user of the patient medical support system based at least in part on the identification data signal 2508

↓ determining an amount of usage of the at least one article of medical equipment based at least in part on the first usage data signal 2510

↓ dissociating information identifying the patient from the determined amount of usage of the at least one article of medical equipment; and
combining the determined amount of usage of the at least one article of medical equipment with amount of usage values determined from a plurality of other patients 2802

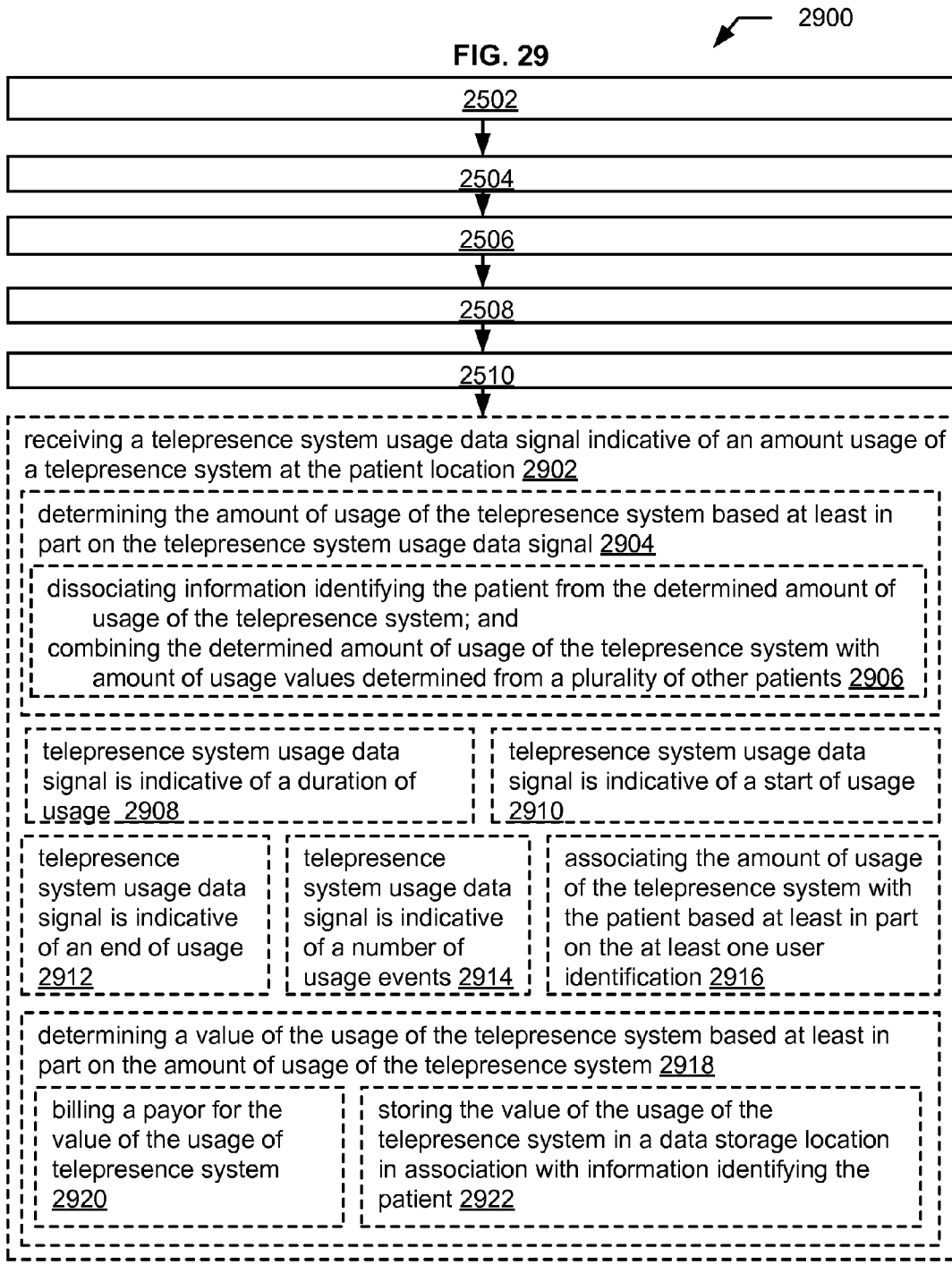

FIG. 31 ← 3100

```
┌─────────────────────────────────────────────────────────────────────────┐
│ receiving a medical equipment operational mode data signal at a first   │
│ monitoring location from the patient medical support system located     │
│ remote from the first monitoring location at a patient location, the    │
│ medical equipment operational mode data signal indicative of a medical  │
│ equipment operational mode of at least two operational modes of the     │
│ article of medical equipment 3102                                       │
└─────────────────────────────────────────────────────────────────────────┘
                                    ▼
┌─────────────────────────────────────────────────────────────────────────┐
│ receiving a medical equipment usage data signal at the first monitoring │
│ location from the patient medical support system, the medical equipment │
│ usage data signal indicative of usage of the article of medical         │
│ equipment in the medical equipment operational mode 3104                │
└─────────────────────────────────────────────────────────────────────────┘
                                    ▼
┌ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐
  receiving a first telepresence system operational mode data signal at
│ the first monitoring location from the patient medical support system, │
  the first telepresence system operational mode data signal indicative
│ of a first telepresence system operational mode of at least two        │
  operational modes of the telepresence system 3106
└ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘
                                    ▼
┌ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐
  receiving a first telepresence system usage data signal at the first
│ monitoring location from the patient medical support system, the first │
  telepresence system usage data signal indicative of usage of the
│ telepresence system in the first telepresence system operational mode  │
  3108
└ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘
                                    ▼
┌─────────────────────────────────────────────────────────────────────────┐
│ determining at least one user identification associated with a user of  │
│ the patient medical support system 3110                                 │
└─────────────────────────────────────────────────────────────────────────┘
                                    ▼
┌─────────────────────────────────────────────────────────────────────────┐
│ storing information to a data storage device, the information regarding │
│ at least one of the medical equipment operational mode, the usage of    │
│ the article of medical equipment, the first telepresence system         │
│ operational mode and the usage of the telepresence system, in           │
│ association with the at least one user identification 3112              │
└─────────────────────────────────────────────────────────────────────────┘
```

```
receiving a medical equipment operational mode data signal at a first monitoring
location from the patient medical support system located remote from the first
monitoring location at a patient location, the medical equipment operational mode
data signal indicative of a medical equipment operational mode of at least two
operational modes of the article of medical equipment 3102
```
↓
```
receiving a medical equipment usage data signal at the first monitoring location from
the patient medical support system, the medical equipment usage data signal
indicative of usage of the article of medical equipment in the medical equipment
operational mode 3104
```
↓
```
receiving a first telepresence system operational mode data signal at the first
monitoring location from the patient medical support system, the first telepresence
system operational mode data signal indicative of a first telepresence system
operational mode of at least two operational modes of the telepresence system
3106
```

| turned on operational mode 3202 | turned off operational mode 3204 | standby operational mode 3206 |
| send communication operational mode 3208 | receive communication operational mode 3210 | audio communication operational mode 3212 |
| video communication operational mode 3214 | user-initiated operational mode 3216 | medical care provider-initiated operational mode 3218 |

↓
```
receiving a first telepresence system usage data signal at the first monitoring
location from the patient medical support system, the first telepresence system
usage data signal indicative of usage of the telepresence system in the first
telepresence system operational mode 3108
```
↓
```
determining at least one user identification associated with a user of the patient
medical support system 3110
```
↓
```
storing information regarding at least one of the medical equipment operational
mode, the usage of the article of the medical equipment, the first telepresence
system operational mode and the usage of the telepresence system, in association
with the at least one user identification, to a data storage device 3112
```

┌─────────────────────────────────────────────────────────────────────────┐
│ receiving a medical equipment operational mode data signal at a first monitoring location from the patient medical support system located remote from the first monitoring location at a patient location, the medical equipment operational mode data signal indicative of a medical equipment operational mode of at least two operational modes of the article of medical equipment 3102 │
└─────────────────────────────────────────────────────────────────────────┘
                                    ▼
┌─────────────────────────────────────────────────────────────────────────┐
│ receiving a medical equipment usage data signal at the first monitoring location from the patient medical support system, the medical equipment usage data signal indicative of usage of the article of medical equipment in the medical equipment operational mode 3104 │
└─────────────────────────────────────────────────────────────────────────┘
                                    ▼
┌ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐
│ receiving a first telepresence system operational mode data signal at the first monitoring location from the patient medical support system, the first telepresence system operational mode data signal indicative of a first telepresence system operational mode of at least two operational modes of the telepresence system 3106 │
└ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘
                                    ▼
┌ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐
│ receiving a first telepresence system usage data signal at the first monitoring location from the patient medical support system, the first telepresence system usage data signal indicative of usage of the telepresence system in the first telepresence system operational mode 3108 │
└ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘
                                    ▼
┌─────────────────────────────────────────────────────────────────────────┐
│ determining at least one user identification associated with a user of the patient medical support system 3110 │
└─────────────────────────────────────────────────────────────────────────┘
                                    ▼
┌─────────────────────────────────────────────────────────────────────────┐
│ storing information regarding at least one of the medical equipment operational mode, the usage of the article of the medical equipment, the first telepresence system operational mode and the usage of the telepresence system, in association with the at least one user identification, to a data storage device 3112 │
├ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┤
│ wherein the data storage device is located at the first monitoring location 3302 │
└ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘
┌ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐
│ transmitting information to a second monitoring location remote from the first monitoring location, wherein the data storage device is located at the second monitoring location, the transmitted information regarding at least one of the medical equipment operational mode, the usage of the article of the medical equipment, the first telepresence system operational mode and the usage of the telepresence system, in association with the at least one user identification 3304 │
└ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘

FIG. 34 ⟵ 3400

```
┌─────────────────────────────────────────────────────────────────────────────┐
│ receiving a medical equipment operational mode data signal at a first        │
│ monitoring location from the patient medical support system located remote   │
│ from the first monitoring location at a patient location, the medical        │
│ equipment operational mode data signal indicative of a medical equipment     │
│ operational mode of at least two operational modes of the article of         │
│ medical equipment 3102                                                       │
└─────────────────────────────────────────────────────────────────────────────┘
                                    ▼
┌─────────────────────────────────────────────────────────────────────────────┐
│ receiving a medical equipment usage data signal at the first monitoring      │
│ location from the patient medical support system, the medical equipment      │
│ usage data signal indicative of usage of the article of medical equipment    │
│ in the medical equipment operational mode 3104                               │
└─────────────────────────────────────────────────────────────────────────────┘
                                    ▼
┌ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐
│ receiving a first telepresence system operational mode data signal at the    │
│ first monitoring location from the patient medical support system, the       │
│ first telepresence system operational mode data signal indicative of a       │
│ first telepresence system operational mode of at least two operational       │
│ modes of the telepresence system 3106                                        │
└ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘
                                    ▼
┌ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐
│ receiving a first telepresence system usage data signal at the first         │
│ monitoring location from the patient medical support system, the first       │
│ telepresence system usage data signal indicative of usage of the             │
│ telepresence system in the first telepresence system operational mode 3108   │
└ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘
                                    ▼
┌─────────────────────────────────────────────────────────────────────────────┐
│ determining at least one user identification associated with a user of the   │
│ patient medical support system 3110                                          │
└─────────────────────────────────────────────────────────────────────────────┘
                                    ▼
┌─────────────────────────────────────────────────────────────────────────────┐
│ storing information regarding at least one of the medical equipment          │
│ operational mode, the usage of the article of the medical equipment, the     │
│ first telepresence system operational mode and the usage of the              │
│ telepresence system, in association with the at least one user               │
│ identification, to a data storage device 3112                                │
└─────────────────────────────────────────────────────────────────────────────┘
                                    ▼
┌ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐
│ determining an amount of usage of the article of medical equipment based     │
│ at least in part on the medical equipment usage data signal 3402             │
│ ┌ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐ │
│ │ determining a value of the usage of the article of medical equipment     │ │
│ │ based at least in part on the amount of usage of the article of medical  │ │
│ │ equipment 3406                                                           │ │
│ │ ┌──────────────────────────┐ ┌──────────────────────────────┐            │ │
│ │ │ billing a payor for the  │ │ storing the value of the     │            │ │
│ │ │ value of the usage of    │ │ usage of the article of      │            │ │
│ │ │ article of medical       │ │ medical equipment in a data  │            │ │
│ │ │ equipment during the     │ │ storage location in          │            │ │
│ │ │ first time period 3408   │ │ association with information │            │ │
│ │ │                          │ │ identifying the patient 3410 │            │ │
│ │ └──────────────────────────┘ └──────────────────────────────┘            │ │
│ │ dissociating information identifying the patient from the determined     │ │
│ │     amount of usage of the article of medical equipment; and             │ │
│ │ combining the determined amount of usage of the article of medical       │ │
│ │     equipment with amount of usage values determined from a plurality    │ │
│ │     of other patients 3412                                               │ │
│ └ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘ │
└ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘
```

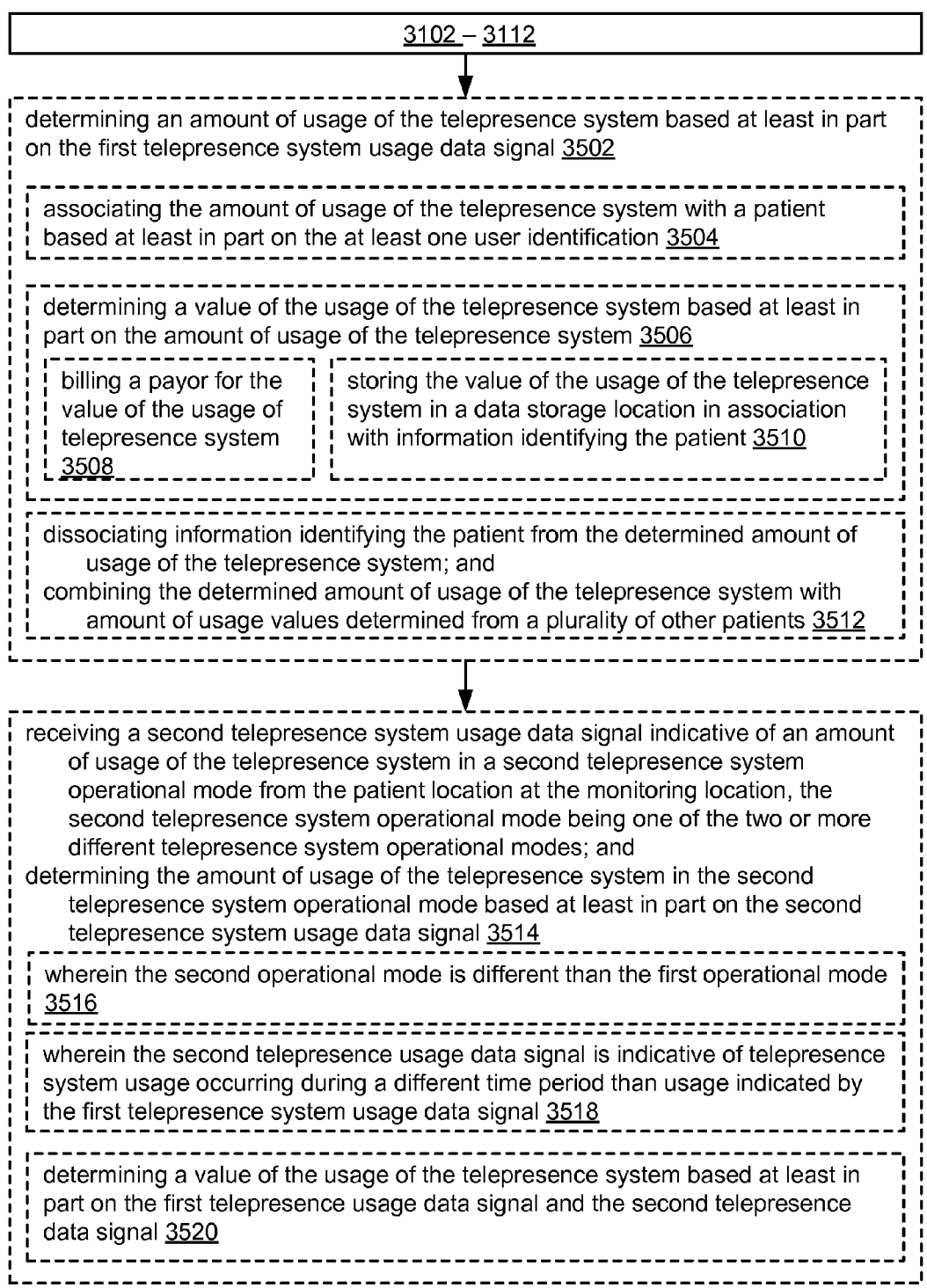

FIG. 36

3600 Article of manufacture

3602 One or more non-transitory machine-readable data storage media

3604 One or more instructions for:
accepting a first communication from a first user of a first telepresence system at a patient location via a user input device, the patient medical support system including the first telepresence system and an article of medical equipment and the first user being a user of the patient medical support system;
transmitting the first communication to a second telepresence system at a first monitoring location via a two-way communication link for delivery to a second user at the first monitoring location;
receiving a second communication from the second user of the second telepresence system at the first telepresence system via the two-way communication link;
delivering the second communication to the first user at the patient location;
transmitting an operational mode data signal indicative of an operational mode of the patient medical support system to the first monitoring location; and
transmitting a usage data signal indicative of usage of the patient medical support system in the at least one operational mode to the first monitoring location.

FIG. 37

3700 Article of manufacture

3702 One or more non-transitory machine-readable data storage media

3704 One or more instructions for:
accepting a first communication from a first user of a first telepresence system at a first monitoring location via a user input device;
transmitting the first communication to a second telepresence system at a patient location remote from the first monitoring location via a two-way communication link for delivery to a second user at the patient location, the second user being a user of the patient medical support system, the patient medical support system including the second telepresence system and at least one article of medical equipment;
receiving a second communication from the second user at the first monitoring location via the two-way communication link;
delivering the second communication to the first user via a user output device, the first telepresence system including the user output device;
receiving a telepresence system operational mode data signal at the first monitoring location, the telepresence system operational mode data signal indicative of an operational mode of the second telepresence system;
receiving a telepresence system usage data signal at the first monitoring location, the telepresence system usage data signal indicative of usage of the second telepresence system in the operational mode;
receiving a medical equipment operational mode data signal at the first monitoring location, the medical equipment operational mode data signal indicative of an operational mode of the at least one article of medical equipment; and
receiving a medical equipment usage data signal at the first monitoring location, the medical equipment usage data signal indicative of usage of the at least one article of medical equipment in the operational mode.

FIG. 38

3800 Article of manufacture

3802 One or more non-transitory machine-readable data storage media

3804 One or more instructions for:

receiving a medical equipment operational mode data signal at a first monitoring location from the patient medical support system located remote from the first monitoring location at a patient location, the medical equipment operational mode data signal indicative of a medical equipment operational mode of at least two operational modes of the article of medical equipment;

receiving a medical equipment usage data signal at the first monitoring location from the patient medical support system, the medical equipment usage data signal indicative of usage of the article of medical equipment in the medical equipment operational mode;

receiving a first telepresence system operational mode data signal at the first monitoring location from the patient medical support system, the first telepresence system operational mode data signal indicative of a first telepresence system operational mode of at least two operational modes of the telepresence system;

receiving a first telepresence system usage data signal at the first monitoring location from the patient medical support system, the first telepresence system usage data signal indicative of usage of the telepresence system in the first telepresence system operational mode;

determining at least one user identification associated with a user of the patient medical support system; and storing information to a data storage device, the stored information regarding at least one of the medical equipment operational mode, the usage of the article of the medical equipment, the first telepresence system operational mode and the usage of the telepresence system, in association with the at least one user identification.

REMOTE MONITORING OF TELEMEDICINE DEVICE

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)).

PRIORITY APPLICATIONS

The present application constitutes a continuation-in-part of U.S. patent application Ser. No. 14/068,188, entitled TELEMEDICINE VISUAL MONITORING DEVICE WITH STRUCTURED ILLUMINATION, naming RODERICK A. HYDE, JORDIN T. KARE, ELIZABETH A. SWEENEY, AND LOWELL L. WOOD, JR. as inventors, filed 31 Oct. 2013, which is currently co-pending or is an application of which a currently co-pending application is entitled to the benefit of the filing date.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In an aspect, a method of communicating usage of a patient medical support system, includes, but is not limited to, accepting a first communication from a first user of a first telepresence system at a patient location via a user input device, the patient medical support system including the first telepresence system and an article of medical equipment and the first user being a user of the patient medical support system; transmitting the first communication to a second telepresence system at a first monitoring location via a two-way communication link for delivery to a second user at the first monitoring location; receiving a second communication from the second user of the second telepresence system at the first telepresence system via the two-way communication link; delivering the second communication to the first user at the patient location; transmitting an operational mode data signal indicative of an operational mode of the patient medical support system to the first monitoring location; and transmitting a usage data signal indicative of usage of the patient medical support system in the at least one operational mode to the first monitoring location. In addition to the foregoing, other method aspects are described in the claims, drawings, and text forming a part of the disclosure set forth herein.

In an aspect, a method of monitoring usage of a patient medical support system includes, but is not limited to, accepting a first communication from a first user of a first telepresence system at a first monitoring location via a user input device; transmitting the first communication to a second telepresence system at a patient location remote from the first monitoring location via a two-way communication link for delivery to a second user at the patient location, the second user being a user of the patient medical support system, the patient medical support system including the second telepresence system and at least one article of medical equipment; receiving a second communication from the second user at the first monitoring location via the two-way communication link; delivering the second communication to the first user via a user output device, the first telepresence system including the user output device; receiving a telepresence system operational mode data signal at the first monitoring location, the telepresence system operational mode data signal indicative of an operational mode of the second telepresence system; receiving a telepresence system usage data signal at the first monitoring location, the telepresence system usage data signal indicative of usage of the second telepresence system in the operational mode; receiving a medical equipment operational mode data signal at the first monitoring location, the medical equipment operational mode data signal indicative of an operational mode of the at least one article of medical equipment; and receiving a medical equipment usage data signal at the first monitoring location, the medical equipment usage data signal indicative of usage of the at least one article of medical equipment in the operational mode. In addition to the foregoing, other method aspects are described in the claims, drawings, and text forming a part of the disclosure set forth herein.

In an aspect, a patient medical support system includes, but is not limited to, at least one article of medical equipment for use at a patient location; a first telepresence system including at least one user input device adapted to accept a communication from a first user of the patient medical support system at the patient location for transmission to a second user of a second telepresence system at a monitoring location remote from the patient location and at least one user output device adapted to present a communication received from the second user at the monitoring location to the first user; electrical control circuitry configured to determine a first medical support system operational mode from at least two different operational modes of the patient medical support system and determine a first medical support system usage data signal indicative of an amount of usage of the patient medical support system in the first medical support system operational mode; and communication circuitry configured to receive the communication from the second user using the second telepresence system at the monitoring location and transmit the communication from the first user, the first medical support system usage data signal and an identification data signal to the monitoring location. In addition to the foregoing, other system aspects are described in the claims, drawings, and text forming a part of the disclosure set forth herein.

In an aspect, an article of manufacture includes, but is not limited to, one or more non-transitory machine-readable data storage media bearing one or more instructions for accepting a first communication from a first user of a first telepresence system at a patient location via a user input device, the patient medical support system including the first telepresence system and an article of medical equipment and the first user being a user of the patient medical support system; transmitting the first communication to a second telepresence system at a first monitoring location via a two-way communication link for delivery to a second user at the first monitoring location; receiving a second communication from the second user of the second telepresence system at the first telepresence system via the two-way communication link; delivering the second communication to the first user at the patient location; transmitting an operational mode data signal indicative of an operational mode of the patient medical support system to the first monitoring location; and transmitting a usage data signal indicative of usage of the patient medical support system in the at least one operational mode to the first monitoring location. In addition to the foregoing, other aspects of articles of manufacture including one or more non-transitory machine-readable data storage media bearing one or more instructions are described in the claims, drawings, and text forming a part of the disclosure set forth herein.

In an aspect, an article of manufacture includes, but is not limited to, one or more non-transitory machine-readable data storage media bearing one or more instructions for accepting a first communication from a first user of a first telepresence system at a first monitoring location via a user input device; transmitting the first communication to a second telepresence system at a patient location remote from the first monitoring location via a two-way communication link for delivery to a second user at the patient location, the second user being a user of the patient medical support system, the patient medical support system including the second telepresence system and at least one article of medical equipment; receiving a second communication from the second user at the first monitoring location via the two-way communication link; delivering the second communication to the first user via a user output device, the first telepresence system including the user output device; receiving a telepresence system operational mode data signal at the first monitoring location, the telepresence system operational mode data signal indicative of an operational mode of the second telepresence system; receiving a telepresence system usage data signal at the first monitoring location, the telepresence system usage data signal indicative of usage of the second telepresence system in the operational mode; receiving a medical equipment operational mode data signal at the first monitoring location, the medical equipment operational mode data signal indicative of an operational mode of the at least one article of medical equipment; and receiving a medical equipment usage data signal at the first monitoring location, the medical equipment usage data signal indicative of usage of the at least one article of medical equipment in the operational mode. In addition to the foregoing, other aspects of articles of manufacture including one or more non-transitory machine-readable data storage media bearing one or more instructions are described in the claims, drawings, and text forming a part of the disclosure set forth herein.

In an aspect, a method of monitoring usage of a patient medical support system includes, but is not limited to, providing a patient with a patient medical support system, the patient medical support system including at least one article of medical equipment, electrical control circuitry configured to determine two or more different operational modes of the at least one article of medical equipment and determine a first usage data signal indicative of an amount of usage of the at least one article of medical equipment in a first operational mode, the first operational mode being one of the two or more different operational modes, and communication circuitry for transmitting the first usage data signal and an identification data signal from a patient location remote from the monitoring location to a monitoring location; receiving the first usage data signal at the monitoring location; receiving the identification data signal at the monitoring location; determining at least one user identification associated with a user of the patient medical support system based at least in part on the identification data signal; and determining an amount of usage of the at least one article of medical equipment based at least in part on the first usage data signal. In addition to the foregoing, other method aspects are described in the claims, drawings, and text forming a part of the disclosure set forth herein.

In an aspect, a method of monitoring usage of a patient medical support system including an article of medical equipment and a telepresence system, includes, but is not limited to receiving a medical equipment operational mode data signal at a first monitoring location from the patient medical support system located remote from the first monitoring location at a patient location, the medical equipment operational mode data signal indicative of a medical equipment operational mode of at least two operational modes of the article of medical equipment; receiving a medical equipment usage data signal at the first monitoring location from the patient medical support system, the medical equipment usage data signal indicative of usage of the article of medical equipment in the medical equipment operational mode; receiving a first telepresence system operational mode data signal at the first monitoring location from the patient medical support system, the first telepresence system operational mode data signal indicative of a first telepresence system operational mode of at least two operational modes of the telepresence system; receiving a first telepresence system usage data signal at the first monitoring location from the patient medical support system, the first telepresence system usage data signal indicative of usage of the telepresence system in the first telepresence system operational mode; determining at least one user identification associated with a user of the patient medical support system; and storing information regarding at least one of the medical equipment operational mode, the usage of the article of the medical equipment, the first telepresence system operational mode and the usage of the telepresence system, in association with the at least one user identification, to a data storage device. In addition to the foregoing, other method aspects are described in the claims, drawings, and text forming a part of the disclosure set forth herein.

In an aspect, a medical support monitoring system includes, but is not limited to, a first telepresence system for use at a first monitoring location including at least one user input device adapted to accept a communication from a first user at the first monitoring location for transmission to a second user of a patient medical support system at a patient location remote from the first monitoring location via a two-way communication link; and at least one user output device adapted to deliver a communication to the first user, the communication received from the second user via the two-way communication link; first communication circuitry forming a portion of the two-way communication link between the medical support monitoring system at the first monitoring location and the patient medical support system at the patient location, the patient medical support system including a second telepresence system, an article of medical equipment, and second communication circuitry forming a portion of a two-way communication link, wherein the first communication circuitry is adapted to: receive at least one operational mode data signal indicative of at least one operational mode of the patient medical support system; receive at least one usage data signal indicative of an amount of usage of the patient medical support system in the at least one operational mode; receive via the two-way communication link the communication from the second user to the first user; and transmit via the two-way communication link the communication from the first user to the second user; a data storage device; and electrical control circuitry configured to: determine the identity of at least one user of the patient medical support system; and control storage of information relating to at least one of the at least one operational mode and the amount of usage of the patient medical support system in the at least one operational mode in the data storage device in association with the identification of the at least one user of the patient medical support system. In addition to the foregoing, other system aspects are described in the claims, drawings, and text forming a part of the disclosure set forth herein.

In an aspect, an article of manufacture includes, but is not limited to, one or more non-transitory machine-readable data storage media bearing one or more instructions for receiving a medical equipment operational mode data signal at a first monitoring location from the patient medical support system located remote from the first monitoring location at a patient location, the medical equipment operational mode data signal indicative of a medical equipment operational mode of at least two operational modes of the article of medical equipment; receiving a medical equipment usage data signal at the first monitoring location from the patient medical support system, the medical equipment usage data signal indicative of usage of the article of medical equipment in the medical equipment operational mode; receiving a first telepresence system operational mode data signal at the first monitoring location from the patient medical support system, the first telepresence system operational mode data signal indicative of a first telepresence system operational mode of at least two operational modes of the telepresence system; receiving a first telepresence system usage data signal at the first monitoring location from the patient medical support system, the first telepresence system usage data signal indicative of usage of the telepresence system in the first telepresence system operational mode; determining at least one user identification associated with a user of the patient medical support system; and storing information regarding at least one of the medical equipment operational mode, the usage of the article of the medical equipment, the first telepresence system operational mode and the usage of the telepresence system, in association with the at least one user identification, to a data storage device. In addition to the foregoing, other aspects of articles of manufacture including one or more non-transitory machine-readable data storage media bearing one or more instructions are described in the claims, drawings, and text forming a part of the disclosure set forth herein.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 10 is a flow diagram of a method of communicating usage of a patient medical support system.

FIG. 11 is a flow diagram of a method of communicating usage of a patient medical support system.

FIG. 12 is a flow diagram of a method of communicating usage of a patient medical support system.

FIG. 13 is a flow diagram of a method of communicating usage of a patient medical support system.

FIG. 14 is a block diagram of a medical support monitoring system.

FIG. 15 is a flow diagram of a method of monitoring usage of a patient medical support system.

FIG. 16 is a flow diagram of a method of monitoring usage of a patient medical support system.

FIG. 17 is a flow diagram of a method of monitoring usage of a patient medical support system.

FIG. 18 is a flow diagram of a method of monitoring usage of a patient medical support system.

FIG. 20A is a depiction of a database.

FIG. 20B is a depiction of a database.

FIG. 22 is a flow diagram of a method of monitoring usage of a patient medical support system.

FIG. 23 depicts anonymization of patient records.

FIG. 24 is a flow diagram of a method of monitoring usage of a patient medical support system.

FIG. 25 is a flow diagram of a method of monitoring usage of a patient medical support system.

FIG. 26 is a flow diagram of a method of monitoring usage of a patient medical support system.

FIG. 28 is a flow diagram of a method of monitoring usage of a patient medical support system.

FIG. 29 is a flow diagram of a method of monitoring usage of a patient medical support system FIG. 31 is a flow diagram of a method of monitoring usage of a patient medical support system.

FIG. 32 is a flow diagram of a method of monitoring usage of a patient medical support system.

FIG. 33 is a flow diagram of a method of monitoring usage of a patient medical support system.

FIG. 34 is a flow diagram of a method of monitoring usage of a patient medical support system.

FIG. 35 is a flow diagram of a method of monitoring usage of a patient medical support system.

FIG. 36 illustrates an article of manufacture including non-transitory machine readable data storage media bearing one or more instructions.

FIG. 37 illustrates an article of manufacture including non-transitory machine readable data storage media bearing one or more instructions.

FIG. 38 illustrates an article of manufacture including non-transitory machine readable data storage media bearing one or more instructions.

DETAILED DESCRIPTION

Figure 1:
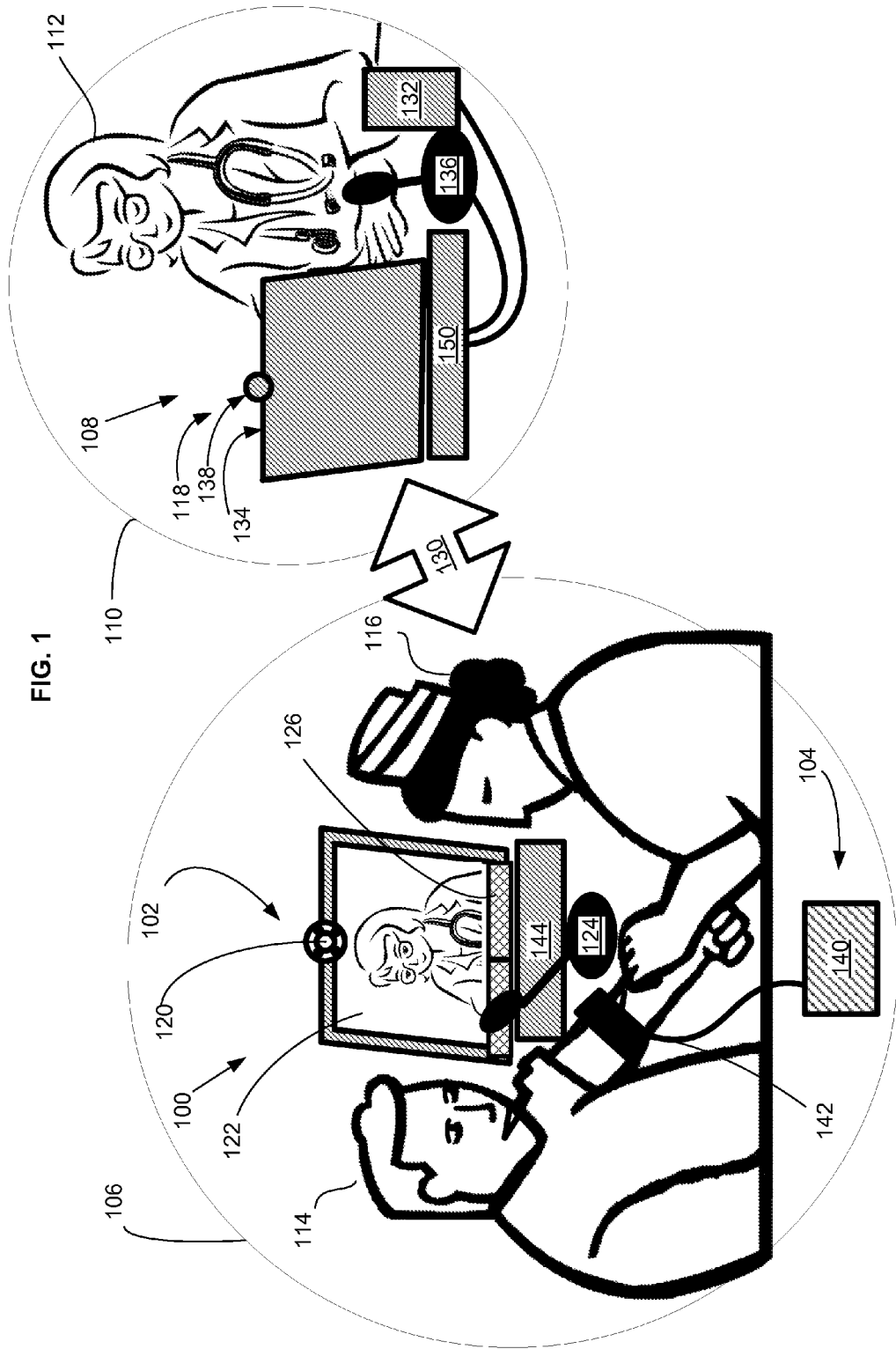
FIG. 1 is an illustration of an embodiment of a patient medical support system and associated medical support monitoring system.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 depicts an example of a patient medical support system 100 that includes a telepresence system 102 and an article of medical equipment 104 at a patient location 106, used in combination with a medical support monitoring system 108 at a remote location 110. Patient medical support system 100 and medical support monitoring system 108 work in cooperation to track and document usage of patient medical support system 100. Patient medical support system 100 tracks the amount and type of usage of the patient medical support system 100 and transmits information regarding the amount and type of usage to a remote monitoring location 110. Remote monitoring system 110 may reside at a hospital or other central monitoring location. Remote monitoring system 110 cooperates with patient medical support system 100 to provide communication between personnel at a monitoring location (e.g. a medical care provider 112) and patient 114 and/or caregiver 116 at a patient location 106 (e.g., the patient's home) via a telemedicine system including telepresence system 102 at patient location 106 and telepresence system 118 at remote monitoring location 110. The telemedicine system may provide for audiovisual or other communication between the monitoring location 110 and patient location 106, which may be provided in combination with medical monitoring or treatment provided with one or more associated article of medical equipment 104. Telemedicine methods and systems are used, for example, in situations where a patient needs or would benefit from medical monitoring, treatment and consultation with a doctor, nurse, or other medical caregiver but is unable to safely or conveniently travel to a medical care facility for the monitoring, treatment, or consultation, or in situations where it is preferable for the patient to stay at home rather than stay at a hospital or other facility at which medical monitoring, treatment or consultation would typically be provided. Use of telemedicine systems allows medical care to be provided in remote locations where medical caregivers are unavailable, and allows patients to receive medical monitoring, treatment, and consultation from home or another suitable location rather than in the hospital. Thus, patients may be discharged from the hospital sooner after treatment, or remain at home longer before being brought to the hospital or other care facility. In the present example, patient medical support system 100 is provided to patient 114 to allow for both telemedicine consultation with medical care provider 112 and use of medical equipment 140 while the patient is at home, but under the care of medical care provider 112. Medical support monitoring system 108 tracks the amount and type of usage of telepresence system 102 and/or associated medical equipment 104. Tracked information regarding usage of patient medical support system 100 may be used for various purposes, including billing, quality assurance, and data analytics, including individual or population studies of usage patterns, for example. Usage information may be linked to identity of patient, caregiver, or equipment used, or anonymized, depending upon the intended use.

In the example of FIG. 1, telepresence system 102 includes a video camera 120 (e.g., a webcam) mounted on display 122, microphone 124, and speaker 126 (built into display 122). Microphone 124 receives a voice input from patient 114 and/or caregiver 116, while video camera 120 receives a video input of patient 114 and/or caregiver 116. As used herein, receiving a communication from a user may include capturing at least one still or moving image of a user, where the image provides any or all of information regarding the user's presence, location, identity, posture, gestures or other movements, health state or condition, facial expression, etc. Voice and image signals from telepresence system 102 are transmitted to telepresence system 118 at remote monitoring location 110 via communication link 130, where they are presented to medical care provider 112 via a speaker 132 and display 134, respectively. Similarly, voice and image signals from medical care provider 112 may be captured by microphone 136 and camera 138, respectively, and transmitted to patient location 106. For example, speaker 132, display 134, microphone 136 and camera 138 may be associated with a computer 150.

In the example of FIG. 1, one article of medical equipment 104 is shown: a blood pressure monitoring device 140 including a cuff 142. Blood pressure monitoring device 140 may communicate with electrical control circuitry 144 via either a wired or a wireless connection, without limitation. Patient blood pressure data, device status and/or operational mode data are transmitted to electrical control circuitry 144 from blood pressure monitoring device 140, while instructions (e.g. to set device parameters and/or start blood pressure measuring are transmitted from electrical control circuitry 144 to blood pressure monitoring device 140. Blood pressure monitoring device 140 may also include controls that allow a user (e.g. caregiver 116) to set various parameters or otherwise control aspects of operation of blood pressure monitoring device 140. Usage of blood pressure monitoring device 140 is determined and details of the usage tracked. For example, each time a blood pressure measurement is made, the time and date of the measurement is stored by electrical control circuitry 144, and the number of blood pressure measurements, as well as the time and data of the measurements is sent to remote monitoring location 108. In addition, the usage of telepresence system 102 may be tracked (including any or all of tracking the number of times communication is attempted or established with telepresence system 118 at remote monitoring location 110, the amount of time spent communicating with telepresence system 118, or the identity of the party initiating the communication, for example). For example, caregiver 116 may be a home healthcare nurse who has a regularly scheduled daily visit with patient 114, during which the patient's blood pressure is measured and patient 114 and caregiver 116 speak to medical care provider 112. A hospital through which the service is provided may charge a fixed fee for a routine visit by caregiver 116, which includes a blood pressure measurement and scheduled consultation with medical care provider 112. If patient 114 wishes to speak to medical care provider 112 outside the regularly scheduled time, the patient may request such a consultation via patient medical support system 100 (e.g., by activating telepresence system 118 by activating a hard or soft button or switch associated with electrical control circuitry 144, etc.) but an additional fee may be charged, which may include a fixed base fee plus an additional per-minute charge for the time spent on the consultation. The per-minute charge may differ depending on the identity of the medical care provider providing the consultation; a consultation with a nurse practitioner may be charged at a different rate than a consultation with a medical doctor, and charges for different medical care providers may differ depending upon experience, specialty, etc.

Figure 2:
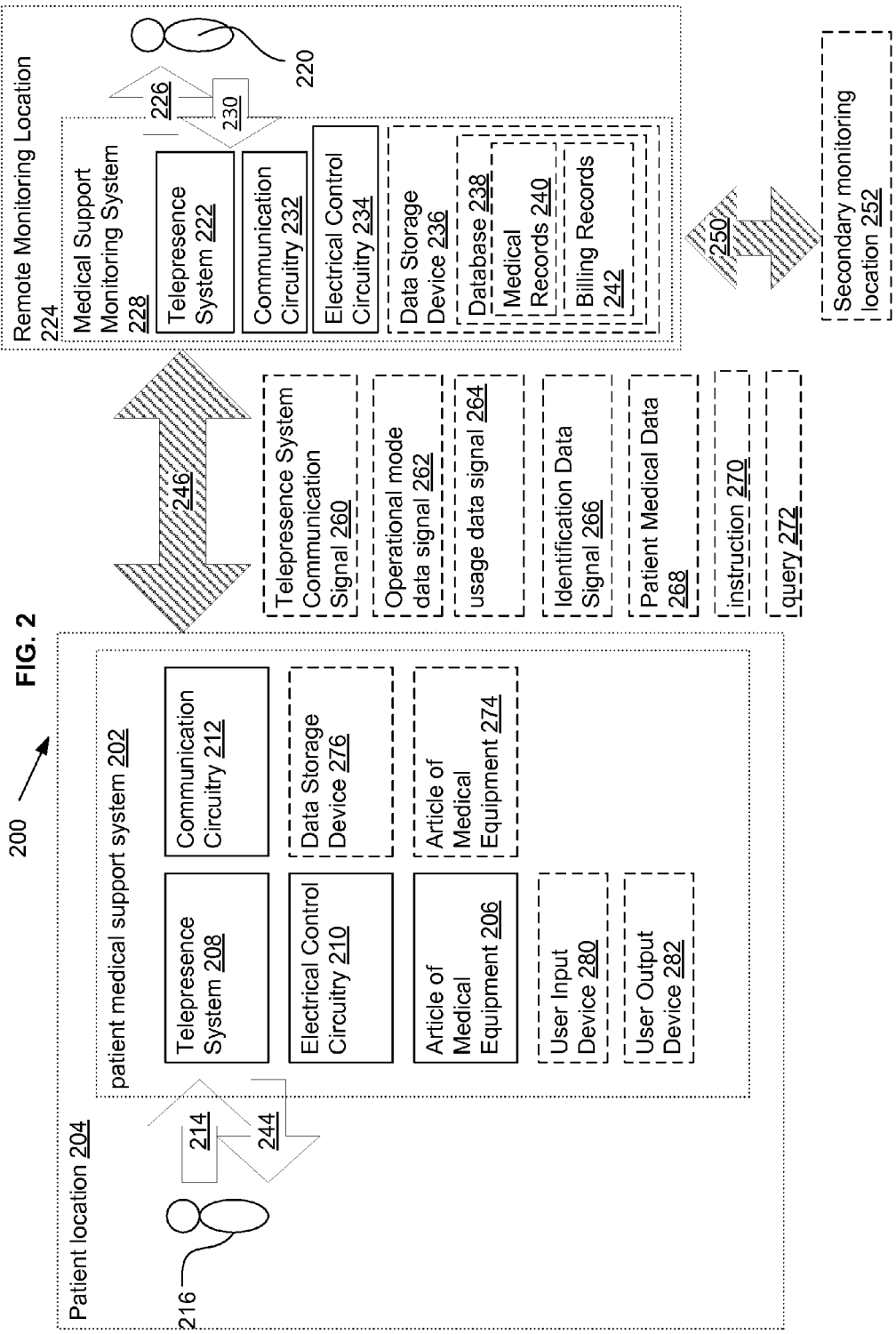
FIG. 2 is a system block diagram of a patient medical support system and associated medical support monitoring system.

FIG. 2 is a block diagram of generalized telemedicine system 200 of which the system depicted in FIG. 1 is an example. In this and other figures, dashed lines indicate optional or alternative components. FIG. 2 depicts patient medical support system 202 at patient location 204 that includes at least one article of medical equipment 206, a telepresence system 208, electrical control circuitry 210, and communication circuitry 212. Telepresence system 208 accepts communication 214 from user 216, and provides for two-way communication between user 216 at patient location 204 and a user 220. User 216 may be, for example, a patient or a caregiver providing medical care and/or assistance to the patient. User 220 is a user of a second telepresence system 222 at remote monitoring location 224. User 220 may be medical care provider, including but not limited to a physician, a nurse, or a medical assistant, for example. Telepresence system 222 at remote monitoring location 224 presents a communication 226 (originating from user 216) to user 220. Telepresence system 222 also accepts communication 230 from user 220.

Second telepresence system 222 forms a part of medical support monitoring system 228. In addition to medical telepresence system 222, medical support monitoring system 228 includes other components, such as communication circuitry 232 and electrical control circuitry 234. Medical support monitoring system 228 may also include, or be associated with, data storage device 236. Electrical control circuitry 210 and 234 may include, but are not limited to, electronic hardware, software, and firmware. Electrical control circuitry 210 and 234 may include micro-processor-based devices, including special-purpose devices, or general purpose computing devices configured with appropriate software. Electrical control circuitry 234 at remote monitoring location system may include computing devices and systems that form a part of or are configured to work in connection with hospital computing or information systems, for example. Medical support monitoring system 228 may include, or be configured to communicate with or operate in connection with one or more data storage devices 236, which may store database 238, including, for example, medical records 240 or billing records 242. In addition, medical support monitoring system 228 may be configured to communicate (via communication link 250) with a secondary monitoring location 252. Secondary monitoring location 252 may be, for example, a location associated with a medical care-providing entity (a hospital, a clinic, etc.) or with a service provider associated therewith (e.g., insurance, billing, documentation, compliance monitoring, data analysis, records management, etc.).

As noted above, telepresence system 222 presents communications 226 originating from user 216 at patient location 204 to user 220 at remote monitoring location 224, and receives communications 230 from user 220. Similarly, telepresence system 208 accepts communications 214 from user 216, and presents communications 244 originating from user 220 to user 216. Telepresence system 208 provides for transmission of communications from user 214 via communication circuitry 212 and communication circuitry 228 to telepresence system 222. Communication circuitry 212 and communication circuitry 228 work together to establish two-way communication link 246. Communication circuitry 212 is configured to receive the communication from the second user via two-way communication link 246. Two-way communication link 246 may be used, e.g., for remote consultation, asking and answering of questions, offering of medical advice and instructions, etc. Communications between users 216 and 220 may include, but are not limited to, audio and visual communications, for example.

Two-way communication link 246 may carry a variety of communication and data signals between patient medical support system 202 and medical support monitoring system 228, including but not limited to one or more telepresence system communication signal 260, operational mode data signal 262, usage data signal 264, identification data signal 266, patient medical data 268, instruction 270, and query 272, as will be described in greater detail herein. Usage, operational mode, and identification data signals may pertain to the patient medical support system 202 as a whole, or may pertain specifically to a telepresence system (e.g. telepresence system 208 or telepresence system 222), or one or more article of medical equipment. FIG. 2 depicts article of medical equipment 206 and article of medical equipment 274, but it will be appreciated that, in various aspects, one, two, or multiple articles of medical equipment may be used, without limitation. Furthermore, a single article of medical equipment may be capable of performing a single function (e.g. detecting blood pressure), or may be capable of performing multiple functions (e.g detecting blood pressure, heart rate, and blood oxygenation). Various device control signals, data signals, instructions, status signals, and the like may be transmitted between medical support monitoring system 228 and patient medical support system 202 other than those explicitly recited herein.

In a general sense, those skilled in the art will recognize that the various embodiments described herein can be implemented, individually and/or collectively, by various types of electrical circuitry having a wide range of electrical components such as hardware, software, firmware, and/or virtually any combination thereof. Electrical circuitry (including electrical control circuitry 210 and electrical control circuitry 234 depicted in FIG. 2, for example) includes electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device, which may include various types of memory (e.g., random access, flash, read only, etc.)), electrical circuitry forming a communications device (e.g. communication circuitry 212 or 230) (e.g., a modem, communications switch, optical-electrical equipment, etc.), and/or any non-electrical analog thereto, such as optical or other analogs (e.g., graphene based circuitry). In a general sense, those skilled in the art will recognize that the various aspects described herein which can be implemented, individually and/or collectively, by a wide range of hardware, software, firmware, and/or any combination thereof can be viewed as being composed of various types of "electrical circuitry."

Those skilled in the art will recognize that at least a portion of the devices and/or processes described herein can be integrated into a data processing system. Those having skill in the art will recognize that a data processing system generally includes one or more of a system unit housing, a video display, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems. In an aspect, patient medical support system 202 includes at least one data storage device 276, which may include any sort of memory or other data storage element or device included in or used in connection with patient medical support system 202, to store data at first location 204. In an aspect, patient medical support system 202 includes one or more user input device 280 to permit user 216 to control various aspects of operation of patient medical support system 202. User input device can also be used to receive input of other information from the user, either user-initiated or in response to a query. For example, a patient may be asked to provide inputs in response to questionnaires, tests of user ability or condition (e.g. test of vision, cognitive skills, motor skills, etc.) User input device 280 can include various types of user input devices or controls as are well known to those of ordinary skill in the art, including but not limited to keyboards, touchpads, touchscreen, mouse, joystick, microphone, buttons, or switches. User input devices may be designed to interface directly with a patient's nervous system or track a patient's muscular activity or correlates thereof, including a brain-computer interface, EEG or EMG sensors, motion tracking devices (such as a Kinect sensor) or one or more camera (e.g. a video camera) used in combination with appropriate image-analysis hardware/software, eye tracking devices etc. Switches may includes those activatable by sipping or puffing air through a tube, for use by patients with limited mobility or muscle strength. Patient medical support system 202 may also include one or more user output devices 282, for providing information or feedback to a user, including video, graphic, or text displays, indicator lights, seven-segment displays, gauges, strip charts, auditory alarms, buzzers, voice outputs, tactile, haptic, or braille displays, electrical or magnetic stimulation devices, etc.

Figure 3:
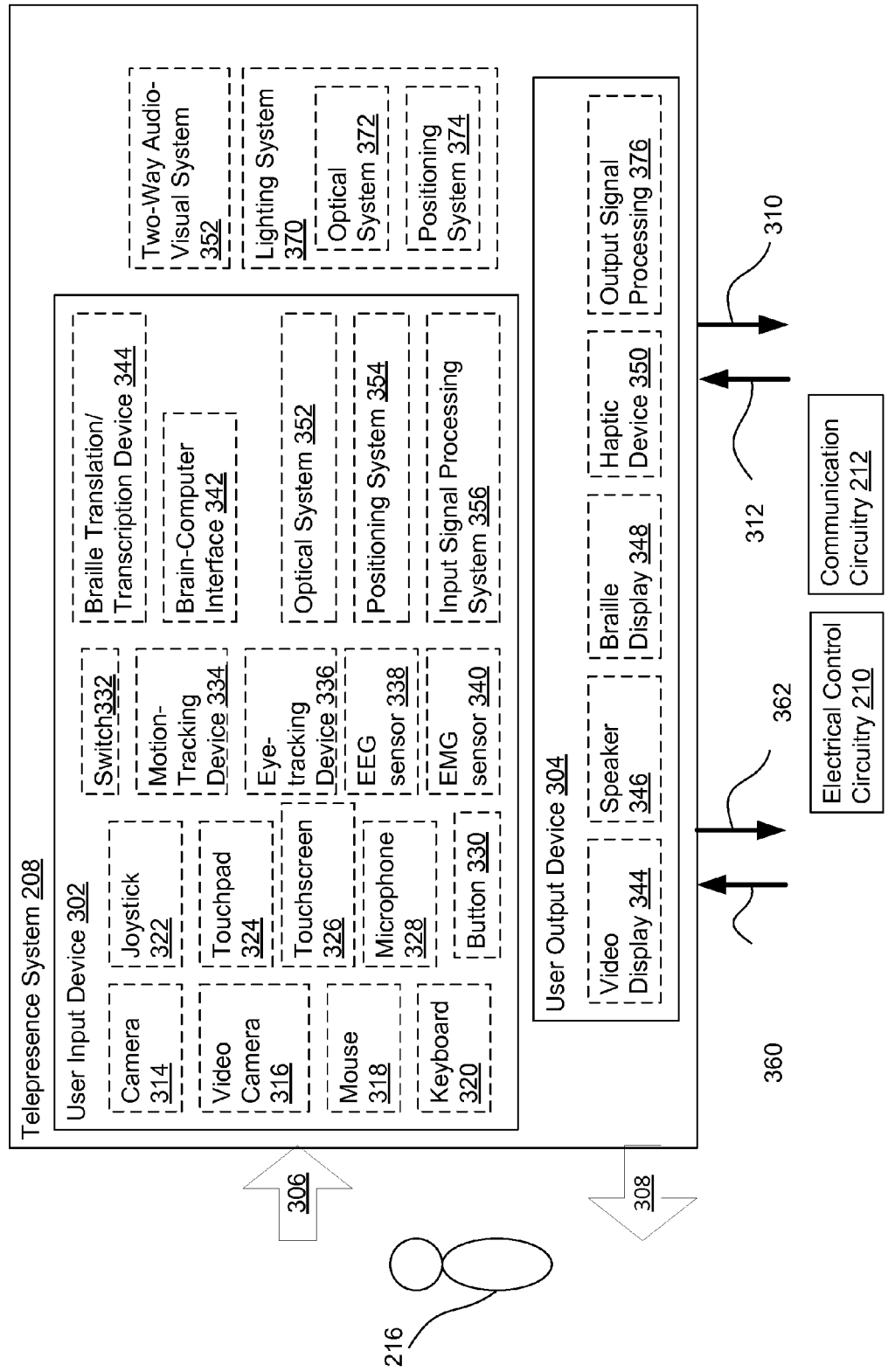
FIG. 3 is a block diagram of portion of a telepresence system used in a patient medical support system.

FIG. 3 is a block diagram of a telepresence system 208 located at a patient location, as shown generally in FIG. 2. Telepresence system includes at least one user input device 302 and at least one user output device 304. User input device 302 is adapted to accept a communication 306 from a first user of the patient medical support system (e.g., a patient or caregiver, as discussed herein above). User output device 304 is adapted to present a communication 308 to the first user. Communication 308 is a communication that was received from a second user at the monitoring location, for example. Communication signal 310 from user input device 302 is transmitted to electrical control circuitry 210 and/or communication circuitry 212 (as depicted and described in connection with FIG. 2) for transmittal to a second telepresence system at a remote monitoring location via a communication link. Communication signals 312 originating from the remote monitoring location are provided to the telepresence system 208 via communication circuitry 212.

In an aspect, at least one user input device 302 includes at least one of a camera 314, a video camera 316, a mouse 318, a keyboard 320, a joystick 322, a touchpad 324, a touchscreen 326, a microphone 328, a button 330, a switch 332, a motion-tracking device 334, an eye tracking device 336, an EEG sensor 338, and EMG sensor 340, a brain-computer interface 342, and a braille translation/transcription device 344.

In an aspect, at least one user output device 304 includes at least one of a video display 344, a speaker 346, a braille display 348, and a haptic device 350.

In an aspect telepresence system 208 includes a two-way audiovisual system 352, of which user input device 302 and user output device 304 may be components. In an aspect, telepresence system 208 includes at least one of a microphone (e.g. microphone 328), a speaker (e.g. speaker 346), a video display (e.g. video display 344), and a camera (e.g. camera 314).

User input devices and user output devices of telepresence system 208 may be configured as separately packaged devices configured to communicate with electrical control circuitry 210 via a wired connection (via a plug and jack or USB, for example) or wireless connection, or they may be built into or packaged with other system components. One or multiple user input devices or output devices may be used, and they may be of the same or different types. For example, a conventional commercially available video camera suitable for video conferencing can be used for audio/visual communication between patient and medical care provider. In an aspect, the camera for audio/visual communication between patient and medical care provider may also provide medically useful information. In an aspect, a camera may function as an article of medical equipment. In an aspect, two or more cameras may be used to provide views of the subject from two or more different angles or positions. In an aspect, a specialized camera may be used to obtain images for medical diagnostic purposes. For example, a specialized camera may produce images at a particular wavelength or range of wavelengths of light, have a higher spatial resolution or higher frame rate, or have other characteristics that permit it to obtain medically useful information, for example as described in U.S. Patent Publication 20120307056 dated Dec. 6, 2012 to Zuzak et al., and U.S. Patent Publication 201230128223 dated May 23, 2013 to Wood, each of which is incorporated herein by reference. In an aspect, telepresence system 208 may include one or more photocell, charge-coupled device, scanner, 3D scanner, 3D imager, camera, single pixel camera, a visual camera, IR camera, a stereoscopic camera, a digital camera, a video camera, and a high speed video camera, for example. One or more digital images of the skin surface of the subject for use in generating a digital three-dimensional representation of the skin surface can be acquired from one or more of a digital camera or scanning device. For example, two video cameras, slightly apart, can be used to image the same portion of skin surface of the individual in a process termed stereophotogrammetry. For example, a single camera can be used to take multiple images under different lighting conditions or from different positions. In an aspect, the topography of the skin surface of an individual can be acquired in a point-cloud format using a three-dimensional sensing system consisting of two or more digital cameras and one or more projectors connected to a personal computer. The camera position and shutter can be adjusted to the body region, which is exposed to structured light, allowing for optical representation of the surface by a cloud of up to 300,000 points in three-dimensional coordinates (see, e.g., Feng et al., *Br. J. Oral Maxillofac. Surg.* (2010) 48:105-109, which is incorporated herein by reference). In some embodiments, the combination of stereophotogrammetry and 3D laser scanner techniques can be combined to generate a three-dimensional model of the skin surface of an individual (see, e.g., Majid, et al. *International Archives of the Photogrammetry, Remote Sensing and Spatial Information Science*. Vol. XXVII. Part B5. (2008) 805-811; Markiewicz & Bell, *Facial Plast. Surg. Clin. N. Am.* (2011) 19:655-682; van Heerbeek et al., *Rhinology* (2009) 47:121-125, which are incorporated herein by reference). Scanners for scanning head, face and/or whole body are commercially available (from, e.g., Cyberware, Monterery Calif.; Accurex Measurement Inc., Swathmore, Pa.; 3dMD Atlanta, Ga.; Konica/Minolta, Ramsey, N.J.). In an aspect, user input device 302 includes optical system 352, which may include one or more components such as reflectors, filters, lenses, or shutters, which may be used to control various aspects of an image detected by user input device 302. In an aspect, user input device 302 includes a positioning system 354 including positioning components for adjusting and/or controlling the position, e.g. of camera 314 or video camera 316 in order to obtain a desired input. In an aspect, user input device 302 includes input signal processing system 356 for performing filtering, amplification, and/or other processing of inputs received by user input device 302. In an aspect, optical system 352, positioning system 354, and/or input signal processing system 356 are controlled by electrical control circuitry 210. Filtration, pan, tilt, or zoom may be controlled by adjustment of these and/or other controllable components, for example.

In an aspect, telepresence system 208 includes a lighting system 370 which provides light during imaging of the subject, e.g., by camera 314 or video camera 316, or other imaging devices or systems used in the telepresence system. Lighting system 370 may include one or more light sources. Lighting system 370 may also include optical system 372, which may include components of the types described in connection with optical system 352, e.g. for adjusting filtration of light produced by lighting system 370. In an aspect, lighting system 370 includes positioning system 374 for adjusting or controlling the position of one or more components of lighting system 370 and the aiming of light produced thereby.

In an aspect, user output device 304 includes output signal processing 376, for processing the output of user output device 304 prior to presentation of output 308 to user 216 as known by those having skill in the art, e.g. to provide amplification, filtration, or filtering of the signals produced by user output device 304.

In an aspect, an operational mode of the telepresence system is set by telepresence system operational mode command signal 360, which is transmitted to telepresence system 208 from electrical control circuitry 210. In an aspect, telepresence system operational mode signal 362, which contains information regarding the operational mode of telepresence system 208, is transmitted to electrical control circuitry 210 from telepresence system 208. The operational mode of the telepresence system may include one or more of the following: turned on, turned off, standby, audio communication, video communication, send communication, receive communication. The operational mode of the telepresence system may be medical care provider-initiated (e.g., use of the telepresence system was initiated in response to a signal originating from the medical support monitoring location at the remote location), or user-initiated (e.g., use of the telepresence system was initiated by a user at the patient location issuing a command to the system via a user input device forming a part of the patient medical support system). Other telepresence system operational modes may apply, depending on the number and type of components forming telepresence system 208, and the operational mode is not limited to the specific examples of operational modes listed above. It will be appreciated that telepresence system operational mode may include one or more operational modes; for example, the telepresence system may be turned on, sending one or both of audio and visual communications, and operating in a user-initiated mode (in response to a user input).

Figure 4:
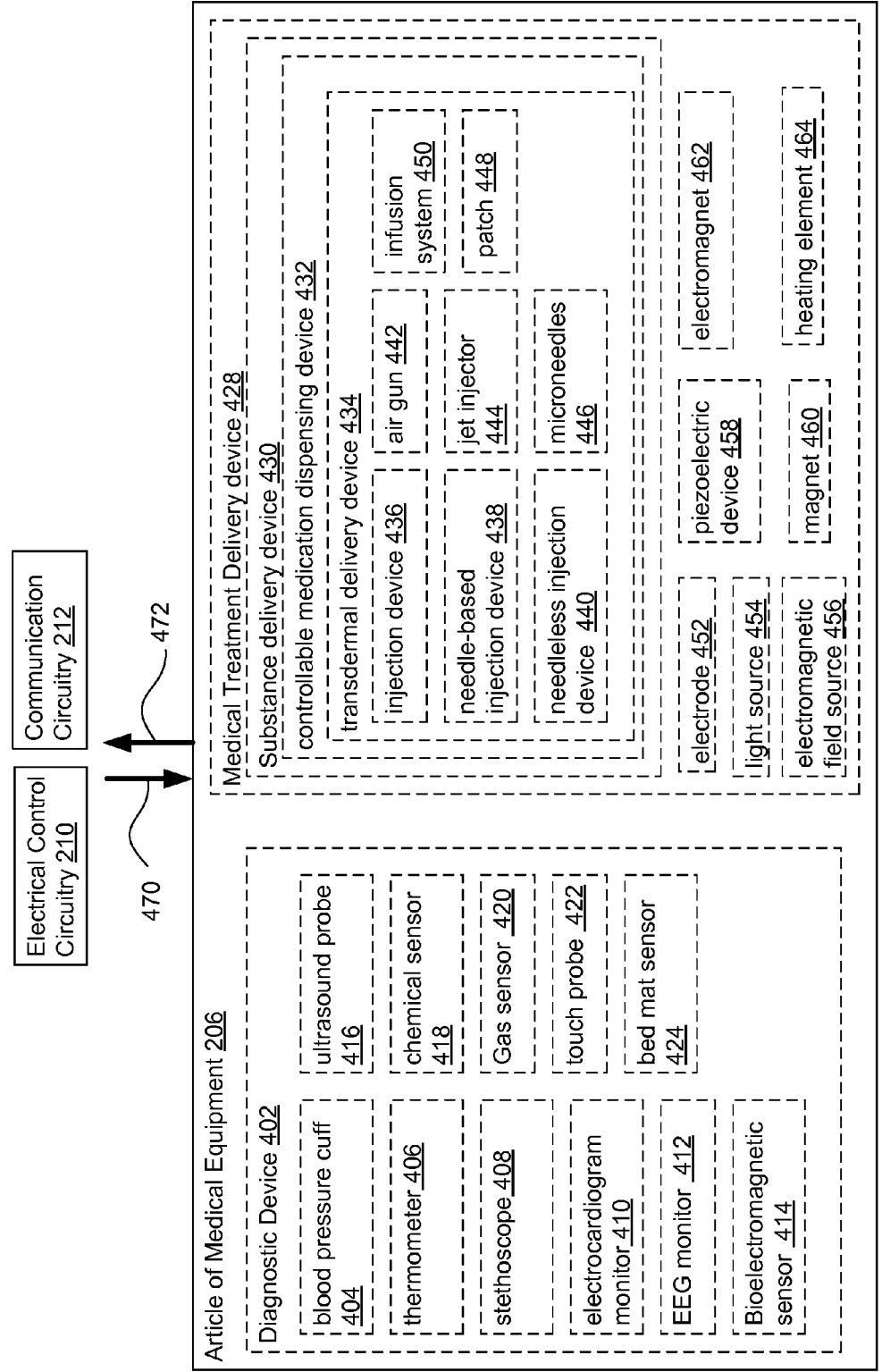
FIG. 4 is a block diagram of medical equipment used in connection with a patient medical support system.

FIG. 4 is a block diagram of an article of medical equipment 206, as shown generally in FIG. 2. Article of medical equipment 206 may include a diagnostic device 402, or a medical treatment delivery device 428.

Diagnostic device 402 may include, for example, one or more of a blood pressure cuff 404, a thermometer 406, a stethoscope 408, an electrocardiogram (ECG) monitor 410, an electroencephalogram (EEG) monitor 412, a bioelectromagnetic sensor 414 for sensing one or more bioelectric or biomagnetic signals (including but not limited to electroencephalogram, electrocardiogram, electromyogram, electrooculogram, magnetic counterparts thereof), an ultrasound probe 416, a chemical sensor 418 (e.g. for measuring chemicals or gases in bodily fluids in samples taken from the body or within the body, including but not limited to blood, plasma, serum, saliva, urine, mucus, tears, semen, and vaginal secretions), a gas sensor 420 (for measuring blood gases, expired gases, flatus, etc.) a touch probe 422, or a bed mat sensor 424.

In an aspect, article of medical equipment 206 includes medical treatment delivery device 428, which may be, for example, a substance delivery device 430, e.g. controllable medication dispensing device 432 configured to dispense at least one formulated medication in response to a control signal from the first electrical control circuitry 210. Controllable medication dispensing device 432 may be, for example, a pill dispenser of the type described in U.S. Pat. No. 8,452,446 issued May 28, 2013 to Madras et al., which is incorporated herein by reference, or other device configured to dispense pills, capsules, powders, liquids, inhalants, and other oral medications or inhalable medications. A medication dispenser may also deliver formulated medications for topical delivery, such as creams, ointments, eye drops, etc. In an aspect, medical treatment delivery device 428 includes a transdermal substance delivery device 434, including for example, one or more of an injection device 436, a needle-based injection device 438 (e.g. as described in U.S. Pat. No. 6,056,716 issued May 2, 2000 to D'Antonio et al. and U.S. Pat. No. 8,544,645 issued Oct. 1, 2013 to Edwards et al., both of which are incorporated herein by reference), a needleless injection device 440, an air gun 442, a jet injector 444, microneedles 446, a patch 448, or an infusion system 450 configured to deliver an infusible substance (e.g., of the type described in U.S. Pat. No. 8,348,885 issued Jan. 8, 2013 to Moberg et al., which is incorporated herein by reference). In other aspects, medical treatment delivery device 428 may be configured to deliver other types of treatments to the subject, for example, including delivery of various forms of energy (light, electrical, magnetic, electromagnetic, acoustic, ultrasonic, thermal), pressure, vibration, or cooling (i.e., removal of energy), to produce various therapeutic effects in the subject. Medical treatment delivery device 428 may include one or more electrode 452, light source 454, electromagnetic field source 456, piezoelectric device 458, magnet 460, electromagnet 462, or heating element 464, for example.

In an aspect, an operational mode of article of medical equipment 206 is set by medical equipment operational mode command signal 470, which is transmitted to article of medical equipment 206 from electrical control circuitry 210. In an aspect, medical equipment operational mode signal 472, which contains information regarding the operational mode of article of medical equipment 206, is transmitted to electrical control circuitry 210 from article of medical equipment 206. The operational mode of the article of medical equipment may include one or more of the following: turned on, turned off, standby, patient data gathering, treatment delivery, error (indicating a device malfunction or faulty state, for example), or data transmission (e.g. of patient data or device status data), for example. Other medical equipment operational modes may apply, and the operational mode is not limited to the specific examples of operational modes listed above. It will be appreciated that article of medical equipment operational mode may include one or more operational modes; for example, the article of medical equipment may be turned on, and also delivering a treatment to a patient.

Figure 5:
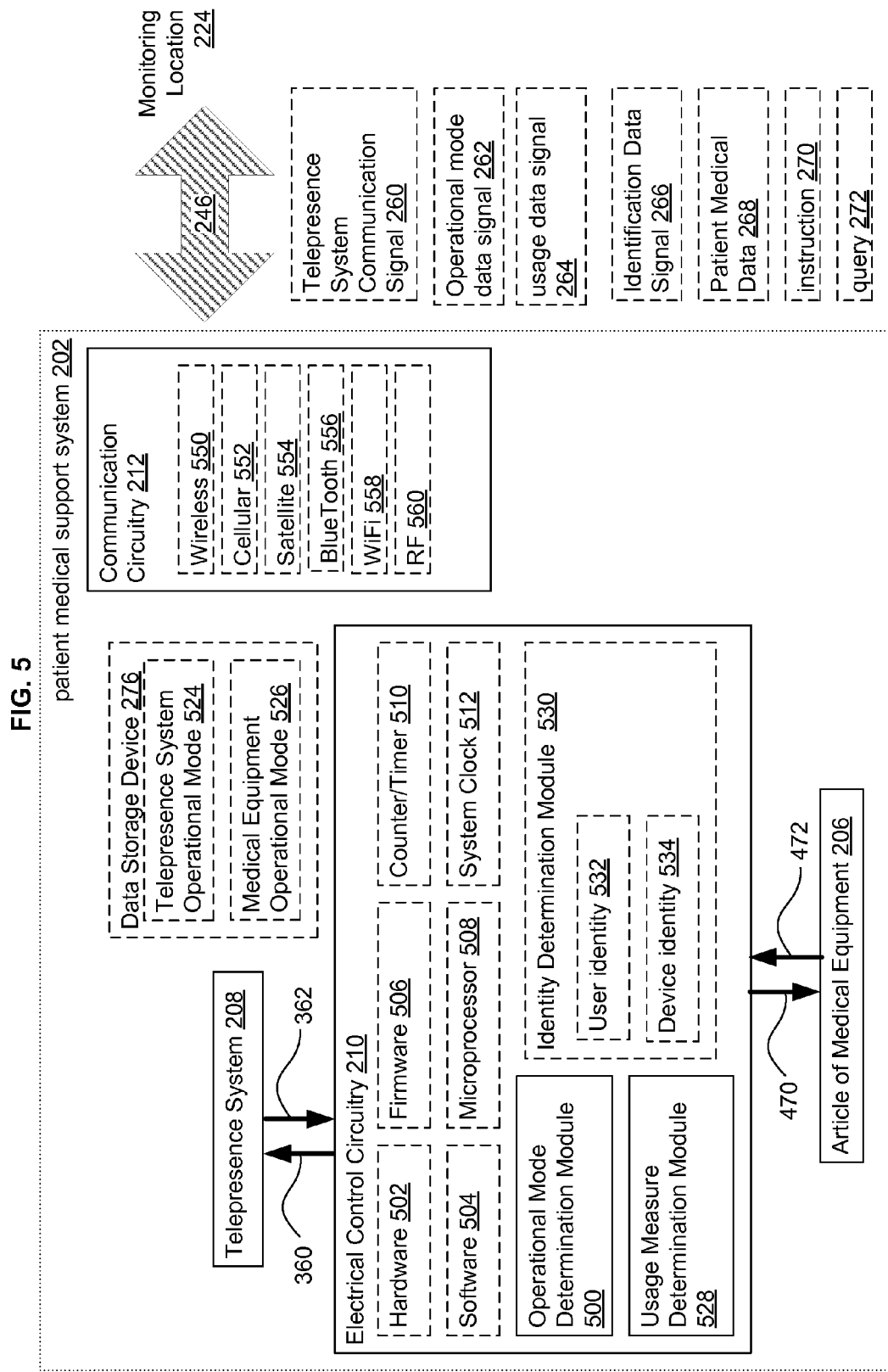
FIG. 5 is a block diagram of control and communication circuitry used in a patient medical support system.

FIG. 5 is a block diagram illustrating electrical control circuitry 210 and communication circuitry 212 of patient medical support system 202.

In an aspect, electrical control circuitry 210 includes one or more of hardware 502, software 504, firmware 506, and a microprocessor 508. Electrical control circuitry 210 may include or consist entirely of application-specific hardware, software, and/or firmware (e.g., an application-specific microprocessor based device), or electrical control circuitry 210 may include a general purpose computing device configured with and/or used in combination with appropriate software and/or hardware (e.g., as depicted in FIG. 1). In an aspect, electrical control circuitry 210 includes a general purpose computing device configured with appropriate software used in combination with separately packaged application-specific electrical circuitry.

In an aspect, electrical control circuitry 210 includes operational mode determination module 500, which is used to determine one or more operational modes of patient medical support system 202. The operational mode of patient medical support system may include, for example, one or more operational modes of telepresence system 208 (e.g. telepresence system operational mode 524) and one or more operational modes of at least one article of medical equipment 206 (e.g., medical equipment operational mode 526). Medical equipment operational mode 526 and telepresence system operational mode 524 may be determined by the electrical control circuitry (e.g. by operational mode determination module 500) based on stored information regarding instructions or control signals sent to the medical equipment and/or telepresence system by the electrical control circuitry (e.g., medical equipment operational mode command signal 470 or telepresence system operational mode command signal 360), or by reading device status from the medical equipment and/or telepresence system connected to the electrical control circuitry (e.g., medical equipment operational mode signal 472 or telepresence system operational mode signal 362, as shown in FIG. 5). Information regarding the operational modes may be stored in data storage device 276.

In an aspect, electrical control circuitry 210 is configured to determine a first medical support system operational mode from at least two different operational modes of the patient medical support system, and determine a first medical support system usage data signal indicative of an amount of usage of the patient medical support system in the first medical support system operational mode. In an aspect, electrical control circuitry 210 is configured to determine the first medical support system operational mode at least in part by determining a medical equipment operational mode from at least two different operational modes of the at least one article of medical equipment, and determine the first medical support system usage data signal at least in part by determining a medical equipment usage data signal indicative of an amount of usage of the at least one article of medical equipment in the medical equipment operational mode. In connection therewith, communication circuitry 212 is configured to transmit the medical equipment operational mode and the medical equipment usage data signal to the monitoring location.

In an aspect, electrical control circuitry 210 is configured to determine the first medical support system operational mode by determining a telepresence system operational mode from at least two different operational modes of the first telepresence system and determine the first medical support system usage data signal by determining a telepresence system usage data signal indicative of an amount of usage of the first telepresence system in the first telepresence system operational mode. In addition, the communication circuitry is configured to transmit the first telepresence system operational mode and the first telepresence system usage data signal to the monitoring location.

In an aspect, electrical control circuitry 210 includes counter/timer 510, which is used in the determination of usage of patient medical support system 202, including usage of telepresence system 208 and article of medical equipment 206. Usage measure determination module 528 includes or makes use of counter/timer 510 and/or system clock 512. Counter/timer may be a programmable counting/timing device, for example. In an aspect, when an operational mode of patient medical support system 202 (or a component thereof) changes, as determined by operational mode determination module 500, the time at which the operational mode changes is tracked, by storing an absolute or relative time measure or counter value (e.g. in data storage device 276), or by resetting a count or time in counter/timer 510. When the operational mode of patient medical support system 202 (or the component thereof) changes again, the time at which the change occurred may again be tracked, by storing an absolute or relative time measure or counter value, or by resetting a count or time in counter/timer 510. In an aspect, start of usage, end of usage, duration, or number of usage events are determined using techniques well known to those having ordinary skill in the art.

In an aspect, identity determination module 530 is used to determine a user identity 532 of a user at the patient location. The identity of the user may be stored or pre-programmed into the electrical control circuitry (e.g., stored in data storage device 276), or determined by prompting the user or a representative of the user (e.g., via user output device 282, shown in FIG. 2) to enter a username, identification number, etc. associated with the user via a user input device (e.g., user input device 280, shown in FIG. 2). Alternatively, or in addition, the identity of the user may be determined by various types of biometric techniques, such as facial recognition, retinal scan, etc., by entry of a password or use of a key.

In an aspect, identity determination module 530 is used to determine a device identity 534 indicative of an identity of at least a portion of the patient medical support system. Device identity 534 may represent the identity of telepresence system 208, article of medical equipment 206, electrical control circuitry 210, communication circuitry 212, or other portions, parts, or components of the patient medical support system, for example. Identities of systems, parts, component types, or specific components may be stored in data storage device 276, or may be determined by the electrical control circuitry 210 by reading device status from the devices or components of patient medical support system 202.

As discussed in connection with FIG. 2, communication circuitry 212 in patient medical support system 202 and communication circuitry 232 in medical support monitoring system 228 are configured to provide a communication link 246 between the two locations. As shown in FIG. 5, in an aspect, communication circuitry 212 is adapted to provide at least one of WiFi 558, cellular 552, wireless 550, radio frequency 560, satellite 554, and BlueTooth 556 communication. In an aspect, communication link 246 may be a wireless communication link. In an aspect, the communication link 246 may be a cellular communication link. In various aspects, a wireless communication link includes at least one of a radiowave, wireless network, cellular network, satellite, WiFi, Wide Area Network, Local Area Network, or Body Area Network communication link. Communication link 246 may be any of various types of communication links suitable for providing communication between two remote locations. Communication between locations remote from each other may take place over telecommunications networks, for example public or private Wide Area Network (WAN). In general, communication between remote locations is not considered to be suitably handled by technologies geared towards physically localized networks, e.g. Local Area Network (LAN) technologies operation at Layer ½ (such as the forms of Ethernet or WiFi). However, it will be appreciated that portions (but not the entirety) of communication networks used in remote communications may include technologies suitable for use in physically localized network, such as Ethernet or WiFi. In an aspect, system components are considered "remote" from each other if they are not within the same room, building, or campus. In an aspect, a remote system may include components separated by a few miles or more. Conversely, system components may be considered "local" to each other if they are located within the same room, building, or campus.

In an aspect, communication circuitry 212, operating in cooperation with electrical control circuitry 210, is configured to receive telepresence system communication signal 260 including a communication from a user of a telepresence system at the remote monitoring location 224, and transmit telepresence system communication signal 260 containing a communication from a user of patient medical support system 202 to the remote monitoring location 224. In an aspect, communication circuitry 212 is configured to transmit one or more operational mode data signal 262, usage data signal 264 and an identification data signal 266 to monitoring location 224. In a further aspect, communication circuitry 212 is configured to transmit patient medical data 268 (e.g. as may be detected from an article of medical equipment that includes a diagnostic device 402 as shown in FIG. 4) or from patient medical support system 202 to monitoring location 224, and to transmit one or more of instructions 270 or queries 272 from monitoring location 224 to patient medical support system 202.

In an aspect, the communication circuitry 212 is configured to provide wireless communication between at least two system components at the patient location. In an aspect, communication circuitry 212 is configured to provide wired communication between at least two system components at the patient location. System components connected via wired or wireless connections may include, but are not limited to, electrical control circuitry 210, telepresence system 208, one or more article of medical equipment 206, and one or more data storage device 276, for example.

Figure 6:
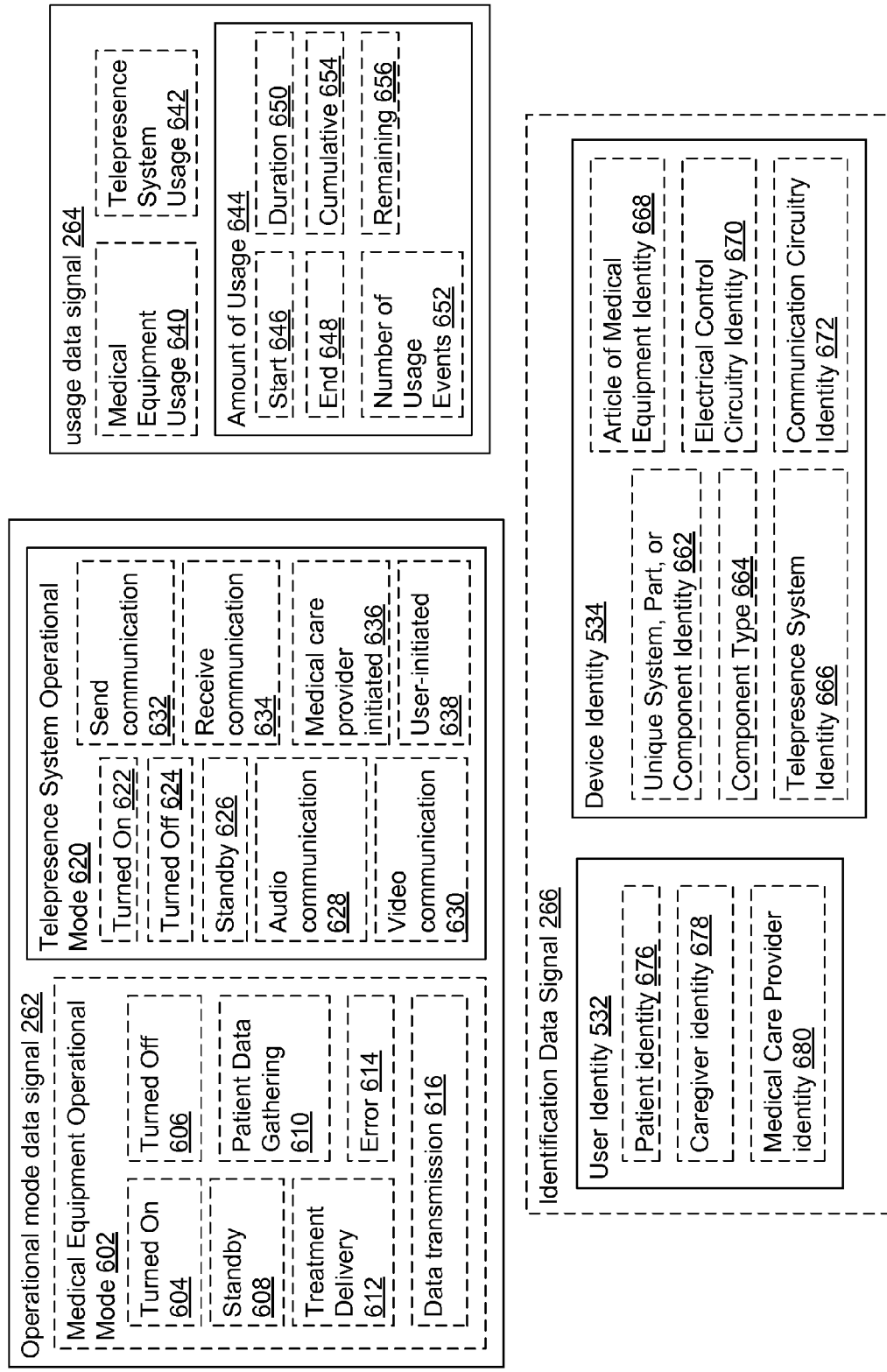
FIG. 6 is a depiction of data signals produced by a patient medical support system.

FIG. 6 illustrates information contained in the various data signals transmitted between patient medical support system 202 and remote monitoring location 224 via communication link 246, including operational mode data signal 262, usage data signal 264, and identification data signal 266.

Operational mode data signal 262 represents the operational mode of one or more of a telepresence system (e.g., telepresence system 208 in FIG. 2) and one or more article of medical equipment (e.g., article of medical equipment 206 and 274, as depicted in FIG. 2). For each article of medical equipment, one or more operational modes may be indicated. Medical equipment operational mode 602 may include, for example, "turned on" 604, "turned off" 606, "standby" 608, "patient data gathering" 610, "treatment delivery" 612, "error" 614, or "data transmission" 616. The specific number and types of operational modes will depend upon the specific article of medical equipment; it will be appreciated that the listed operational modes are only provided as examples, and other medical equipment operational modes may be used. More than one medical equipment operational mode 602 may apply to an article of medical equipment at a particular time; for example, "turned on" and "treatment delivery" apply simultaneously. Similarly, telepresence system operational mode 620 may include, for example, "turned on" 622, "turned off" 624, "standby" 626, "audio communication" 628, "video communication" 630, "send communication" 632, or "receive communication" 634. Additional telepresence system operations modes include "medical care provider initiated" 636 and "user-initiated" 638, representing whether the use of the telepresence system was initiated by the medical care provider, or by a user at the patient location. Again, the number and types of operational modes will depend upon the telepresence system. Other telepresence system operational modes may be used, without limitation. Furthermore, more than one telepresence system operational mode 620 may apply at a particular time. Medical equipment operational mode 602 and telepresence system operational mode 620 may be determined by the electrical control circuitry based on stored information regarding instructions or control signals sent to the medical equipment and/or telepresence system by the electrical control circuitry (e.g., medical equipment operational mode command signal 470 or telepresence system operational mode command signal 360, as shown in FIG. 5), or by reading device status from the medical equipment and/or telepresence system connected to the electrical control circuitry (e.g., medical equipment operational mode signal 472 or telepresence system operational mode signal 362, as shown in FIG. 5).

Identification data signal 266 contains information indicative of one or more of device identity 534 or user identity 532. In an aspect, identification data signal is indicative of an identity of a user at the patient location; for example, in an aspect identification data signal 266 is indicative of patient identity 676. In another aspect, identification data signal 266 is indicative of caregiver identity 678. In an aspect, identification data signal 266 is indicative of an identity of a user at the remote monitoring location; for example, medical care provider identity 680. Identity of the user may be stored or pre-programmed into the electrical control circuitry, or determined during use of the telepresence system, by prompting the user or a representative of the user (e.g., via user output device 282, shown in FIG. 2) to enter a username, identification number, etc. associated with the user via a user input device (e.g., user input device 280, shown in FIG. 2). Alternatively, or in addition, the identity of the user may be determined by various types of biometric techniques, such as facial recognition, retinal scan, etc., by entry of a password or use of a key.

In an aspect, identification data signal 266 is a device identification data signal indicative of a device identity 534 of at least a portion of the patient medical support system. In an aspect, the identification data signal may uniquely identify an individual system, portion, part, or component, as indicated at 662. In another aspect, the identification data signal may identify a type of a component of the patient medical support system, as indicated at 664. For example, the identification data signal may identify that the patient medical support system includes a particular type of medical equipment, such as heart rate monitor. The identification data signal may be indicative of one or more identifications associated with the patient medical support system (e.g., a serial number, a part number, a model number, a manufacturer, a supplier, etc.). In various aspects, identification data signal 266 may be indicative of a device identity of telepresence system 666, article of medical equipment 668, electrical control circuitry 670, communication circuitry 672, or other portions, parts, or components of the patient medical support system, for example. Identities of systems, parts, components, component types, or specific components may be stored in data storage device forming a portion of the electrical control circuitry of the patient medical support system, or it may be determined by the electrical control circuitry by reading device status from individual devices (telepresence system components and/or articles of medical equipment) connected to the electrical control circuitry. As will be described herein below, a device identity may be associated with a user identity when a specific device is assigned to a specific patient, and subsequently the identity of the device may serve to identify the user of the device.

Identification data signal 266 may contain one or multiple identities associated with a particular operational mode of the patient medical support system. For example, a particular usage of the patient medical support system may include the use of a telepresence system, a particular article of medical equipment, one or more user at the patient location (e.g., the patient and the caregiver) and one or more user at the remote monitoring location (e.g., one or more medical care provider). Accordingly, information regarding or indicative of the identity of any or all of these users and system components may be communicated to the remote monitoring location for record keeping and further analysis.

In an aspect, usage data signal 264 represents the amount of usage 644 of the patient medical support system. In an aspect, usage data signal 264 represents medical equipment usage 640, which may include usage of one or more article of medical equipment. In an aspect, usage data signal 264 represents telepresence system usage 642. In an aspect, usage data signal 264 is indicative of an amount of usage of the patient medical support system (or one or more component thereof, e.g. the telepresence system and one or more article of medical equipment) in an operational mode. In an aspect, usage data signal 264 is indicative of a start of usage 646 or an end of usage 648. In another aspect, the usage data signal is indicative of a number of usage events 652 of the patient medical support system (or component(s) thereof) in the operational mode. The information transmitted to the remote monitoring location (e.g. remote monitoring location 224 in FIG. 2) in usage data signal 264 may be combined with other information available at the remote monitoring location in order to determine or derive an amount of usage. If each usage of the patient medical support system takes a fixed amount of time, transmitting start time 646, or number of usage events 652 provides sufficient information to determine the amount of usage at the remote monitoring location. If start time information is already available at the remote monitoring location (e.g., because use of the patient medical support system is initiated by a control signal send from remote monitoring location, or because use of the patient medical support system occurs at regularly scheduled times known at the remote monitoring location), end time information 648 can be used to determine the duration of usage. In an aspect, the usage data signal contains values indicative of an amount of usage that were derived at the patient location before being transmitted to the remote monitoring location, e.g. cumulative usage 654, or remaining usage 656 (e.g., if a pre-set amount of usage is authorized, and after each usage the remaining available usage is reported to the remote monitoring location). Start of usage 646, end of usage 648, duration 650, number of usage events 652 values can be determined at the patient location through the use of, e.g. counter/timer 510 in electrical control circuitry 210, as depicted in FIG. 5, using techniques well known to those having ordinary skill in the art. Derived values (cumulative usage 654 or remaining usage 656) may similarly be determined by electrical control circuitry 210 including properly configured hardware and or software.

Figure 7:
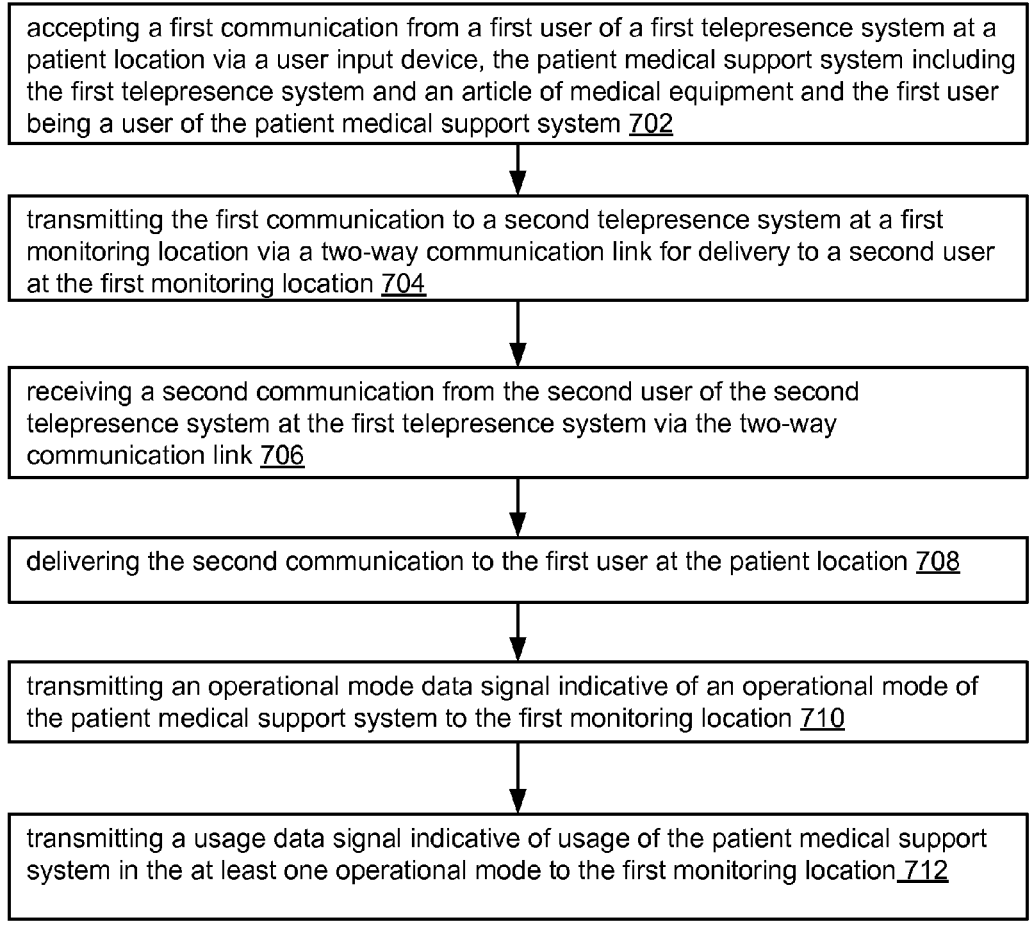
FIG. 7 is a flow diagram of a method of communicating usage of a patient medical support system.

FIG. 7 depicts a method 700 of communicating usage of a patient medical support system. Method 700 includes accepting a first communication from a first user of a first telepresence system at a patient location via a user input device, the patient medical support system including the first telepresence system and an article of medical equipment and the first user being a user of the patient medical support system, at 702; transmitting the first communication to a second telepresence system at a first monitoring location via a two-way communication link for delivery to a second user at the first monitoring location, at 704; receiving a second communication from the second user of the second telepresence system at the first telepresence system via the two-way communication link, at 706; delivering the second communication to the first user at the patient location, at 708; transmitting an operational mode data signal indicative of an operational mode of the patient medical support system to the first monitoring location, at 710; and transmitting a usage data signal indicative of usage of the patient medical support system in the at least one operational mode to the first monitoring location, at 712.

FIGS. 8-13 depict variations and expansions of method 700 as shown in FIG. 7. In the methods depicted in FIGS. 8-13, steps 702-712 are as described generally in connection with FIG. 7. Here and elsewhere, method steps outlined with dashed lines represent steps that are included in some, but not all method aspects, and combinations of steps other than those specifically depicted in the figures are possible as would be known by those having ordinary skill in the relevant art.

Figure 8:
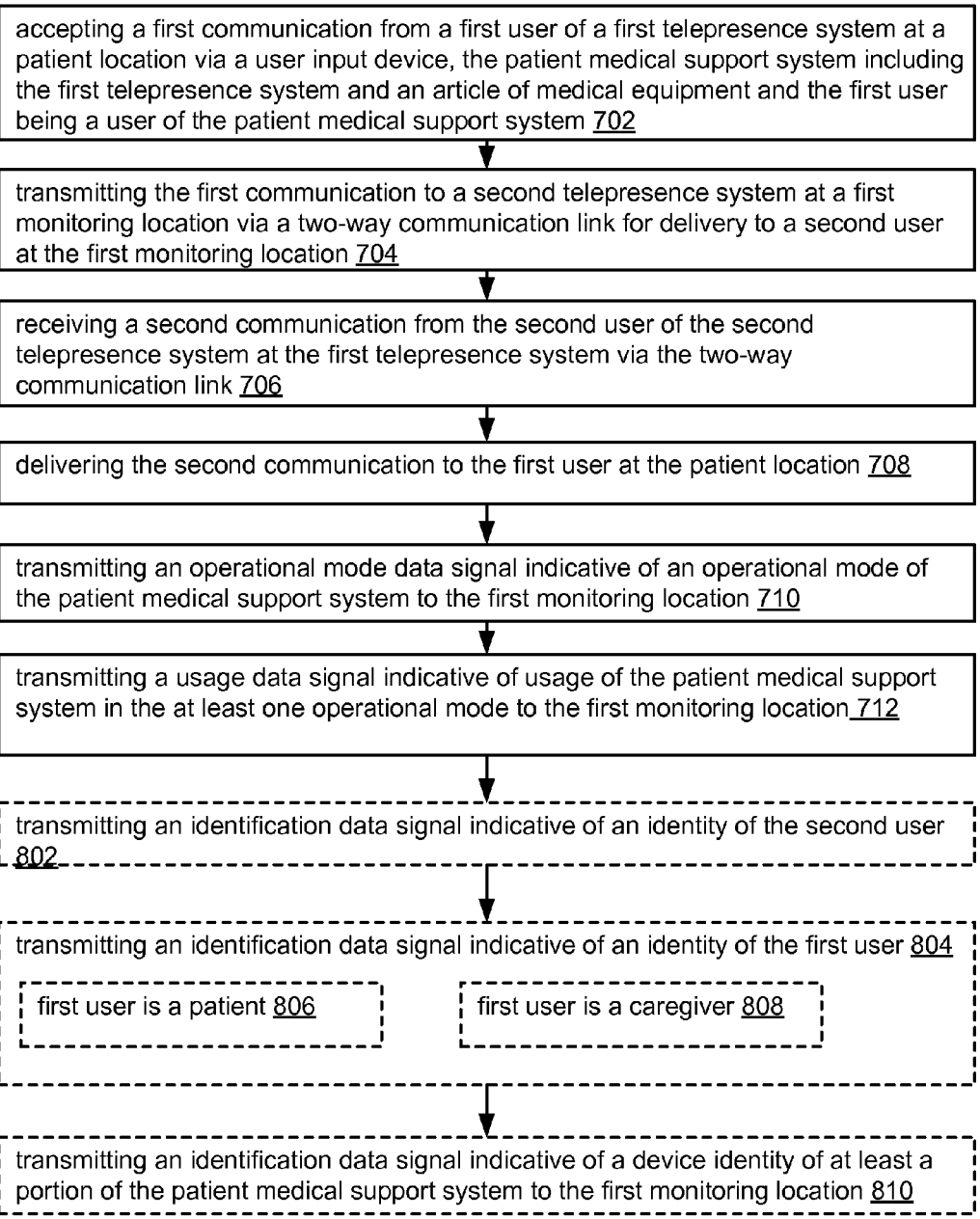
FIG. 8 is a flow diagram of a method of communicating usage of a patient medical support system.

As shown in FIG. 8, in an aspect a method 800, includes transmitting an identification data signal indicative of an identity of the second user (i.e., the user at the first monitoring location), as indicated at 802. In an aspect, method 800 includes transmitting an identification data signal indicative of an identity of the first user, as indicated at 804. The first user may be a patient, as indicated at 806, or a caregiver, as indicated at 808. In another aspect, method 800 includes transmitting an identification data signal indicative of a device identity of at least a portion of the patient medical support system to the first monitoring location, as indicated at 810.

Figure 9:
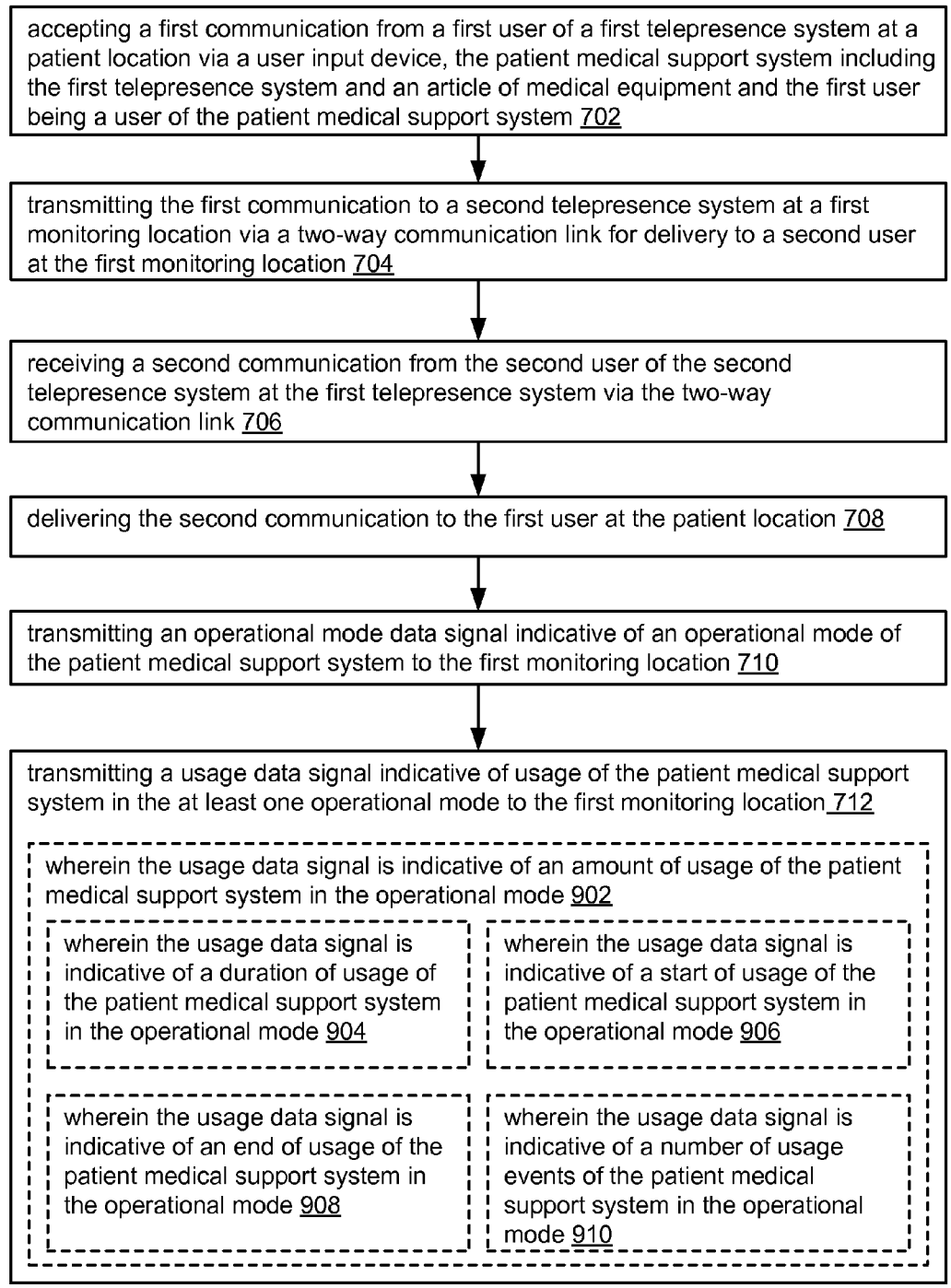
FIG. 9 is a flow diagram of a method of communicating usage of a patient medical support system.

As shown in FIG. 9, in an aspect of a method 900, the usage data signal is indicative of an amount of usage of the patient medical support system in the operational mode, as indicated at 902. In an aspect, the usage data signal is indicative of a duration of usage of the patient medical support system in the operational mode, as indicated at 904. In another aspect, the usage data signal is indicative of a start of usage of the patient medical support system in the operational mode, as indicated at 906. In an aspect, the usage data signal is indicative of an end of usage of the patient medical support system in the operational mode, as indicated at 908. In another aspect, the usage data signal is indicative of a number of usage events of the patient medical support system in the operational mode, as indicated at 910. It will be appreciated that the information transmitted to the first monitoring location in the usage data signal may be combined with other information available at the first monitoring location in order to determine or derive the amount of usage. For example, if start time information is already available, end time information can be used to determine the duration of usage. The amount of usage can be an absolute amount of usage, or an amount of usage during a certain time period. The amount of usage can be determined for a particular time period, which may be, for example, a particular amount of time (e.g., an hour, a day, or a week) or a time period bounded by particular events (e.g., the time between a starting event such as a patient's discharge from the hospital with the patient medical support system and an ending event such as the time that the patient medical support system is no longer needed and is returned to the hospital, or the start and end of a billing cycle). Usage can be expressed in duration or number of events (e.g. the medical support system was used for a total of five hours, or it was used ten times during a one-week period).

FIG. 10 depicts a method 1000, in which the operational mode data signal is indicative of an operational mode of the at least one article of medical equipment, and the usage data signal is indicative of an amount of usage of the at least one article of medical equipment in the operational mode, as indicated at 1002. For example, in various aspects, the operational mode data signal is indicative of one or more of a turned on operational mode (at 1004), a turned off operational mode (at 1006), a standby operational mode (at 1008), a patient data gathering operational mode (at 1010), a treatment delivery operational mode (at 1012), or an error operational mode (at 1014) of the at least one article of medical equipment.

FIG. 11 depicts a method 1100, which in an aspect includes transmitting a medical equipment operational mode command signal to the at least one article of medical equipment; determining the at least one operational mode based at least in part on the medical equipment operational mode command signal; and determining the usage data signal based at least in part on a time of transmission of the medical equipment operational mode command signal, as indicated at 1102. In another aspect, method 1100 includes receiving a medical equipment operational mode signal from the at least one article of medical equipment; determining the at least one operational mode based at least in part on the medical equipment operational mode signal; and determining the usage data signal responsive to receiving the at least one medical equipment operational mode signal, as indicated at 1104.

FIG. 12 depicts a method 1200 in which the operational mode data signal is indicative of an operational mode of the first telepresence system, and wherein the usage data signal is indicative of an amount of usage of the first telepresence system in the operational mode, as indicated at 1202. In various aspects, the operational mode data signal is indicative of one or more of a turned on operational mode (at 1204), turned off operational mode (at 1206), standby operational mode (at 1208), send communication operational mode (at 1210), receive communication operational mode (at 1212), audio communication operational mode (at 1214), video communication operational mode (at 1216), user-initiated operational mode (at 1218), or medical care provider-initiated operational mode (at 1220) of the first telepresence system.

FIG. 13 depicts a method 1300, which in an aspect includes receiving a telepresence system operational mode signal from the first telepresence system; determining the at least one operational mode based at least in part on the telepresence system operational mode signal; and determining the usage data signal responsive to receiving the telepresence system operational mode signal, as indicated at 1302. In another aspect, method 1300 includes transmitting a telepresence system operational mode command signal to the first telepresence system; determining the at least one operational mode based at least in part on the telepresence system operational mode command signal; and determining the usage data signal based at least in part on the time of transmission of the telepresence system operational mode command signal, as indicated at 1304.

FIG. 14 is a block diagram of a medical support monitoring system 228 at a remote monitoring location 224. Medical support monitoring system includes telepresence system 222 for use at a remote monitoring location 224, which includes at least one user input device 1400 adapted to accept a communication 230 from a user 220 at the remote monitoring location 224 for transmission to a user of a patient medical support system (e.g., user 216 depicted in FIG. 2 but not shown in FIG. 14) at a patient location 204 remote from the first monitoring location via two-way communication link 246. In addition, telepresence system 22 includes at least one user output device 1402, which is adapted to deliver a communication 226 to user 220. Communication 226 is received from the user of the patient medical support system (user 216, not shown in FIG. 14) at patient location 204 via two-way communication link 246. Medical support monitoring system 228 also includes communication circuitry 232, which forms a portion of the two-way communication link 246 between medical support monitoring system 228 at remote monitoring location 224 and the patient medical support system at patient location 204. As discussed herein above, e.g., in connection with FIG. 2, a patient medical support system 202 includes telepresence system 208, article of medical equipment 206 and/or 274, and communication circuitry 212, which forms a portion of a two-way communication link 246. Communication circuitry 232 is adapted to receive at least one operational mode data signal 262 indicative of at least one operational mode of the patient medical support system, receive at least one usage data signal 264 indicative of an amount of usage of the patient medical support system in the at least one operational mode, receive via the two-way communication link the communication from the user at patient location 204 to user 220, and transmit via two-way communication link 246 communication 230 from user 220 to the user at patient location 204. Medical support monitoring system 228 also includes a data storage device 236 and electrical control circuitry 234, which is configured to determine the identity of at least one user of the patient medical support system and control storage of information relating to at least one of the at least one operational mode and the amount of usage of the patient medical support system in the at least one operational mode in data storage device 236, in association with the identification of the at least one user of the patient medical support system.

In an aspect, communication circuitry 232 is adapted to receive an identification data signal 266 from the patient medical support system. In an aspect, electrical control circuitry 234 is configured to determine the identity 1406 of at least one user of the patient medical support system based at least in part on identification data signal 266, e.g. through the use of identity determination module 1404. In an aspect, identification data signal 266 is indicative of the identity of a user of the patient medical support system, for example, a patient or caregiver. In another aspect, the user identified by identity determination module 1404 is a user of the medical support monitoring system, e.g. user 220, who may be, for example, a medical care provider. In an aspect, identification data signal 266 is a device identification data signal indicative of the device identity 1408 of at least a portion of the patient medical support system, and electrical control circuitry 234 is configured to determine the identity of the at least one user of the patient medical support system by retrieving a user identity associated with the device identity 1408 of the at least a portion of the patient medical support system from data storage device 236, wherein the user identity data is stored in data storage device 236 in association with the device identity of the at least a portion of the patient medical support system. This approach is described in greater detail herein below, in connection with FIG. 20A. In an aspect, data storage device 236 stores one or more database 238, which may contain one or more of medical records 240 and billing records 242. In an aspect, electrical control circuitry 234 includes usage determination module 1410, including one or more of software and electronic circuitry configured to determine usage of patient medical support system or components thereof based on usage data signal 264. In an aspect, electrical control circuitry 234 includes value determination module 1412, including one or more of software and electronic circuitry configured for determining a value (e.g., a monetary value) of usage of the patient medical support system. Determination of value of patient medical support system usage is described herein below, in connection with FIG. 20B.

In an aspect, communication circuitry 232 is adapted to transmit a query 272 addressed to at least a portion of the patient medical support system, and receive the at least one operational mode data signal 262 and at least one usage data signal 264 from the patient medical support system in response to the query. In an aspect, electrical control circuitry 234 is configured to determine the identity of at least one user of the patient medical support system based at least in part on identification data signal 266.

In an aspect, telepresence system 222 is substantially similar to telepresence system 208 described in connection with FIG. 3. For example, in an aspect, telepresence system 222 includes a two-way audiovisual system. In various aspects, telepresence system 222 includes at least one of a microphone, a speaker, a video display, and a camera. In an aspect, user input device 1400 includes at least one of a camera, a video camera, a mouse, a keyboard, a joystick, a touchpad, a touchscreen, a microphone, a button, a switch, a motion-tracking device, an eye tracking device, an EEG sensor, and EMG sensor, a brain-computer interface, and a braille translation/transcription device. In various aspects, at least one user output device 1402 includes at least one of a video display, a speaker, a braille display, a haptic device. Electrical control circuitry 234 may include at least one of hardware, software, firmware, and a microprocessor, for example as described in connection with electrical control circuitry 210 as shown in FIG. 5. Communication circuitry 232 is adapted to provide at least one of WiFi, cellular, wireless, radio frequency, satellite, and BlueTooth communication. Establishment of communication link 246 is generally as described in connection with FIG. 5.

In an aspect, communication 230 in medical support monitoring system 228 is configured to communicate with communication circuitry 1422 at a secondary monitoring location 252. Secondary monitoring location 252 may be an entity such as an insurance company or other payor 1420. In an aspect, medical support monitoring system 228 communicates with secondary monitoring location 252 via communication link 250 established between communication circuitry 232 and communication circuitry 1422, to provide for transmittal of information relating to medical records 240 and billing records 242. Information may relate to usage of patient medical support system, the value of the usage of the patient medical support system, etc. A system at secondary monitoring location 252 may include electrical control circuitry 1424 and one or more data storage device 1426.

FIG. 15 depicts a method 1500 of monitoring usage of a patient medical support system. Method 1500 includes accepting a first communication from a first user of a first telepresence system at a first monitoring location via a user input device, as indicated at 1502; transmitting the first communication to a second telepresence system at a patient location remote from the first monitoring location via a two-way communication link for delivery to a second user at the patient location, the second user being a user of the patient medical support system, the patient medical support system including the second telepresence system and at least one article of medical equipment, as indicated at 1504; receiving a second communication from the second user at the first monitoring location via the two-way communication link, as indicated at 1506; delivering the second communication to the first user via a user output device, the first telepresence system including the user output device, as indicated at 1508; receiving a telepresence system operational mode data signal at the first monitoring location, the telepresence system operational mode data signal indicative of an operational mode of the second telepresence system, as indicated at 1510; receiving a telepresence system usage data signal at the first monitoring location, the telepresence system usage data signal indicative of usage of the second telepresence system in the operational mode, as indicated at 1512; receiving a medical equipment operational mode data signal at the first monitoring location, the medical equipment operational mode data signal indicative of an operational mode of the at least one article of medical equipment, as indicated at 1514; and receiving a medical equipment usage data signal at the first monitoring location, the medical equipment usage data signal indicative of usage of the at least one article of medical equipment in the operational mode, as indicated at 1516. The steps of receiving a telepresence system operational mode data signal at the first monitoring location, the telepresence system operational mode data signal indicative of an operational mode of the second telepresence system, as indicated at 1510, and receiving a telepresence system usage data signal at the first monitoring location, the telepresence system usage data signal indicative of usage of the second telepresence system in the operational mode, as indicated at 1512, are optional, as indicated by the dashed lines and in some cases may be omitted.

FIGS. 16-19, 21-22 and 24 depict variations and expansions of method 1500 as shown in FIG. 15. In the methods depicted in FIGS. 16-19, 21-22 and 24, steps 1502-1516 are as described generally in connection with FIG. 15.

As shown in FIG. 16, in an aspect a method 1600 includes storing information in a data storage device at the first monitoring location, wherein the stored information includes at least one of the operational mode of the second telepresence system, the usage of the second telepresence system, the operational mode of the at least one article of medical equipment, and the usage of the at least one article of medical equipment, as indicated at 1602. In another aspect, a method 1600 includes transmitting a signal to a third location for storage in a data storage device at the third location, wherein the signal contains information regarding at least one of the operational mode of the second telepresence system, the usage of the second telepresence system, the operational mode of the at least one article of medical equipment, and the usage of the at least one article of medical equipment, as indicated at 1604.

As shown in FIG. 17, in various aspects of a method 1700, the telepresence system operational mode data signal is indicative of one or more of a turned on operational mode (as indicated at 1702), a turned off operational mode (as indicated at 1704), a standby operational mode (as indicated at 1706), a send communication operational mode (as indicated at 1708), a receive communication operational mode (as indicated at 1710), an audio communication operational mode (as indicated at 1712), a video communication operational mode (as indicated at 1714), a user-initiated operational mode (as indicated at 1716), or a medical care provider-initiated operational mode (as indicated at 1718) of the second telepresence system.

As shown in FIG. 18, in an aspect of a method 1800, the telepresence system usage data signal is indicative of an amount of usage of the second telepresence system in the operational mode, as indicated at 1802; a duration of usage of the second telepresence system in the operational mode, as indicated at 1804; a start of usage of the second telepresence system in the operational mode, as indicated at 1806; an end of usage of the second telepresence system in the operational mode, as indicated at 1808; or a number of usage events of the second telepresence system in the operational mode, as indicated at 1810.

In another aspect of method 1800, the medical equipment operational mode data signal is indicative of one or more of a turned on operational mode of the at least one article of medical equipment, as indicated at 1812; a turned off operational mode of the at least one article of medical equipment, as indicated at 1814; a standby operational mode of the at least one article of medical equipment, as indicated at 1816; a patient data gathering operational mode of the at least one article of medical equipment, as indicated at 1818; a treatment delivery operational mode of the at least one article of medical equipment, as indicated at 1820; or an error operational mode of the at least one article of medical equipment, as indicated at 1822.

Figure 19:
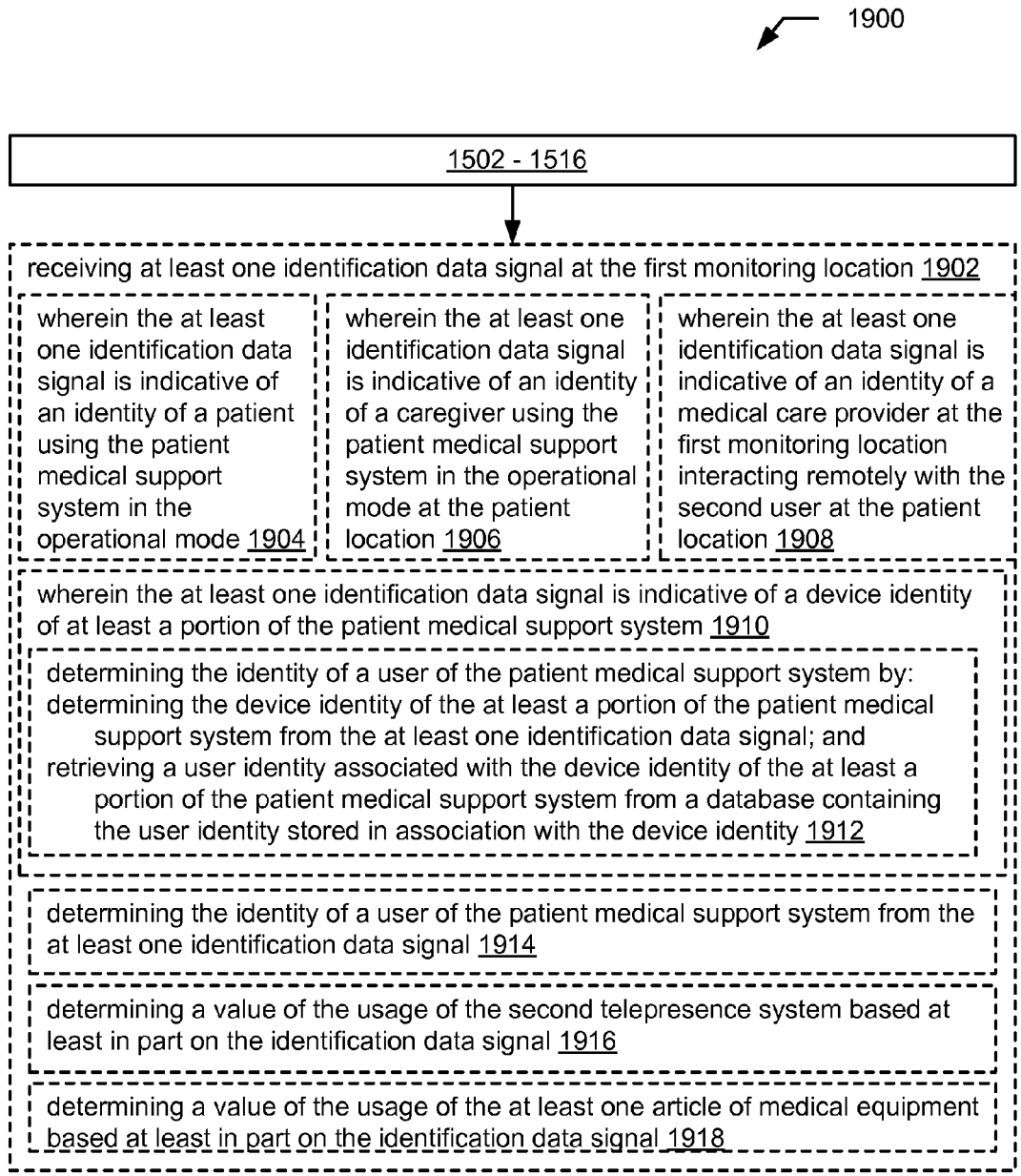
FIG. 19 is a flow diagram of a method of monitoring usage of a patient medical support system.

As shown in FIG. 19, in an aspect, a method 1900 includes receiving at least one identification data signal at the first monitoring location, as indicated at 1902. In a further aspect, the at least one identification data signal is indicative of one or more of an identity of a patient using the patient medical support system in the operational mode, as indicated at 1904; an identity of a caregiver using the patient medical support system in the operational mode at the patient location, as indicated at 1906; or an identity of a medical care provider at the first monitoring location interacting remotely with the second user at the patient location, as indicated at 1908. In an aspect, the at least one identification data signal is indicative of a device identity of at least a portion of the patient medical support system, as indicated at 1910. If the at least one identification data signal is indicate of a device identity of at least a portion of the patient medical support system, in an aspect method 1900 includes determining the identity of a user of the patient medical support system by determining the device identity of the at least a portion of the patient medical support system from the at least one identification data signal and retrieving a user identity associated with the device identity of the at least a portion of the patient medical support system from a database containing the user identity stored in association with the device identity, as indicated at 1912.

In various aspects, method 1900 includes determining the identity of a user of the patient medical support system from the at least one identification data signal, as indicated at 1914; determining a value of the usage of the second telepresence system based at least in part on the identification data signal, as indicated at 1916; or determining a value of the usage of the at least one article of medical equipment based at least in part on the identification data signal, as indicated at 1918.

FIG. 20A illustrates an approach for determining the identity of a user based upon the identity of a device associated with the user. FIG. 20A depicts a database 2000, which may be stored in a data storage device at a remote monitoring location, for example. Database 2000 stores records of the identities of particular users in association with particular devices. In an aspect, user identity 2002a is the identity of a first user a, and device identity 2004a is the identity of a device assigned to first user a. For example, device identity 2004a may be the identity of a patient medical support system that is issued to user a (a patient) upon discharge from a hospital. User identity 2002a is stored in database 2000 in association with the device identity 2004a at the time the patient medical support system is issued to user a. Similarly, user identities 2002b, 2002c, and 2002d are stored in database 2000 in association with device identities 2004b, 2004c, and 2004d, respectively. During monitoring of usage of the patient medical support system, at the remote monitoring location, in an aspect, electrical control circuitry at remote monitoring location determines the identity of the patient medical support system based on device identity information (device identity 2004a) contained in the identification data signal received from the patient medical support system. The electrical control circuitry at the remote monitoring location then determines the identity of the patient by retrieving user identity 2002a associated with the device identity 2004a from database 2000.

FIG. 20B illustrates determination of the value of usage of a patient medical support system. In an aspect, such a determination takes place at the remote monitoring location, although in some aspects it may take place at the patient location. FIG. 20B depicts a database 2010. Referring back to FIG. 2, such a database may be stored, for example, in data storage device 236 in medical support monitoring system 228, in data storage device 276 in patient medical support system 202, or in some other location. Returning to FIG. 20B, in an aspect, database 2010 stores a function 2012 which defines a value of a usage as a mathematical function F of one or more user identities $UI_1$, $UI_2$, and $UI_3$, one or more device identities $DI_1$, $DI_2$, and one or more operational modes $OM_1$, $OM_2$, and $OM_3$. In general, this relationship can be represented as Value=F($UI_1$, $UI_2$, $UI_3$, $DI_1$, $DI_2$, $DI_3$, $OM_1$, $OM_2$, and $OM_3$). Various functions may be used to determine the value of the usage, depending on how the value information is intended to be used, and the function depicted in FIG. 20B is an example and is not intended to be limiting. Furthermore, the value of the usage may be a function of a larger or smaller numbers of users, devices, operational modes, and other variables. In the present example, the specific function is Value=Base Rate+(Unit Rate×Usage Amount), as indicated at 2014. In the present example, the value of a usage of the patient medical support system is a function of nine variables, which can be stored in database 2010. The nine variables are represented in column 2060, and include first user identity ($UI_1$) 2020, second user identity ($UI_2$) 2022, third user identity ($UI_3$) 2024, first device identity ($DI_1$) 2026, second device identity ($DI_2$) 2028, first operational mode ($OM_1$) 2030, second operational mode ($OM_2$) 2032, third operational mode ($OM_3$) 2034, and usage amount 2036. In the present example, each variable has an associated constant unit rate, which is the rate charged per unit of usage of the entity represented by the variable. The unit rates are stored as an array of values 2016 in database 2010. In addition, in the present example, each variable has an associated constant base rate, which is a one-time charge that is made each time a usage of the entity represented by the variable occurs. The base rates are stored as an array of values 2018 in database 2010. In this example, the total value of the usage is the some of the values of the usages relating to each variable.

The specific variable types of the variables are indicated in column 2062. The variable types may be selected to meet the needs of the entity for which the value is determined. In the present example, the variable types are as follows: the first user identity is the identity of the patient 2040. The second user identity is the identity of the caregiver 2042. The third user identity is the identity of the medical care provider 2044. The first device identity is the identity of telepresence system 2046. The second device identity is the identity of medical equipment 2048. The first operational mode is telepresence mode 1 (2050), the second operation mode is telepresence mode 2 (2052), and the third operational mode is medical equipment mode 1 (2054). In the present example, the usage amount is the number of minutes used (2056); alternatively, the usage among could be indicated in number of hours, number of days, instances of usage, etc., as discussed elsewhere herein. Columns 2064, 2066, and 2068 represent examples of particular usages of the medical support system, from which the values of usages can be determined. In the examples of columns 2064, 2066, and 2068, for all usages the patient is a single patient "X"; for example, the patient could be identified as "Joe Smith," Patient ID No. 12345, or any other unique identifier. The second user, the caregiver may not be the same for every usage. For example, during the usage of column 2064, the caregiver is a nurse, while during the usage of column 2066, the caregiver is a physical therapist. During the usage of column 2068, no caregiver is present, so the caregiver is indicated as "none." The medical care provider 2044 may also be different for different usages. For example, in the usage of column 2064, the caregiver is a surgeon. A specific surgeon (e.g., Dr. Kim) may be indicated, if costs or if the cost for all surgeons is the same, it may be necessary only to indicate that the medical care provider was a surgeon. During the usages of columns 2066 and 2068, the medical care provider is a physician. Again, a specific physician may be indicated, if appropriate. In the present example, a single telepresence system ("telepresence system Y") and a single article of medical equipment ("Blood Pressure Monitor") are used. The first and second operational modes 2030 and 2032, respectively, pertain to the telepresence system. It can be seen from the examples of columns 2064, 2066, and 2068 that the telepresence system can have two different operational modes at the same time (receive communication and user 3 initiated, send communication and user 2 initiated, and send communication and user 1 initiated, respectively. Third operational mode 2034 pertains to the article of medical equipment. The examples of columns 2064, 2066, and 2068 show three different operational modes of the article of medical equipment: standby, patient data gathering, and turned off, respectively. Finally, the usage amount for the usages of columns 2064, 2066, and 2068 are indicated (e.g., 15 minutes, 30 minutes, and 20 minutes). Based on the values stored in database 2010, the values of the usages of columns 2064, 2066, and 2068 can be determined according to function 2014.

Table 1 shows examples of base and unit rates for various aspects of usage of the medical support system, as represented in column 2064 of FIG. 20B, and calculation of the total value of the usage, which is determined by multiplying the unit rate and usage amount for each variable and adding this to the base rate for the variable to determine the value for each variable, and then summing the values for all the variables to determine the total value of the usage. This example represents the circumstance in which the patient has returned home after a surgery, and is having a scheduled follow-up consultation with a surgeon. A nurse (e.g. a home health nurse) is present at the patient's home to check the patient's health and to consult with the surgeon as well. The higher base rate for the nurse relative to the surgeon reflects the need for the nurse to travel to the patient's home. The higher unit rate for the surgeon than the nurse reflects the higher rate charged by the surgeon per minute. It will be appreciated that the various rates listed in the table are merely examples intended to illustrate how the value calculation is performed, and are not intended to reflect actual rates that are used by any particular health care providing entity.

TABLE 1

(Usage Value Calculation for Example of Col. 2064, FIG. 20B)

| | Base Rate | Unit Rate | Usage Amount | Value |
|---|---|---|---|---|
| Patient X | $0.00 | $0.00/min | 15 minutes | $0.00 |
| Nurse | $30.00 | $1.00/min | 15 minutes | $45.00 |
| Surgeon | $25.00 | $5.00/min | 15 minutes | $100.00 |
| Telepresence System Y | $15.00 | $0.00/min | 15 minutes | $15.00 |
| Blood Pressure Monitor | $5.00 | $1.00/min | 15 minutes | $5.00 |
| Receive Communication | $0.00 | $1.00/min | 15 minutes | $15.00 |
| User 3 Initiated | $5.00 | $0.00/min | 15 minutes | $5.00 |
| Standby | $0.00 | $0.50/min | 15 minutes | $7.50 |

Total Value = Base Rate + (Unit Rate × Usage Amount) = $192.50

Figure 21:
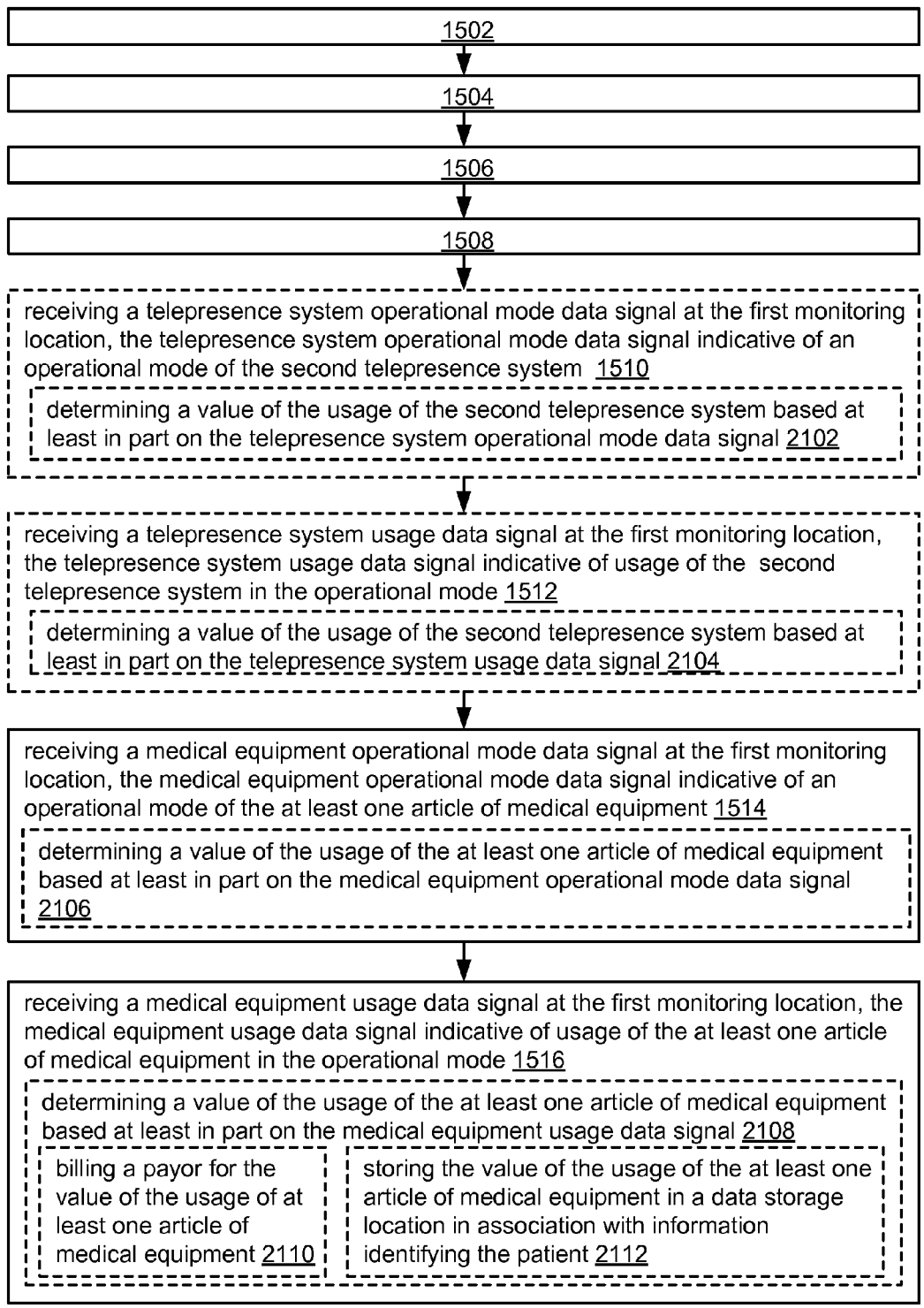
FIG. 21 is a flow diagram of a method of monitoring usage of a patient medical support system.

As shown in FIG. 21, in an aspect, a method 2100 includes determining a value of the usage of the second telepresence system based at least in part on the telepresence system operational mode data signal, as indicated at 2102. In an aspect, method 2100 includes determining a value of the usage of the second telepresence system based at least in part on the telepresence system usage data signal, as indicated at 2104. In another aspect, method 2100 includes determining a value of the usage of the at least one article of medical equipment based at least in part on the medical equipment operational mode data signal, as indicated at 2106. In yet another aspect, method 2100 includes determining a value of the usage of the at least one article of medical equipment based at least in part on the medical equipment usage data signal, as indicated at 2108. Method 2100 may also include billing a payor for the value of the usage of at least one article of medical equipment, as indicated at 2110, or storing the value of the usage of the at least one article of medical equipment in a data storage location in association with information identifying the patient, as indicated at 2112.

As shown in FIG. 22, in an aspect a method 2200 include determining an amount of usage of the at least one article of medical equipment based at least in part on the medical equipment usage data signal, dissociating information indicative of patient identity from the determined amount of usage of the at least one article of medical equipment, and combining the determined amount of usage of the at least one article of medical equipment with amount of usage values determined from a plurality of other patients, as indicated at 2202.

FIG. 23 depicts in schematic form a data handling process 2300 used in anonymization of patient records pertaining to medical equipment usage. Medical equipment usage data 2302, which may be stored in a database at a medical support monitoring location such as a hospital, for example, includes records including associated patient identity 2304 and medical equipment usage 2306 data, for N patients. It may be desired to combine the patient data for various purposes, ranging from medical research population studies to data analysis used for business purposes of e.g., a hospital or insurance company. Therefore, medical equipment usage data 2302 may be processed by an anonymization 2308 module and stored in database 2310, in which anonymized patient identifier data 2312a-2312d are associated with medical equipment usage data 2314a-2314d.

Similarly, FIG. 23 depicts in schematic form data handling process 2320 used in anonymization of patient records pertaining to telepresence system usage. Telepresence system usage data 2322, which may be stored in a database at a medical support monitoring location such as a hospital, for example, includes records including associated patient identity 2324 and telepresence system usage 2326 data, for N patients. Telepresence system usage data 2322 may be processed by an anonymization module 2328 and stored in database 2330, in which anonymized patient identifier data 2332a-2332d are associated with telepresence system usage data 2334a-2334d. As shown in FIG. 24, in an aspect a method 2400 includes determining an amount of usage of the first telepresence system at 2402. In an aspect, method 2400 includes determining a value of the usage of the first telepresence system based at least in part on the amount of usage of the first telepresence system, as indicated at 2404. In another aspect, method 2400 includes billing a payor for the value of the usage of the first telepresence system, as indicated at 2406. In an aspect, method 2400 includes storing the value of the usage of the first telepresence system in a data storage location in association with information identifying the patient, as indicated at 2408. Once anonymized, data pertaining to medical equipment or telepresence system usage may be analyzed in various ways without compromising the privacy of the patients with whom the data was originally associated.

FIG. 25 depicts a method 2500 of monitoring usage of a patient medical support system. Method 2500 may be performed at a hospital, in part with a medical support monitoring system 228 as depicted in FIG. 14, for example. Method 2500 includes providing a patient with a patient medical support system, as indicated at 2502, where the patient medical support system includes at least one article of medical equipment; electrical control circuitry configured to determine two or more different operational modes of the at least one article of medical equipment and determine a first usage data signal indicative of an amount of usage of the at least one article of medical equipment in a first operational mode, the first operational mode being one of the two or more different operational modes; and communication circuitry for transmitting the first usage data signal and an identification data signal from a patient location remote from a monitoring location to the monitoring location. Method 2500 further includes receiving the first usage data signal at the monitoring location, as indicated at 2504; receiving the identification data signal at the monitoring location, as indicated at 2506; determining at least one user identification associated with a user of the patient medical support system based at least in part on the identification data signal, as indicated at 2508; and determining an amount of usage of the at least one article of medical equipment based at least in part on the first usage data signal, as indicated at 2510.

FIGS. 26-30 depict variations and expansions of method 2500 as shown in FIG. 25. In the methods depicted in FIGS. 26-30, steps 2502-2510 are as described generally in connection with FIG. 25.

In an aspect of method 2600 shown in FIG. 26, the identification data signal contains a user identification of a user of the patient medical support system, as indicated at 2602. In another aspect, the identification data signal contains a device identification of at least a portion of the patient medical support system, as indicated at 2604. For example, the device identification may be associated with a user identification of a user of the patient medical system in a database, as indicated at 2606, and in connection therewith, method 2600 may further include determining the user identification by retrieving the user identification associated with the device identification, as indicated at 2608. In an aspect, determining the amount of usage of the at least one article of medical equipment includes determining the amount of usage of the at least one article of medical equipment during a first time period, as indicated at 2610. In another aspect, method 2600 includes associating the amount of usage of the at least one article of medical equipment with the patient based at least in part on the user identification, as indicated at 2612.

Figure 27:
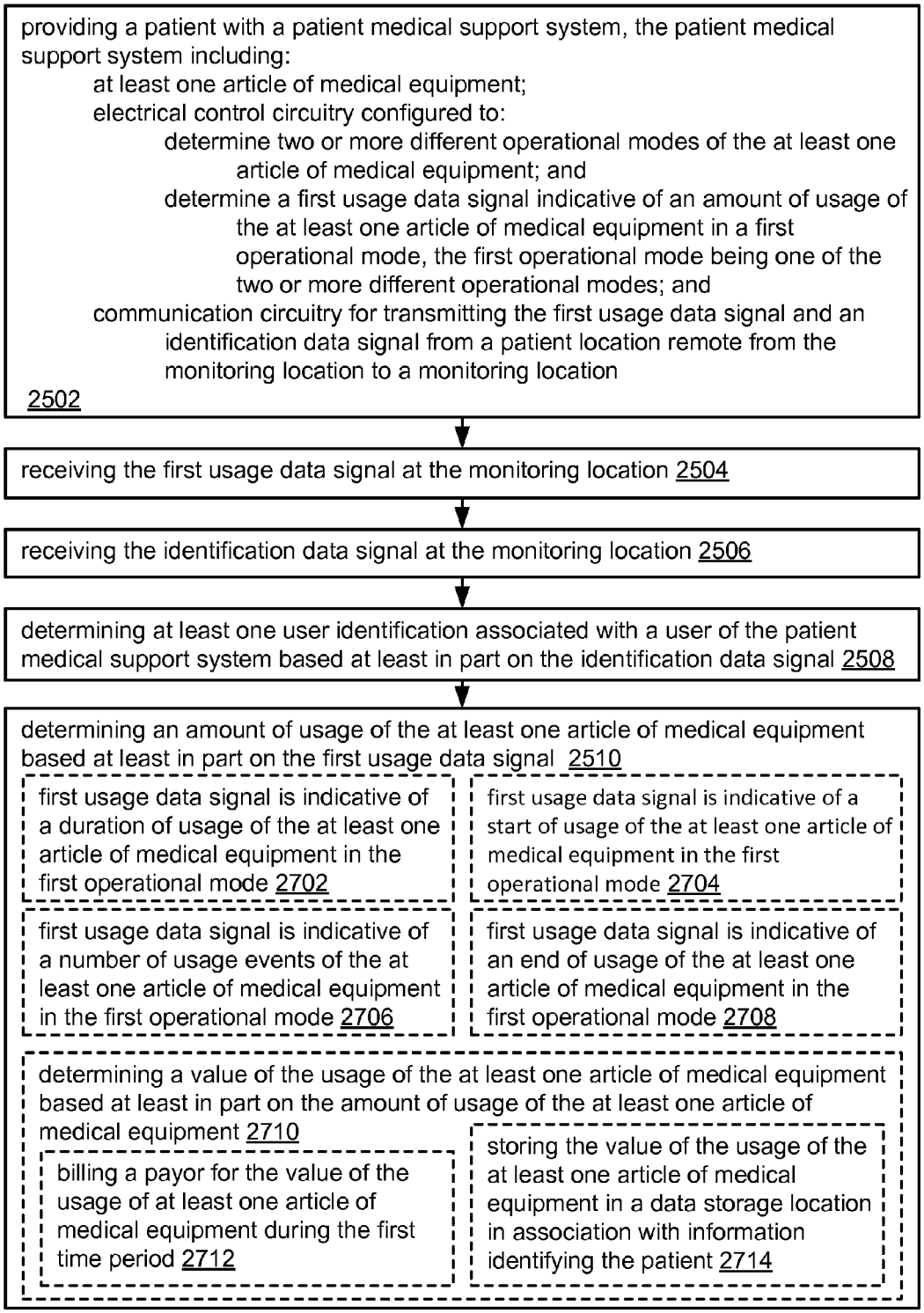
FIG. 27 is a flow diagram of a method of monitoring usage of a patient medical support system.

FIG. 27 depicts further aspects of a method 2700. For example, in various aspects, the first usage data signal is indicative of a duration of usage of the at least one article of medical equipment in the first operational mode, as indicated at 2702; a start of usage of the at least one article of medical equipment in the first operational mode, as indicated at 2704; an end of usage of the at least one article of medical equipment in the first operational mode, as indicated at 2706; or a number of usage events of the at least one article of medical equipment in the first operational mode, as indicated at 2708. In a further aspect, method 2700 includes determining a value of the usage of the at least one article of medical equipment based at least in part on the amount of usage of the at least one article of medical equipment, as indicated at 2710. Furthermore, method 2710 may then include one or more of billing a payor for the value of the usage of at least one article of medical equipment during the first time period, as indicated at 2712, or storing the value of the usage of the at least one article of medical equipment in a data storage location in association with information identifying the patient, as indicated at 2714.

As shown in FIG. 28, in another aspect, a method 2800 includes dissociating information identifying the patient from the determined amount of usage of the at least one article of medical equipment; and combining the determined amount of usage of the at least one article of medical equipment with amount of usage values determined from a plurality of other patients, as indicated at 2802, e.g. as described in connection with FIG. 23.

As shown in FIG. 29, in an aspect a method 2900 includes receiving a telepresence system usage data signal indicative of an amount usage of a telepresence system at the patient location, as indicated at 2902. In connection therewith, method 2900 may include determining the amount of usage of the telepresence system based at least in part on the telepresence system usage data signal, as indicated at 2904. Method 2900 may then additionally include dissociating information identifying the patient from the determined amount of usage of the telepresence system and combining the determined amount of usage of the telepresence system with amount of usage values determined from a plurality of other patients, as indicated at 2906. In various aspects, the telepresence system usage data signal is indicative of one or more of a duration of usage of the telepresence system, as indicated at 2908; a start of usage of the telepresence system, as indicated at 2910; an end of usage of the telepresence system, as indicated at 2912; or a number of usage events of the telepresence system, as indicated at 2914. In a further aspect, method 2900 includes associating the amount of usage of the telepresence system with the patient based at least in part on the at least one user identification, as indicated at 2916. In another aspect, method 2900 includes determining a value of the usage of the telepresence system based at least in part on the amount of usage of the telepresence system, as indicated at 2918. Method 2900 may then also includes one or more of billing a payor for the value of the usage of telepresence system, as indicated at 2920 or storing the value of the usage of the telepresence system in a data storage location in association with information identifying the patient, as indicated at 2922, as described in connection with FIG. 23.

Figure 30:
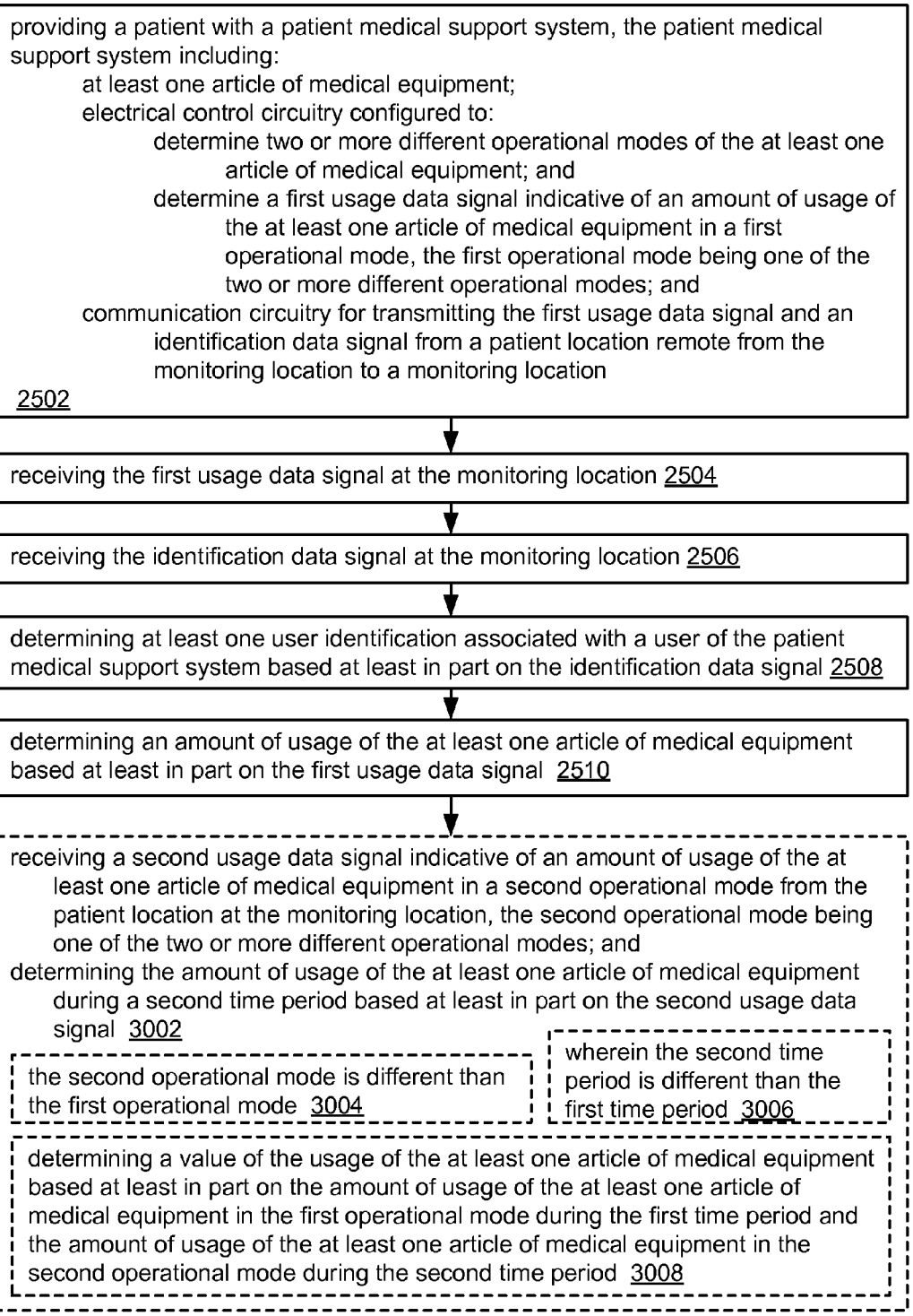
FIG. 30 is a flow diagram of a method of monitoring usage of a patient medical support system

FIG. 30 depicts a method 3000, which includes receiving a second usage data signal indicative of an amount of usage of the at least one article of medical equipment in a second operational mode from the patient location at the monitoring location, the second operational mode being one of the two or more different operational modes; and determining the amount of usage of the at least one article of medical equipment during a second time period based at least in part on the second usage data signal, as indicated at 3002. In an aspect, the second operational mode is different than the first operational mode, as indicated at 3004. In an aspect, the second time period is different than the first time period, as indicated at 3006. In an aspect, method 3000 includes determining a value of the usage of the at least one article of medical equipment based at least in part on the amount of usage of the at least one article of medical equipment in the first operational mode during the first time period and the amount of usage of the at least one article of medical equipment in the second operational mode during the second time period, as indicated at 3008.

FIG. 31 is a flow diagram of a method 3100 of monitoring usage of a patient medical support system including an article of medical equipment and a telepresence system. Method 3100 may be performed with the use of a medical support monitoring system as shown in FIG. 14, for example. Method 3100 includes receiving a medical equipment operational mode data signal at a first monitoring location from the patient medical support system located remote from the first monitoring location at a patient location, the medical equipment operational mode data signal indicative of a medical equipment operational mode of at least two operational modes of the article of medical equipment, as indicated at 3102; receiving a medical equipment usage data signal at the first monitoring location from the patient medical support system, the medical equipment usage data signal indicative of usage of the article of medical equipment in the medical equipment operational mode, as indicated at 3104; receiving a first telepresence system operational mode data signal at the first monitoring location from the patient medical support system, the first telepresence system operational mode data signal indicative of a first telepresence system operational mode of at least two operational modes of the telepresence system, as indicated at 3106; receiving a first telepresence system usage data signal at the first monitoring location from the patient medical support system, the first telepresence system usage data signal indicative of usage of the telepresence system in the first telepresence system operational mode, as indicated at 3108; determining at least one user identification associated with a user of the patient medical support system, as indicated at 3110; and storing information to a data storage device, the information regarding at least one of the medical equipment operational mode, the usage of the article of the medical equipment, the first telepresence system operational mode and the usage of the telepresence system, in association with the at least one user identification, as indicated at 3112. The steps of receiving a first telepresence system operational mode data signal at the first monitoring location from the patient medical support system, the first telepresence system operational mode data signal indicative of a first telepresence system operational mode of at least two operational modes of the telepresence system, as indicated at 3106, and receiving a first telepresence system usage data signal at the first monitoring location from the patient medical support system, the first telepresence system usage data signal indicative of usage of the telepresence system in the first telepresence system operational mode, as indicated at 3108, are optional and in some aspects may be omitted, as indicated by the dashed lines.

FIGS. 32-35 depict variations and expansions of method 3100 as shown in FIG. 31. In the methods depicted in FIGS. 32-35, steps 3102-3112 are as described generally in connection with FIG. 31.

As shown in FIG. 32, in various aspects of a method 3200, the first telepresence system operational mode data signal is indicative of one or more of various operational modes of the telepresence system. For example, in various aspects, the first telepresence system operational mode data signal is indicative of a turned on operational mode, as indicated at 3202; a turned off operational mode, as indicated at 3204; a standby operational mode, as indicated at 3206; a send communication operational mode, as indicated at 3208; a receive communication operational mode, as indicated at 3210; an audio communication operational mode, as indicated at 3212; a video communication operational mode, as indicated at 3214; a user-initiated operational mode, as indicated at 3216; or a medical care provider-initiated operational mode of the telepresence system, as indicated at 3218.

As shown in FIG. 33, in an aspect of method 3300 the data storage device is located at the first monitoring location, as indicated at 3302. In another aspect, the method includes transmitting information to a second monitoring location remote from the first monitoring location, wherein the data storage device is located at the second monitoring location, the transmitted information regarding at least one of the medical equipment operational mode, the usage of the article of the medical equipment, the first telepresence system operational mode and the usage of the telepresence system, in association with the at least one user identification, as indicated at 3304.

As shown in FIG. 34, in an aspect a method 3400 includes determining an amount of usage of the article of medical equipment based at least in part on the medical equipment usage data signal, as indicated at 3402. In a further aspect, method 3400 may then also include determining a value of the usage of the article of medical equipment based at least in part on the amount of usage of the article of medical equipment, as indicated at 3406. Method 3400 may also include one or more of billing a payor for the value of the usage of article of medical equipment during the first time period, as indicated at 3408, or comprising storing the value of the usage of the article of medical equipment in a data storage location in association with information identifying the patient, as indicated at 3410. In another aspect, the method also includes dissociating information identifying the patient from the determined amount of usage of the article of medical equipment and combining the determined amount of usage of the article of medical equipment with amount of usage values determined from a plurality of other patients, as indicated at 3412, and described, for example, in connection with FIG. 23.

FIG. 35 illustrates further aspects of a method 3500, which includes steps 3102-3112 as described in connection with FIG. 31. In an aspect, method 3500 includes determining an amount of usage of the telepresence system based at least in part on the first telepresence system usage data signal, as indicated at 3502. In connection therewith, in an aspect method 3500 includes associating the amount of usage of the telepresence system with a patient based at least in part on the at least one user identification, as indicated at 3504. In another aspect, method 3500 includes determining a value of the usage of the telepresence system based at least in part on the amount of usage of the telepresence system, as indicated at 3506. Method 3500 may then also include one or more of billing a payor for the value of the usage of telepresence system, as indicated at 3508, or storing the value of the usage of the telepresence system in a data storage location in association with information identifying the patient, as indicated at 3510. In another aspect, method 3500 includes dissociating information identifying the patient from the determined amount of usage of the telepresence system; and combining the determined amount of usage of the telepresence system with amount of usage values determined from a plurality of other patients, as indicated at 3512, and described in connection with FIG. 23.

Method 3500 may also include receiving a second telepresence system usage data signal indicative of an amount of usage of the telepresence system in a second telepresence system operational mode from the patient location at the monitoring location, the second telepresence system operational mode being one of the two or more different telepresence system operational modes; and determining the amount of usage of the telepresence system in the second telepresence system operational mode based at least in part on the second telepresence system usage data signal, as indicated at 3514. The second operational mode is different than the first operational mode, as indicated at 3516, or it may be the same. In an aspect, the second telepresence usage data signal is indicative of telepresence system usage occurring during a different time period than usage indicated by the first telepresence system usage data signal, as indicated at 3518. In an aspect, method 3500 includes determining a value of the usage of the telepresence system based at least in part on the first telepresence usage data signal and the second telepresence data signal, as indicated at 3520.

In various embodiments, methods as described herein may be performed according to instructions implementable in hardware, software, and/or firmware. Such instructions may be stored in non-transitory machine-readable data storage media, for example. Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware in one or more machines, compositions of matter, and articles of manufacture. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures. Electrical circuitry, for example, may have one or more paths of electrical current constructed and arranged to implement various functions as described herein. In some implementations, one or more media may be configured to bear a device-detectable implementation when such media hold or transmit device detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components.

Implementations may include executing a special-purpose instruction sequence or invoking circuitry for enabling, triggering, coordinating, requesting, or otherwise causing one or more occurrences of virtually any functional operations described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled/implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In an embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to non-transitory machine-readable data storage media such as a recordable type medium such as a floppy disk, a hard disk drive, a Compact Disc (CD), a Digital Video Disk (DVD), a digital tape, a computer memory, etc. A signal bearing medium may also include transmission type medium such as a digital and/or an analog communication medium (e.g., a fiber optic cable, a waveguide, a wired communications link, a wireless communication link (e.g., transmitter, receiver, transmission logic, reception logic, etc.) and so forth).

FIG. 36 depicts an article of manufacture 3600 that includes one or more non-transitory machine-readable data storage media 3602 bearing one or more instructions 3604 for accepting a first communication from a first user of a first telepresence system at a patient location via a user input device, the patient medical support system including the first telepresence system and an article of medical equipment and the first user being a user of the patient medical support system; transmitting the first communication to a second telepresence system at a first monitoring location via a two-way communication link for delivery to a second user at the first monitoring location; receiving a second communication from the second user of the second telepresence system at the first telepresence system via the two-way communication link; delivering the second communication to the first user at the patient location; transmitting an operational mode data signal indicative of an operational mode of the patient medical support system to the first monitoring location; and transmitting a usage data signal indicative of usage of the patient medical support system in the at least one operational mode to the first monitoring location. Instructions 3604 correspond to method 700 shown in FIG. 7. Other variants of methods as depicted in FIGS. 8-13 and as described herein can be implemented through the use of non-transitory machine-readable data storage media bearing one or more suitable instructions.

FIG. 37 depicts an article of manufacture 3700 that includes one or more non-transitory machine-readable data storage media 3702 bearing one or more instructions 3704 for accepting a first communication from a first user of a first telepresence system at a first monitoring location via a user input device; transmitting the first communication to a second telepresence system at a patient location remote from the first monitoring location via a two-way communication link for delivery to a second user at the patient location, the second user being a user of the patient medical support system, the patient medical support system including the second telepresence system and at least one article of medical equipment; receiving a second communication from the second user at the first monitoring location via the two-way communication link; delivering the second communication to the first user via a user output device, the first telepresence system including the user output device; receiving a telepresence system operational mode data signal at the first monitoring location, the telepresence system operational mode data signal indicative of an operational mode of the second telepresence system; receiving a telepresence system usage data signal at the first monitoring location, the telepresence system usage data signal indicative of usage of the second telepresence system in the operational mode; receiving a medical equipment operational mode data signal at the first monitoring location, the medical equipment operational mode data signal indicative of an operational mode of the at least one article of medical equipment; and receiving a medical equipment usage data signal at the first monitoring location, the medical equipment usage data signal indicative of usage of the at least one article of medical equipment in the operational mode. Instructions 3704 correspond to method 1500 shown in FIG. 15. Other variants of methods as depicted in FIGS. 16-19, 21-22 and 24 and as described herein can be implemented through the use of non-transitory machine-readable data storage media bearing one or more suitable instructions.

FIG. 38 depicts an article of manufacture 3800 that includes one or more non-transitory machine-readable data storage media 3802 bearing one or more instructions 3804 for receiving a medical equipment operational mode data signal at a first monitoring location from a patient medical support system located remote from the first monitoring location at a patient location, the medical equipment operational mode data signal indicative of a medical equipment operational mode of at least two operational modes of the article of medical equipment; receiving a medical equipment usage data signal at the first monitoring location from the patient medical support system, the medical equipment usage data signal indicative of usage of the article of medical equipment in the medical equipment operational mode; receiving a first telepresence system operational mode data signal at the first monitoring location from the patient medical support system, the first telepresence system operational mode data signal indicative of a first telepresence system operational mode of at least two operational modes of the telepresence system; receiving a first telepresence system usage data signal at the first monitoring location from the patient medical support system, the first telepresence system usage data signal indicative of usage of the telepresence system in the first telepresence system operational mode; determining at least one user identification associated with a user of the patient medical support system; and storing information to a data storage device, the stored information regarding at least one of the medical equipment operational mode, the usage of the article of the medical equipment, the first telepresence system operational mode and the usage of the telepresence system, in association with the at least one user identification. Instructions 3804 correspond to method 3100 shown in FIG. 31. Other variants of methods as depicted in FIGS. 32-35 and as described herein can be implemented through the use of non-transitory machine-readable data storage media bearing one or more suitable instructions.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configured by," "configurable to," "operable/operative to," "adapted/adaptable," "able to," "conformable/conformed to," etc. Those skilled in the art will recognize that such terms (e.g. "configured to") generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of monitoring usage of a patient medical support system, comprising:
    providing a patient with a patient medical support system, the patient medical support system including:
        at least one article of medical equipment;
        electrical control circuitry configured to
            determine two or more different operational modes of the at least one article of medical equipment;
            determine a first usage data signal indicative of an amount of usage of the at least one article of medical equipment in a first operational mode, the first operational mode being one of the two or more different operational modes; and
            determine a second usage data signal indicative of an amount of usage of the at least one article of medical equipment in a second operational mode, the second operational mode being one of the two or more different operational modes; and
        communication circuitry for transmitting the first usage data signal and an identification data signal from a patient location remote from a monitoring location to the monitoring location;
    receiving the first usage data signal at the monitoring location;
    receiving the second usage data signal at the monitoring location;
    receiving the identification data signal at the monitoring location;
    determining at least one user identification associated with a user of the patient medical support system based at least in part on the identification data signal;
    determining a first amount of usage of the at least one article of medical equipment based at least in part on the first usage data signal during a first time period;
    determining a second amount of usage of the at least one article of medical equipment during a second time period based at least in part on the second usage data signal;
    retrieving at least one base rate, a first unit rate for usage of the at least one article of medical equipment in the first operational mode, and a second unit rate for usage of the at least one article of medical equipment in the second operational mode from a database in a data storage system; and
    determining a monetary value of the usage of the at least one article of medical equipment based at least in part on the first amount of usage and at least in part on the second amount of usage of the at least one article of medical equipment by multiplying the first amount of usage and the first unit rate to obtain a first value, multiplying the second amount of usage and the second unit rate to obtain a second value, and summing the at least one base rate the first value and the second value.

2. The method of claim 1, including associating the first amount of usage of the at least one article of medical equipment with the patient based at least in part on the user identification.

3. The method of claim 1, including
    dissociating information identifying the patient from the determined first amount of usage of the at least one article of medical equipment; and
    combining the determined first amount of usage of the at least one article of medical equipment with amount of usage values determined from a plurality of other patients.

4. The method of claim 1, including
    receiving a telepresence system usage data signal indicative of an amount usage of a telepresence system at the patient location.

5. The method of claim 4, including determining the amount of usage of the telepresence system based at least in part on the telepresence system usage data signal.

6. The method of claim 5, including
    dissociating information identifying the patient from the determined amount of usage of the telepresence system; and
    combining the determined amount of usage of the telepresence system with amount of usage values determined from a plurality of other patients.

7. The method of claim 4, including determining a monetary value of the usage of the telepresence system based at least in part on the amount of usage of the telepresence system.

8. The method of claim 7, including at least one of billing a payor for the monetary value of the usage of telepresence system and storing the monetary value of the usage of the telepresence system in a data storage location in association with information identifying the patient.

9. The method of claim 7, including determining the monetary value of the usage of the telepresence system based at least in part on an operational mode of the telepresence system.

10. The method of claim 9, including receiving a telepresence system operational mode data sign at monitoring location, wherein the telepresence system operational mode data signal is indicative of one of a user-initiated operational mode or a medical care provider-initiated operational mode of the telepresence system.

11. The method of claim 4, wherein the telepresence system usage data signal is indicative of at least one of a duration of usage, a start of usage, an end of usage, and a number of usage events of the telepresence system.

12. The method of claim 1, wherein the identification data signal contains at least one of a user identification of a user of the patient medical support system and a device identification of at least a portion of the patient medical support system.

13. The method of claim 1, wherein the identification data signal contains a device identification of at least a portion of the patient medical support system, wherein the device identification is associated with a user identification of a user of the patient medical system in a database, and wherein determining the at least one user identification includes retrieving the user identification associated with the device identification.

14. The method of claim 1, wherein the first usage data signal is indicative of at least one of a duration of usage, a start of usage, an end of usage, and a number of usage events of the at least one article of medical equipment in the first operational mode.

15. The method of claim 1, comprising at least one of billing a payor for the monetary value of the usage of at least one article of medical equipment during a first time period and storing the monetary value of the usage of the at least one article of medical equipment in a data storage location in association with information identifying the patient.

16. The method of claim 1, wherein the second time period is different than the first time period.

17. A method of monitoring usage of a patient medical support system including an article of medical equipment and a telepresence system, comprising:
 receiving a medical equipment operational mode data signal at a first monitoring location from the patient medical support system located remote from the first monitoring location at a patient location, the medical equipment operational mode data signal indicative of a medical equipment operational mode of at least two operational modes of the article of medical equipment;
 receiving a medical equipment usage data signal at the first monitoring location from the patient medical support system, the medical equipment usage data signal indicative of usage of the article of medical equipment in the medical equipment operational mode;
 receiving a first telepresence system operational mode data signal at the first monitoring location from the patient medical support system, the first telepresence system operational mode data signal indicative of a first telepresence system operational mode of at least two operational modes of the telepresence system;
 receiving a first telepresence system usage data signal at the first monitoring location from the patient medical support system, the first telepresence system usage data signal indicative of usage of the telepresence system in the first telepresence system operational mode;
 determining an amount of usage of the article of medical equipment based at least in part on the medical equipment usage data signal;
 determining an amount of usage of the telepresence system based at least in part on the first telepresence system usage data signal;
 determining at least one user identification associated with a user of the patient medical support system;
 retrieving a base rate, a medical equipment unit rate for usage of the medical equipment in the medical equipment operational mode, and a first telepresence system unit rate for usage of the telepresence system in the first telepresence system operational mode from a data storage device;
 determining a monetary value of the usage of the patient medical support system by multiplying the medical equipment unit rate by the amount of usage of the article of medical equipment to obtain a first value, and multiplying the first telepresence system unit rate by the amount of usage of the telepresence system to obtain a second value, and summing the base rate, the first value, and the second value;
 and
 storing information to a data storage device, the information regarding at least one of the medical equipment operational mode, the usage of the article of medical equipment, the first telepresence system operational mode and the usage of the telepresence system.

18. The method of claim 17, including
 dissociating information identifying the patient from the determined amount of usage of the patient medical support system; and
 storing the information regarding at least one of the medical equipment operational mode, the usage of the article of medical equipment, the first telepresence system operational mode and the usage of the telepresence system to the data storage device in association with anonymized patient identifier data.

19. The method of claim 18, including transmitting information to a second monitoring location remote from the first monitoring location, wherein the data storage device is located at the second monitoring location, the transmitted information regarding at least one of the medical equipment operational mode, the usage of the article of the medical equipment, the first telepresence system operational mode and the usage of the telepresence system, in association with the anonymized patient identifier data.

20. The method of claim 17, including
 combining the determined amount of usage of the article of medical equipment with amount of usage values determined from a plurality of other patients.

21. The method of claim 17, including associating the amount of usage of the telepresence system with a patient based at least in part on the at least one user identification.

22. The method of claim 17, including
 receiving a second telepresence system usage data signal indicative of an amount of usage of the telepresence system in a second telepresence system operational mode from the patient location at the monitoring location, the second telepresence system operational mode being one of the two or more different telepresence system operational modes; and
 determining the amount of usage of the telepresence system in the second telepresence system operational mode based at least in part on the second telepresence system usage data signal.

23. The method of claim 22, wherein the second telepresence usage data signal is indicative of telepresence system usage occurring during a different time period than usage indicated by the first telepresence system usage data signal.

24. The method of claim 17, wherein the first telepresence system operational mode data signal is indicative of at least one of a turned on operational mode, a turned off operational mode, a standby operational mode, a send communication operational mode, a receive communication operational mode, an audio communication operational mode, a video communication operational mode, a user-initiated operational mode, and a medical care provider-initiated operational mode of the telepresence system.

25. The method of claim 17, including at least one of billing a payor for the monetary value of the usage of the patient medical support system and storing the monetary value of the usage of the patient medical support system in a data storage location in association with information identifying the patient.

26. The method of claim 17, including storing the information regarding at least one of the medical equipment operational mode, the usage of the article of medical equipment, the first telepresence system operational mode and the usage of the telepresence system to the data storage device in association with the at least one user identification.

27. The method of claim 17, including storing the information regarding at least one of the medical equipment operational mode, the usage of the article of medical equipment, the first telepresence system operational mode and the usage of the telepresence system to the data storage device in association with the information identifying the patient.

28. A medical support monitoring system comprising:
a first telepresence system for use at a first monitoring location including
at least one user input device adapted to accept a communication from a first user at the first monitoring location for transmission to a second user of a patient medical support system at a patient location remote from the first monitoring location via a two-way communication link; and
at least one user output device adapted to deliver a communication to the first user, the communication received from the second user via the two-way communication link;
first communication circuitry forming a portion of the two-way communication link between the medical support monitoring system at the first monitoring location and the patient medical support system at the patient location, the patient medical support system including a second telepresence system, an article of medical equipment, and second communication circuitry forming a portion of a two-way communication link, wherein the first communication circuitry is adapted to
receive at least one operational mode data signal indicative of at least one operational mode of the patient medical support system;
receive at least one usage data signal indicative of an amount of usage of the patient medical support system in the at least one operational mode;
receive via the two-way communication link the communication from the second user to the first user; and
transmit via the two-way communication link the communication from the first user to the second user;
a data storage device; and
electrical control circuitry configured to
determine the identity of at least one user of the patient medical support system;
determine an amount of usage of the patient medical support system from the usage data signal;
retrieve a base rate and a unit rate for usage of the patient medical support system from the data storage device;
determine a monetary value of the usage of the patient medical support system in the at least one operational mode based at least in part on the amount of usage of the patient medical support system by multiplying the amount of usage by the unit rate to obtain a value and adding the obtained value to the base rate; and
control storage of information relating to at least one of the at least one operational mode and the amount of usage of the patient medical support system in the at least one operational mode in the data storage device in association with the identification of the at least one user of the patient medical support system.

29. The medical support monitoring system of claim 28, wherein the first communication circuitry is adapted to receive an identification data signal from the patient medical support system.

30. The medical support monitoring system of claim 29, wherein the electrical control circuitry is configured to determine the identity of at least one user of the patient medical support system based at least in part on the identification data signal.

31. The medical support monitoring system of claim 29, wherein the identification data signal is a device identification data signal indicative of the device identity of at least a portion of the patient medical support system, and wherein the electrical control circuitry is configured to determine the identity of the at least one user of the patient medical support system by retrieving a user identity associated with the device identity of the at least a portion of the patient medical support system from the data storage device, wherein the user identity data is stored in the memory location in association with the device identity of the at least a portion of the patient medical support system.

32. The medical support monitoring system of claim 28, wherein the first communication circuitry is adapted to transmit a query addressed to at least a portion of the patient medical support system, and receive the at least one operational mode data signal and the at least one usage data signal from the patient medical support system in response to the query.

33. The medical support monitoring system of claim 32, wherein the electrical control circuitry is configured to determine the identity of at least one user of the patient medical support system based at least in part on the identification data signal.

34. The medical support monitoring system of claim 28, wherein the communication circuitry is adapted to provide at least one of WiFi, cellular, wireless, radio frequency, satellite, and BlueTooth communication.

35. The medical support monitoring system of claim 28, wherein the first telepresence system includes at least one of a two-way audiovisual system, a microphone, a speaker, a video display, and a camera.

36. An article of manufacture comprising:
one or more non-transitory machine-readable data storage media bearing one or more instructions for
receiving a medical equipment operational mode data signal at a first monitoring location from a patient medical support system located remote from the first monitoring location at a patient location, the medical equipment operational mode data signal indicative of a medical equipment operational mode of at least two operational modes of the article of medical equipment;
receiving a medical equipment usage data signal at the first monitoring location from the patient medical support system, the medical equipment usage data signal indicative of usage of the article of medical equipment in the medical equipment operational mode;

receiving a first telepresence system operational mode data signal at the first monitoring location from the patient medical support system, the first telepresence system operational mode data signal indicative of a first telepresence system operational mode of at least two operational modes of the telepresence system;

receiving a first telepresence system usage data signal at the first monitoring location from the patient medical support system, the first telepresence system usage data signal indicative of usage of the telepresence system in the first telepresence system operational mode;

determining an amount of usage of the article of medical equipment based at least in part on the medical equipment usage data signal;

determining an amount of usage of the telepresence system based at least in part on the first telepresence system usage data signal;

receiving a first telepresence system operational mode data signal at the first monitoring location from the patient medical support system, the first telepresence system operational mode data signal indicative of a first telepresence system operational mode of at least two operational modes of the telepresence system;

receiving a first telepresence system usage data signal at the first monitoring location from the patient medical support system, the first telepresence system usage data signal indicative of usage of the telepresence system in the first telepresence system operational mode;

determining at least one user identification associated with a user of the patient medical support system;

retrieving a base rate, a medical equipment unit rate for usage of the medical equipment in the medical equipment operational mode, and a first telepresence system unit rate for usage of the telepresence system in the first telepresence system operational mode from a data storage device;

determining a monetary value of the usage of the patient medical support system by multiplying the medical equipment unit rate by the amount of usage of the article of medical equipment to obtain a first value, and multiplying the first telepresence system unit rate by the amount of usage of the telepresence system to obtain a second value, and summing the base rate, the first value, and the second value;

dissociating information identifying the patient from the determined amount of usage of the patient medical support system; and storing information to a data storage device, the stored information regarding at least one of the medical equipment operational mode, the usage of the article of the medical equipment, the first telepresence system operational mode and the usage of the telepresence system, in association anonymized patient identifier data.

* * * * *

UNITED STATES PATENT AND TRADEMARK OFFICE
CERTIFICATE OF CORRECTION

PATENT NO.           : 9,838,645 B2
APPLICATION NO.      : 14/089478
DATED                : December 5, 2017
INVENTOR(S)          : Roderick A. Hyde et al.

Page 1 of 1

It is certified that error appears in the above-identified patent and that said Letters Patent is hereby corrected as shown below:

In the Claims

Column 40, Line 25, Claim 1: "least one base rate the first value and the second value" should read --least one base rate, the first value and the second value--

Signed and Sealed this
Fourteenth Day of August, 2018

Andrei Iancu
*Director of the United States Patent and Trademark Office*